US012597519B2

(12) United States Patent
Feng et al.

(10) Patent No.: US 12,597,519 B2
(45) Date of Patent: Apr. 7, 2026

(54) METHODS FOR CHARACTERIZING AND TREATING A CANCER TYPE USING CANCER IMAGES

(71) Applicant: TESARO, INC., Waltham, MA (US)

(72) Inventors: Bin Feng, Waltham, MA (US); Hailei Zhang, Waltham, MA (US); Jaegil Kim, Waltham, MA (US)

(73) Assignee: Tesaro, Inc., Waltham, MA (US)

( * ) Notice: Subject to any disclaimer, the term of this patent is extended or adjusted under 35 U.S.C. 154(b) by 900 days.

(21) Appl. No.: 17/608,834

(22) PCT Filed: May 6, 2020

(86) PCT No.: PCT/IB2020/054297
§ 371 (c)(1),
(2) Date: Nov. 4, 2021

(87) PCT Pub. No.: WO2020/225753
PCT Pub. Date: Nov. 12, 2020

(65) Prior Publication Data

US 2022/0319704 A1 Oct. 6, 2022

Related U.S. Application Data

(60) Provisional application No. 62/844,038, filed on May 6, 2019.

(51) Int. Cl.
*G16H 50/20* (2018.01)
*G06T 7/00* (2017.01)
(Continued)

(52) U.S. Cl.
CPC .......... *G16H 50/20* (2018.01); *G06T 7/0012* (2013.01); *G06V 10/764* (2022.01);
(Continued)

(58) Field of Classification Search
CPC ........................................ G06T 2207/30024
See application file for complete search history.

(56) References Cited

U.S. PATENT DOCUMENTS 7,720,267 B2 5/2010 Fuchs et al.
10,592,779 B2 * 3/2020 Madani ................. G06F 18/24
(Continued)

FOREIGN PATENT DOCUMENTS

CA 2948499 A1 5/2018
EP 3049536 B1 * 5/2019 .......... C12Q 1/6886
(Continued)

OTHER PUBLICATIONS

Geert Litjens et al: "Deep learning as a tool for increased accuracy and efficiency of histopathological diagnosis", Scientific Reports, vol. 6, No. 1, May 23, 2016.
(Continued)

*Primary Examiner* — Di Xiao
(74) *Attorney, Agent, or Firm* — Janet C. Effler; Kelly A. Gauger

(57) ABSTRACT

Described herein are methods, systems, devices and computer program products for characterizing or identifying a type of cancer. Also described are methods of treating a characterized or identified chancer. For example, certain methods may be used to characterize a homologous recombination deficiency status of a cancer.

18 Claims, 10 Drawing Sheets

(51) Int. Cl.

| | |
|---|---|
| ***G06V 10/764*** | (2022.01) |
| ***G06V 10/774*** | (2022.01) |
| ***G06V 10/82*** | (2022.01) |
| ***G16H 30/40*** | (2018.01) |

(52) U.S. Cl.

CPC .......... *G06V 10/7753* (2022.01); *G06V 10/82* (2022.01); *G16H 30/40* (2018.01); *G06T 2207/20081* (2013.01); *G06T 2207/20084* (2013.01); *G06T 2207/30024* (2013.01); *G06T 2207/30096* (2013.01); *G06V 2201/03* (2022.01)

(56) References Cited

U.S. PATENT DOCUMENTS

| | | | | |
|---|---|---|---|---|
| 10,650,520 | B1 | 5/2020 | Beck et al. | |
| 10,650,929 | B1 | 5/2020 | Beck et al. | |
| 2019/0340468 | A1 | 11/2019 | Stumpe et al. | |
| 2019/0347557 | A1 | 11/2019 | Khan | |
| 2020/0090326 | A1 | 3/2020 | Fahmi et al. | |
| 2022/0028481 | A1 * | 1/2022 | Pozzorini | G16B 40/20 |

FOREIGN PATENT DOCUMENTS

| | | | | |
|---|---|---|---|---|
| WO | 2013/049153 | A2 | 4/2013 | |
| WO | 2015/020691 | A1 | 2/2015 | |
| WO | 2017/142629 | A1 | 8/2017 | |
| WO | 2017/165801 | A1 | 9/2017 | |
| WO | 2018165103 | A1 | 9/2018 | |
| WO | WO-2018222979 | A1 * | 12/2018 | G01N 1/30 |
| WO | 2019/108695 | A1 | 6/2019 | |
| WO | 2020/081463 | A1 | 4/2020 | |

OTHER PUBLICATIONS

Sun Wenqing et al: "Enhancing deep convolutional neural network scheme for breast cancer diagnosis with unlabeled data", Computerized Medical Imaging and Graphics, Pergamon Press, New York, NY, US, vol. 57, Jul. 19, 2016, pp. 4-9.

Zhongyi Han et al: "Breast Cancer Multi-classification from Histopathological Images with Structured Deep Learning Model", Scientific Reports, vol. 7, No. 1, Jun. 23, 2017 (Jun. 23, 2017).

International Search Report and Written Opinion in corresponding International Application No. PCT/IB2020/054297, mailed Nov. 3, 2020 (19 pages).

Coudray, N., Ocampo, P.S., Sakellaropoulos, T. et al. Classification and mutation prediction from non-small cell lung cancer histopathology images using deep learning. Nat Med 24, 1559-1567 (2018). https://doi.org/10.1038/s41591-018-0177-5.

J. Deng, W. Dong, R. Socher, L.-J. Li, Kai Li and Li Fei-Fei, "ImageNet: A large-scale hierarchical image database," https://image-net.org/static_files/papers/imagenet_cvpr09.pdf (2009).

Davies H, et al. HRDetect is a predictor of BRCA1 and BRCA2 deficiency based on mutational signatures. Nat Med. Apr. 2017;23(4):517-525. doi: 10.1038/nm.4292. Epub Mar. 13, 2017. PMID: 28288110; PMCID: PMC5833945.

Szegedy, C., Vanhoucke, V., Ioffe, S., Shlens, J., & Wojna, Z. (Dec. 2, 2015). Rethinking the inception architecture for computer vision. arXiv.org. https://arxiv.org/abs/1512.00567.

* cited by examiner

Input image data corresponding to cancer into trained learning model
510

Output, from the trained learning model, a homologous recombination deficiency status for the cancer
520

Identifying the cancer as homologous recombination deficient or homologous recombination proficient
530

METHODS FOR CHARACTERIZING AND TREATING A CANCER TYPE USING CANCER IMAGES

The present application claims priority from U.S. provisional application No. 62/844,038 filed on 6 May 2019, the entire content of which is hereby incorporated herein by reference.

FIELD OF THE INVENTION

Described herein are methods for characterizing a cancer in an individual (human) as based on a cancer type, such as homologous recombination deficient status of the cancer. Also described are methods of treating an individual with a characterized cancer. Further described herein are further methods, systems, learning models and computer program products and other aspects for characterizing a cancer.

BACKGROUND

Cancer is a serious public health problem affecting millions of patients worldwide. Effective therapies for cancer often rely on accurate cancer classifications, as certain cancer therapies may be more effective in treating a subgroup of caner types. While pathologists and oncologists are generally effective at distinguishing some cancer types by observing the histopathology of a tumor sample, the molecular basis for the pathology frequently cannot be determined by human observation alone. However, the effectiveness of a particular cancer treatment often depends on the molecular biology of a particular cancer strain rather than macroscale phenotypes.

Cancers can be characterized as homologous recombination deficient (also referred to as homologous repair deficient, or HRD or other terms, such as identified infra) or homologous recombination proficient (also referred to as homologous repair proficient, or HRP or other terms, such as identified infra). Homologous recombination is an essential pathway for DNA repair, particularly in the context of repairing double-stranded DNA breaks. A deficiency in homologous recombination may result in the utilization of other pathways for DNA repair, such as non-homologous end-joining (NHEJ). However, NHEJ is more error-prone compared to homologous recombination in DNA repair, resulting in a greater number of mutations and thus increasing the risk of chromosomal instability and tumor transformation. Single-strand breaks in the DNA of a cancer cell may be repaired using poly ADP ribose polymerase (PARP). A PARP inhibitor administered to the cancer can prevent single-strand break repair, leading to a double-strand break in the DNA. The double-strand break can be repaired using homologous recombination in HRP cancer strains (or cancers which are not HRD). However, HRD cancer strains are unable to repair the double-strand break, and are therefore particularly susceptible to treatment using a PARP inhibitor.

Thus, it can be useful to determine or diagnose whether or not a cancer is HRD for treatment planning; for example, treating an individual with a cancer that is characterized or identified or diagnosed as HRD with a PARP inhibitor or other drug substance that is effective because the cancer is HRD. Such anti-cancer agents are described hereinbelow, including by way of example niraparib (marketed under the trade mark "Zejula") which is approved for treatment of cancers which are characterised as HRD.Mutations in certain genes (e.g., BRCA1 and BRCA2) give rise to a genome-wide mutational signature associated with HRD. See Polak et al., *A mutational signature reveals alterations underlying deficient homologous recombination repair in breast cancer*, Nature Genetics, vol. 49, no. 10, pp. 1476-1486 (2017). However, relying on mutational sequencing analysis to characterize a cancer as homologous recombination deficient can result in delayed treatment or may be under-inclusive in detecting HRD cancers. Such characterization can also be relatively expensive and not necessarily accessible.

A molecular (sequence-)based in vitro diagnostic test ("MyChoice") for the HRD status of a cancer is available from Myriad Genetics, Inc. The list price for a test is approximately US$4,000.00. This test is approved by the FDA (USA) as a companion diagnostic for use of the PARP inhibitor niraparib. In this test, HRD is defined by tumor BRCA mutation or a composite genomic instability score of greater than or equal to 42; i.e. a cancer is characterised as HRD if the test score (HRD score) is at least 42, else it is characterised as not-HRD (HRP).

The HR status of a cancer is a biomarker inasmuch as HRD cells are more susceptible to the effects of DNA damaging agents such as platinum agents or PARP inhibitors.

An aim of the present invention is to provide a new way of determining or characterizing (predicting or diagnosing) the homologous recombination (HR) status of an (human) individual's or subject's cancer, and one which is able to more rapidly identify the HR status (e.g. compared to molecular testing of a cancer sample, such as by the "MyChoice" test supra) and hence more rapidly start the subject with a suitable anti-cancer agent, such as a PARP inhibitor, if the cancer is determined as HRD. Alternative or additional aims of the present invention in various of its aspects and embodiments are to provide a cheaper solution to determining the HR status, particularly compared to the cost of molecular testing such as the "MyChoice" test), and/or make use of images of cancer prepared according to standard techniques (e.g. biopsy cancer sample stained with H&E stain)—which images are generally prepared in any event in the oncology field for a pathologist to examine meaning specific embodiments dovetail with existing pathology/oncology practice, and/or is readily-accessible, e.g. being provided 'at the edge' (e.g. aspects and embodiments of the invention may be incorporated into the imaging equipment/system which images the cancer) or through communication networks (e.g. aspects and embodiments of the invention may be implemented as an online service and system). Another aim of the present invention in various of its aspects and embodiments is to provide an automatic characterization of the HR status, for instance through computer-implementation of at least the HR characterization.

It is also important to point out that hitherto an expert pathologist has been unable to distinguish between HRD and not-HRD from visual analysis and inspection of a histology or histopathology (slide) image of a cancer, including those provided with suitable staining (such as H&E stain). The inventors have surprisingly found that it is, in fact, possible to characterize the HR status, in particular the HRD status, of a cancer from an image thereof, in particular a histology or histopathology (whole) slide image.

SUMMARY OF THE INVENTION

Described herein are inter alia methods, systems, devices, and computer program products for identifying or characterizing a cancer, as well as methods for treating an identified or characterized cancer.

According to the present invention there is provided a variety of aspects and embodiments as described herein, including as set forth in the appended set of claims which are incorporated into this section by cross-reference if not present already.

The present invention is particularly, but not exclusively, concerned with the characterization, identification or prediction of the homologous recombination (HR) status of a cancer, in particular whether or not the cancer is HR deficient (HRD), which is considered a biomarker to identify cancers which are more susceptible to the effects of certain anti-cancer agents, for example DNA damaging agents, such as platinum agents or PARP inhibitors. It is to be noted that HRD is a term for which various synonyms exists, including in particular HRD-positive (meaning a cancer is characterised as being HRD), and likewise for the terms not-HRD and HRP, including in particular HRD-negative (meaning a cancer is not characterised as being HRD). The use of the terms HRD, not-HRD and HRP herein are to be read accordingly. Moreover, the terms ‘not-HRD’ and ‘HRP’ herein have the same meaning (a cancer not characterised as being HRD or characterised as being not HRD), even if strictly speaking HRP may be considered to be a sub-type of the class ‘not-HRD’.

According to the present invention there is also provided a system for use to characterize the homologous recombination (HR) status of a cancer of a subject, the system having an image analysis system which has: an input for receiving an image of a cancer of a subject, a machine learning (ML) model to characterize the HR status of a cancer of a subject from an image of the cancer, one or more processors for a processing a cancer image with the ML model to characterize the HR status of the cancer in said cancer image, and an output to provide an HR status for a cancer based on the processing of an image of said cancer by the ML model.

The present invention may be used to provide a diagnosis of the HRD status of a cancer (e.g. HRD or not HRD) from its image, e.g. avoiding the need for a human evaluation or decision (e.g. by a pathologist), or as a clinical decision support (e.g. for a clinician to be provided with data on the HRD status to assist the clinician to make a decision on treatment for the cancer subject, e.g. whether to administer an appropriate anti-cancer agent if the clinician assesses or decides if the cancer is HRD based on the HRD status data).

In embodiments, the image analysis system has an image pre-processor to process an image of a cancer received as input in preparation for processing by the ML model. The image pre-processor may process an input image for any one or more cropping, re-orienting, re-sizing, creating image portions (e.g. into patches or tiles, as is disclosed elsewhere herein), normalization (e.g. of any staining applied to the cancer for the image thereof and/or other image aspects which may vary due to sample preparation or imaging techniques), image segmentation (e.g. to remove noise or background), etc. etc. As an example, an image may be too large (e.g. too many pixels) as compared to what the ML model requires as its input. The image pre-processor can address this by re-sizing, cropping or creating image portions of the requisite size. Other operations may be for color management and/or to remove image artefacts and/or to ensure the image processed by the ML model has a degree of consistency (e.g. in terms of image intensity, staining characteristics, etc.) to the training images used to train the ML model to improve the accuracy of the ML model in its characterization of the HR status in an input image.

By way of example, stain normalization may be by the Vahadane algorithm (Vahadane, Abhishek, et al. “*Structure-preserving color normalization and sparse stain separation for histological images.*” *IEEE transactions on medical imaging* 35.8 (2016): 1962-1971). By way of example, image artefacts may be processed using HistoQC, an open-source quality control tool for digital pathology slides (Janowczyk A., Zuo R., Gilmore H., Feldman M., Madabhushi A., *JCO Clinical Cancer Informatics,* 2019). Other stain normalization (Macenko and Reinhard) and artefact processing algorithms may, of course, be used.

Where an image pre-processor is provided as part of the invention, the model typically receives and processes an image based on, or which results from, the processing by the image pre-processor. An image so received at the input may then be considered as a pre-cursor image (or raw image). Alternatively, any such image preparation for the model may be done outside of the system and such a prepared image is then the image received at the input (and the image provided to the model).

Preferably, the HR status is to identify if the cancer is HR deficient. The HR status may identify if the cancer is other than HR deficient (HRD), e.g. ‘not HRD’ or HR proficient (HRP). In embodiments, the HR status is to identify if the cancer is HRD or HRP (e.g. only those two classes).

Typically, the image is of a specimen sample of the cancer (e.g. a cancer tissue sample), preferably in the form of a histology image (which may be a pathology slide image or histopathology slide image), for instance as a whole slide image.

Typically, the image is of a stained cancer sample, especially where the image is a histology image. Staining may be by any conventional technique, particularly staining by hematoxylin and eosin (commonly referred to as ‘H&E stain’). Obtaining H&E-stained histological images for cancer samples is standard procedure in clinical settings It will be understood that the cancer image will typically be in the form of image data; in other words, in the form of image data which is a representation of an image of a cancer. Thus, in embodiments the image (e.g. provided as input) is image data (and the term “image” herein is substitutable with the term “image data”). Typically, the image data is a digital representation of a cancer image (e.g. based on a digital image composed of pixels). So, the image data may be pixel-level data.

The image data may be in the form of a data structure. The image data structure and model (which in turn may comprise a data structure) may be stored in memory and one or more data processors may process the data structure and the model to characterize the HRD status in the image data. The processing may involve parsing of the image data and/or model.

The output may be in the form of data (e.g. a data structure) which represents the characterised HRD status for the image data.

Any data structure may be in the form of a vector.

Typically, the image is a digital image (or digital image data), for example obtained by a digital imaging (image capture or recording) system (e.g. a digital camera or a digital scanner), such as is known for digital pathology, for instance for obtaining a digital image of a whole slide image. In embodiments, the image is image data representing a whole slide image. Whole slide images may be acquired by commercially available whole slide imaging systems, such as the Philips IntelliSite (DEN160056) and Aperio AT2 DX System (K190332)). The invention (including any one or more of the system, method, computer program product and computer-readable storage medium) may be implemented in or incorporated into (e.g. integrated into) an imaging system, e.g. for imaging slides, such as those disclosed herein, for example a histology/histopathology/pathology slide scanner.

The image of the cancer may be a portion of an image of a cancer (with cancer content) or may be in the form of a plurality (e.g. a series or sequence) of portions of an image of a cancer. This (in particular the latter instance) may be useful where the cancer image is too large in size for the learning model or image analysis system to operate on as a whole, for example where the image to be used is a whole slide image. In addition or alternatively, this may be useful to remove any image portions of the full cancer image in which the cancer is not present, either at all (e.g. just background) or present but below a minimum content level (e.g. less than a certain amount of the area of the image portion is not of the cancer, e.g. too much background). This is a form of image processing so that the image for the learning model or image analysis system is predominantly, if not exclusively, of the cancer (e.g. minimal background or no background). This image processing may be done by an image pre-processor, which in some embodiments or aspects forms a part of the invention.

The image portions may be patches or tiles, as detailed further herein.

An image of a cancer may be divided up into a grid or array of image portions, which image portions may be contiguous or overlapping. The image portions may each be of a size (e.g. number of pixels) required by the learning model or image analyzer.

In embodiments, the image or image data is made up of (or represented by or corresponds to) the image portions from a cancer image (e.g. all of those image portions or all of those having a cancer content present therein, e.g. cancer content at or above a minimum threshold level in that portion). In embodiments, the HRD status for each image portion is determined and the HRD status for the cancer is determined from the HRD status of each image portion, for instance by a function which determines or predicts the HRD status of the cancer from the HRD status of each image portion (e.g. by aggregation or averaging (mean)).

In embodiments, the learning model is trained using image portions of the training images (e.g. whole slide images) and each of those image portions is assigned the same training label as the training label for the training image (e.g. HRD or HRP).

In embodiments, the (trained) learning model predicts (e.g. HRD status, such as HRD probability) for each image portion of an input image and a function predicts on the input image from the image portion predictions (e.g. of HRD status, such as HRD probability), e.g. by aggregating or averaging the image portion predictions (for instance, an image prediction (e.g. HRD status, such as HRD probability) is the sum all image portion predictions (e.g. HRD probabilities) divided by the total number of image portions)).

For those aspects and embodiments of the invention using a learning model, the use of image portions (tiles) may follow the approach as set out in Coudray N et al, *Classification and mutation prediction from non-small lung cancer histopathology image using deep learning, Nature Medicine* (2018).

The one or more processors (or data processor(s)) can be any known in the art (or developed in the future), for instance any one or more of a computer processing unit (CPU), graphics processing unit (GPU) and tensor processing unit (TPU). The processor(s) may be on or form part of a local device (e.g. a personal computer (PC) or an imaging apparatus or system (e.g. slide scanner)) so is accessed locally, or may be hosted remotely (e.g. on a cloud platform) so is accessed remotely over a data communication network or is part-local and part-remote (e.g. some parts are cloud-based or at a node of a data communication network). Where aspects and embodiments of the invention are implemented on a data communication network, these aspects and embodiments may be considered as implementing telepathology.

Typically, the one or more processors will be part of a computer device (or computer module) or computer system which further comprises one or memory stores for storing an image of a cancer and the image analysis system (or parts thereof, e.g. learning model and/or the image (pre-)processor) and/or the learning model or image analyzer and instructions which are executable by the processor(s) to cause the image analysis system (or parts thereof) or the learning model or the image analyzer to determine the HR status of the image in the memory store.

Expressed more generally, aspects and embodiments of the present invention may be computer-implemented, either in whole or in part. Additionally or alternatively, aspects and embodiments of the present invention may automatically determine the cancer characteristic or status (e.g. HR/HRD status) from the cancer image.

Preferably, the learning model comprises a classifier to classify a cancer in an input cancer image with respect to a set of HR classes.

It will be understood that any naming convention may be used for the HR classes (both for training and/or the output from those aspects concerning the characterization, identification, diagnosis or prediction of whether or not a cancer is HRD, for instance the output from a learning model)—including descriptive (such as HRD, not-HRD, HRP) and non-descriptive/representative (such as class 0, class 1, etc.). This is unimportant provided it is known which HR status is being represented by the class names (e.g. class 0=HRD and class 1=not-HRD/HRP or vice-versa). Accordingly, the present invention is not limited to any particular naming or labelling convention for identifying which HR class or HR category a cancer belongs to, and such naming or labelling referred to herein is not necessarily prescriptive or limiting. For instance, if a classifier classifies a cancer as belonging to the class for HRD (or HRD-positive), this is not determinative that the class (or any associated training labelling) is named 'HRD' as such. As already stated, the characterization or labelling used can either be descriptive or representative of the respective HR class or category.

It is also to be pointed out that specifying that a cancer is homologous recombination deficient or HRD is the same as specifying the cancer is HRD positive or its related derivatives, such as HRDpos, HRD+, etc. Likewise, HRP is the same as the term HRD negative or its related derivatives, such as not-HRD, HRDneg, HRD−, etc. Moreover, use of the term HRP and its equivalents may simply mean that the cancer is not characterized/determined/predicted/diagnosed as being HRD (which may be termed 'not-HRD'), especially in the case where the invention is for making a binary assessment of a cancer (HRD or not). Thus, HRP in the context of the invention may simply mean the cancer is not-HRD.

Preferably, the HR classes include classes for HR deficient (HRD) and for one or more other HR classes (e.g. 'not HRD' or HRP). Preferably, the output is the classification of a cancer in an input cancer image with respect to the HR class set. The output may be a probability distribution for the HR class set (e.g. using a SoftMax or SoftMax Cross Entropy function or other classification function). Thus, the output is a prediction of the likelihood of a cancer in an input cancer image belonging to one HR class relative to the other HR class(es). This is typically expressed as a numerical value for each class, either as some value in the range 0-1 with the sum of the values for each class totaling 1, or as a percentage value with the sum of the values for each class totaling 100%. For binary classification, for instance, the output values for each of the two classes (e.g. HRD and HRP) may be some value 'x' calculated by the learning model for the first class (e.g. HRD or HRP) and then the value '1−x' for the other class (e.g. HRP or HRD) or some equivalent differently expressed numeric relationship, such as percentage values (x % and 100−x %).

If the prediction for a particular HR class satisfies a threshold (e.g. HRD probability meeting a threshold requirement), the output identifies the input as belonging to that HR class. The threshold may take many forms, such as based on a numerical value or ranking of the prediction for the HR class, either in absolute terms or in relation to a numerical value or ranking for any other HR class or HR classes. For instance, where the model predicts the input as belonging to a certain HR class at or above a certain numeric value in a probability distribution, particularly in binary classification.

Preferably, the classifier is a binary classifier with HR classes representing HRD and HRP. The output may identify which one of the two HR classes the cancer in an input cancer image belongs to dependent on whether the prediction for one of the HR classes is or is not at a threshold (e.g. within a certain numeric range); for instance, if the prediction (e.g. HRD probability) for the class for HRD matches the associated threshold the output will identify the input as belonging to the class for HRD, otherwise the output will identify the class for HRP. As indicated above, the output may be the probability distribution for the two HR classes.

It is to be understand that the optional features, functions and properties described herein for the 'machine learning/ML model' (or its training) of the system or other aspect are equally applicable to the 'trained learning model' or 'learning model' feature in other aspects and their associated embodiments, and so can be incorporated into those aspects and embodiments mutatis mutandis. This is also true vice-versa in respect of statements or claims herein about a 'trained learning model' or 'learning model' and their training.

Preferably, the learning/ML model is created by training the learning/ML model with appropriate training data. In other words, the model itself learns, via a learning algorithm and user-selected hyperparameters (e.g. learning rate) a function for the desired task, as known in the art. For some aspects and embodiments of the invention, the model is trained to learn a mapping from an input image of a cancer to an HR status (HRD probability) for the cancer. Thus, the image features and relationships (e.g. pixel patterns representing a cancer that is HRD or differentiating a cancer that is HRD from a cancer that is HRP) are learnt, and do not result from feature engineering by a human domain expert (e.g. pathologist). In fact, as noted above, an expert pathologist is not able to extract the HR status of a cancer from an image thereof.

In embodiments, the ML model is trained by supervised learning; i.e., using labelled cancer images, the labels referring to the HR status of the cancer as shown in the respective training cancer images. Where the invention employs a classifier, the labels are the labels for the classes in the HR class set.

The HR labels may be determined using molecular information/signatures associated with the cancer shown in the images, as is known in the art or as described or exemplified elsewhere herein.

Preferably, when training the ML/learning model to learn which features in a cancer image are characteristic of a cancer which is HRD (or HRP), only images of a cancer which are determined as HRD and not HRD (e.g. HRP) with a high degree of (predicted) accuracy are used as labelled images for the model training (i.e. the training dataset). Images of cancers in the training set falling outside the required accuracy are not used.

It is to be understood that the terms 'ML model', 'learning model', and 'trained learning model' and the like encompass an ensemble of models.

In embodiments, the learning model is a deep learning (DL) model. The learning model may comprise at least one artificial neural network (ANN), for instance a feedforward ANN, a simple ANN (single hidden layer) or a deep ANN (more than one hidden layer). Preferably, the ANN is a convolutional neural network (CNN), for instance a deep CNN.

Conveniently, the learning model is derived from an existing pre-trained learning model. In other words, the learning model is derived by transfer learning using an existing pre-trained learning model. In this case, only some of the model weights are learnt from the training cancer images, particularly those towards the output end (the final layers or head) representing the specific image features in cancer images that characterize the HR status, with the other model weights (which identify low-level image features, such as edges, curves, other shapes, etc.) being established in the model by its prior training on other images, which may or may not be related to the task at hand. For example, the pre-trained model may have been trained already on the ImageNet set of images and/or images for some other pathology task.

Of course, the learning model could also be trained from scratch, for example using an existing model architecture where all of its model weights are randomized and then learnt solely from the training images of cancer used for the HR status determination task. However, pre-training is more convenient, particularly if the training dataset is not large.

The output may be a printed or printable report identifying the predicted HR status and/or an email or other electronic message, optionally including the probability for the HRD status, and optionally other data relating to the HR status.

In embodiments, the image is of a cancer tumor or a cancer tissue sample.

In embodiments, the cancer is selected from the group consisting of epithelial cancer, breast cancer, ovarian cancer, fallopian tube cancer, peritoneal cancer and endometrial cancer. In embodiments, the ovarian cancer is an advanced or recurrent cancer and/or is an epithelial cancer. In embodiments, the fallopian tube cancer is an advanced or recurrent cancer and/or is an epithelial cancer. In embodiments, the peritoneal cancer is a primary peritoneal cancer. In embodiments, the (primary) peritoneal cancer is an advanced or recurrent cancer and/or is an epithelial cancer. In embodiments, the cancer is an (advanced) ovarian, (advanced) epithelial ovarian, (advanced) fallopian tube, or (advanced) primary peritoneal cancer from a (human) subject who is in a complete or partial response to first-line platinum-based chemotherapy.

Typically, the cancer is in or from a human subject, for example an adult. Typically, the human is a living human subject or individual.

In embodiments, the learning model is configured to characterize the HR status in one or more types of cancer from images thereof.

Preferably, the cancer in an input image is a first type of cancer and the learning model is trained with training images of that first type of cancer, for instance solely with training images of that first type of cancer (in which case the learning model is only operable for that first type of cancer) or with training images including images of that first cancer type. The first type of cancer may be any of the types referred to herein.

In some embodiments or an aspect of the present invention, there is a method of identifying a cancer as homologous recombination deficient or homologous recombination proficient, comprises: inputting image data corresponding to the cancer into a (trained) learning model, wherein the (trained) learning model has been trained based on training image data comprising a first set of cancer image data labeled as homologous recombination deficient and a second set of cancer image data labeled as homologous recombination proficient, and wherein the (trained) learning model comprises a function that associates the inputted image data with a homologous recombination deficiency status; outputting, from the (trained) learning model, a homologous recombination deficiency status of the cancer; and identifying the cancer as homologous recombination deficient or homologous recombination proficient based on the outputted homologous recombination deficiency status of the cancer. At the outputting step there may be produced an output indicating the HRD status and the identifying step may identify the cancer as HRD or HRP based on said output.

The present invention also provides the method of appended claim 1.

In some embodiments, the homologous recombination deficiency status outputted by the (trained) learning model is or includes a likelihood that the cancer is homologous recombination deficient or a likelihood that the cancer is homologous recombination proficient. In some embodiments, the homologous recombination deficiency status or output outputted by the (trained) learning model is or includes a binary determination that the cancer is homologous recombination deficient or homologous recombination proficient.

In some embodiments, the training image data is generated by: labeling a training cancer image data as homologous recombination deficient if a cancer associated with the training cancer image data is predicted to be homologous recombination deficient using consensus labeling; and labeling the training cancer image data as homologous recombination proficient if a cancer associated with the training cancer image data is predicted to be homologous recombination deficient using consensus labeling. In some embodiments, consensus labeling comprises using a plurality of different feature thresholds to preliminarily label or identify the cancer as homologous recombination proficient; labeling the training cancer image data based on a frequency of the cancer associated with the training cancer image data being preliminarily labeled or identified as homologous recombination deficient or homologous recombination proficient across the plurality of thresholds.

In some embodiments, the training image data is generated by: labeling a training cancer image data as homologous recombination deficient if the likelihood of a cancer associated with the training cancer image data being homologous recombination deficient is above a first threshold likelihood; and labeling the training cancer image data as homologous recombination proficient if the likelihood of the cancer associated with the training cancer image data being homologous recombination deficient is below a second threshold likelihood. In some embodiments, the first threshold likelihood is about 0.75 or higher, for instance 0.95 or higher. In some embodiments, the second threshold likelihood is about 0.125 or lower, for instance 0.05 or lower. In embodiments, the first and second thresholds are respectively about 0.75 or higher and about 0.125 or lower, optionally about 0.95 or higher and about 0.05 or lower. In embodiments, the thresholds are with respect to a range from 0 to 1. Other thresholds can, of course, be selected.

In some embodiments, labeling the training cancer image data comprises using a classification algorithm to evaluate one or more weighted features, the one or more weighted features comprising at least: a first feature comprising a mutational signature score associated with the cancer, wherein the mutational signature score is associated with homologous recombination deficiency; and a second feature comprising a large-scale state transition (LST) score or a homologous recombination deficiency (HRD) score associated with the cancer. In some embodiments, the mutational signature score is determined using nucleic acid sequencing data associated with the cancer. In some embodiments, the nucleic acid sequencing data is derived from whole exome sequencing data. In some embodiments, the LST score or the HRD score is determined using a microarray, whole exome sequencing, or whole genome sequencing. In some embodiments, the one or more features are weighted using the classification algorithm. In some embodiments, the classification algorithm comprises a regression algorithm. In some embodiments, the regression algorithm comprises a least absolute shrinkage and selection operator (LASSO) regression algorithm.

In some embodiments, bi-allelic inactivation of one or more of BRCA1, BRCA2, ATM, ATR, BAP1, BARD1, BLM, BRIP1, MRE11A, NBN, PALB2, RAD51, RAD51B, RAD51C, RAD51D, RAD52, RAD54L, and XRCC2 is used to define a ground truth of homologous recombination deficiency for labeling the training cancer image data. In some embodiments, bi-allelic inactivation of BRCA1 or BRCA2 is used to define a ground truth of homologous recombination deficiency for labeling the training cancer image data.

In some embodiments, the cancer associated with the training cancer image data is defined by one or more features, and a threshold for the one or more features define a ground truth of homologous recombination proficiency for labeling the training cancer image data. In some embodiments, the threshold is a predetermined threshold. In some embodiments, the training cancer image data is labeled by consensus labeling.

In some embodiments, the image data is obtained from an image of cancer stained using hematoxylin and eosin (H&E) stain.

In some embodiments, the learning model is a deep learning model. In some embodiments, the learning model is a convolutional neural network (CNN) learning model.

In some embodiments, the cancer is adenocarcinoma, endometrial cancer, breast cancer, ovarian cancer, cervical cancer, fallopian tube cancer, testicular cancer, primary peritoneal cancer, colon cancer, colorectal cancer, gastric cancer, stomach cancer, small intestine cancer, squamous cell carcinoma of the anus, squamous cell carcinoma of the penis, squamous cell carcinoma of the cervix, squamous cell carcinoma of the vagina, squamous cell carcinoma of the vulva, soft tissue sarcoma, melanoma, renal cell carcinoma, lung cancer, non-small cell lung cancer, adenocarcinoma of the lung, squamous cell carcinoma of the lung, bladder cancer, gall bladder cancer, liver cancer, thyroid cancer, laryngeal cancer, salivary gland cancer, esophageal cancer, head and neck cancer, squamous cell carcinoma of the head and neck, prostate cancer, pancreatic cancer, mesothelioma, Merkel cell carcinoma, sarcoma, glioblastoma, a hematological cancer, multiple myeloma, B-cell lymphoma, T-cell lymphoma, Hodgkin's lymphoma/primary mediastinal B-cell lymphoma, chronic myelogenous leukemia, acute myeloid leukemia, acute lymphoblastic leukemia, non-Hodgkin's lymphoma, neuroblastoma, a CNS tumor, diffuse intrinsic pontine glioma (DIPG), Ewing's sarcoma, embryonal rhabdomyosarcoma, osteosarcoma, or Wilms tumor. In some embodiments, the cancer is breast cancer.

In some embodiments, the (trained) learning model is pre-trained using pre-training image data, wherein the pre-training image data comprises image data not associated with or not representing cancer images. In some embodiments, the (trained) learning model is pre-trained using pre-training image data, wherein the pre-training image data comprises image data associated with or representing cancer images.

In some embodiments or an aspect of the present invention, there is a method of generating labeled image data for training a learning model configured to characterize a (e.g. homologous recombination deficiency) status of a cancer, which comprises: training a classification model using data comprising one or more features associated with a plurality of labeled cancers, wherein the labeled cancers are labeled with its (e.g. a homologous recombination deficiency) status; inputting into the trained classification model feature data associated with an unlabeled cancer, wherein the unlabeled cancer is associated with unlabeled image data; labeling, using the trained classification model, the feature data associated with the unlabeled cancer with its (e.g. a homologous recombination deficiency) status; and labeling the unlabeled image data with the (e.g. homologous recombination deficiency) status using the (e.g. homologous recombination deficiency) status of the labeled feature data. In embodiments, the data comprising one or more features associated with a plurality of labeled cancers is ground truth data (or deemed to be ground truth data). In embodiments, the method involves training the classification model using the data comprising one or more features associated with the plurality of status (e.g. HRD status) labeled cancers thereby generating a function that associates the one or more features to the (e.g. HRD) status. In some embodiments, at least a portion of the labeled cancers are labeled as being of one status, for example homologous recombination deficient. In some embodiments, a second portion of the labeled cancers are labeled as another status, for example homologous recombination proficient. In embodiments, the labelled image data is input as training data to learning model to train the learning model to determine the (e.g. HRD) status of a cancer from its associated image data; e.g. to generate a learning model having a function that associates image data for a cancer with a (e.g. HRD) status for the cancer.

In some embodiments or an aspect of the present invention, a method of generating labeled image data for training a learning model configured to characterize a homologous recombination deficiency status of a cancer, comprises: training a (or at least a) first classification model using homologous recombination deficient (e.g. ground truth) data comprising one or more features associated with a plurality of labeled homologous recombination deficient cancers, and first (e.g. preliminary) homologous recombination proficient (e.g. ground truth) data comprising one or more features associated with a plurality of (e.g. preliminarily) labeled homologous recombination proficient cancers, wherein the (e.g. preliminarily) labeled homologous recombination proficient cancers are (e.g. preliminarily) labeled based on a first threshold for the one or more features, optionally thereby generating a first function that associates the one or more features to a homologous recombination deficiency status; inputting, into the trained first classification model, unlabeled feature data associated with a plurality of unlabeled cancers, wherein at least a portion of the unlabeled cancers are associated with unlabeled image data; (e.g. preliminarily) labeling, using the trained first classification model, the unlabeled feature data associated with the plurality of unlabeled cancers with a first homologous recombination deficiency status, thereby generating first (e.g. preliminarily) labeled feature data; training at least a second classification model using the homologous recombination deficient (e.g. ground truth) data and second (e.g. preliminary) homologous recombination proficient (e.g. ground truth) data comprising one or more features associated with the plurality of (e.g. preliminarily) labeled homologous recombination proficient cancers, wherein the (e.g. preliminarily) labeled homologous recombination proficient cancers are (e.g. preliminarily) labeled based on a second threshold for the one or more features, wherein the second threshold is different from the first threshold, optionally thereby generating a second function that associates the one or more features to a homologous recombination deficiency status; inputting, into the trained second classification model, the unlabeled feature data; (e.g. preliminarily) labeling, using the trained second classification model, the unlabeled feature data associated with the plurality of unlabeled cancer with a second homologous recombination deficiency status, thereby generating second preliminarily labeled feature data; labeling the unlabeled feature data based on the frequency of a given homologous recombination deficiency status across a set of (e.g. preliminarily) labeled feature data that were labeled using a plurality of different thresholds for the one or more features, wherein the set of (e.g. preliminarily) labeled feature data comprises at least the first (e.g. preliminarily) labeled feature data and the second (e.g. preliminarily) labeled feature data; and labeling the unlabeled image data with a homologous recombination deficiency status associated with selected labeled feature data. In some embodiments, the set of labeled feature data further comprises at least third labeled feature data labeled using a third trained classification model.

In some embodiments of generating labeled image data for training a learning model, the one or more features comprises at least: a first feature comprising a mutational signature score associated with the cancer, wherein the mutational signature is associated with homologous recombination deficiency; and a second feature comprising a large-scale state transition (LST) score associated with the cancer or a homologous recombination deficiency (HRD) score. In some embodiments, the mutational signature score is determined using nucleic acid sequencing data associated with the cancer. In some embodiments, the LST score or the homologous recombination deficiency score is determined using a microarray, whole exome sequencing, or whole genome sequencing.

In embodiments, the methods of labelling image data include one or more features as disclosed in Example 1 or Example 2. In embodiments, the labelling method involves training at least 5, 10, 20, 40, 60, 80, 100 or 150 classification models, each with a different threshold. In embodiments, the status is a probability for that status belonging to a particular class, for instance a HRD probability.

The labelling method identifies which data in a dataset is consistently (e.g. always) determined or predicted by the classification model(s) an HRD status which is below a predetermined HRD status threshold across the different labelling thresholds. Such data can then be used as putative ground truth HRP data samples (along with the ground truth HRD samples) for input as training data to a labelling classification model, e.g. logistic regression model. The trained labelling classification model then receives the whole dataset as input and determines or predicts an HRD status for all data. The data above and below selected HRD status thresholds are then considered ground truth for HRD and HRP, respectively, and these labels (or other representative labels) can be applied to the corresponding unlabeled image data. Such labelled image data can then be used for training an image classifier to determine or predict HRD status from images, as disclosed elsewhere herein. See Examples 2 and 4, by way of example.

The present invention also provides a system and a computer program product for implementing the labelling of the image data, e.g. computer-implementation of the training of the models and labelling by the trained learning models. Such methods and systems may use one or more memory stores and one or more data processors for respectively storing the data and model(s) and the processing. The training data and labelled data may be in the form of a data structure for processing (e.g. comprising parsing) by the one or more data processors.

In some embodiments of generating labeled image data for training a learning model, bi-allelic inactivation of one or more of BRCA1, BRCA2, ATM, ATR, BAP1, BARD1, BLM, BRIP1, MRE11A, NBN, PALB2, RAD51, RAD51B, RAD51C, RAD51D, RAD52, RAD54L, and XRCC2 is used to define a ground truth of homologous recombination deficiency. In some embodiments, bi-allelic inactivation of BRCA1 or BRCA2 is used to define a ground truth of homologous recombination deficiency.

In some embodiments or an aspect of the invention, a method of identifying a cancer as having microsatellite instability (MSI) or being microsatellite stable (MSS), comprises inputting image data corresponding to the cancer into a (trained) learning model, optionally wherein the (trained) learning model has been trained based on training image data comprising a first set of cancer image data labeled as MSI and a second set of cancer image data labeled as MSS, and wherein the (trained) learning model comprises a function that associates the inputted image data with a microsatellite instability status; outputting, from the (trained) learning model, a microsatellite instability status of the cancer; and identifying the cancer as having MSI or being MSS based on the outputted microsatellite instability status of the cancer. At the outputting step there may be produced an output indicating the MSI status and the identifying step may identify the cancer as MSI or MSS based on said output.

In some embodiments or an aspect of the present invention, a method of identifying a cancer as having a high microsatellite instability status (MSI-H) or having a low microsatellite instability status (MSI-L), comprises: inputting image data corresponding to the cancer into a (trained) learning model, optionally wherein the (trained) learning model has been trained based on training image data comprising a first set of cancer image data labeled as MSI-H and a second set of cancer image data labeled as MSI-L, and wherein the (trained) learning model comprises a function that associates the inputted image data with a microsatellite instability status; outputting, from the (trained) learning model, a microsatellite instability status of the cancer; and identifying the cancer as having a high microsatellite instability status (MSI-H) or having a low microsatellite instability status (MSI-L) based on the outputted microsatellite instability status of the cancer. At the outputting step there may be produced an output indicating the MSI status and the identifying step may identify the cancer as MSI-H or MSI-L based on said output.

In some embodiments, the cancer identified as MSI or MSI-H has a defective DNA mismatch repair system. In some embodiments, the cancer identified as MSI or MSI-H has a defect in a DNA mismatch repair gene.

In some embodiments or an aspect of the present invention, a method of identifying a cancer as having a high tumor mutation burden (TMB-H) or having a low tumor mutation burden (TMB-L), comprises: inputting image data corresponding to the cancer into a (trained) learning model, optionally wherein the (trained) learning model has been trained based on training image data comprising a first set of cancer image data labeled as TMB-H and a second set of cancer image data labeled as TMB-L, and wherein the (trained) learning model comprises a function that associates the inputted image data with a tumor mutation burden status; outputting, from the (trained) learning model, a tumor mutation burden status of the cancer; and identifying the cancer as having a high tumor mutation burden (TMB-H) or having a low tumor mutation burden (TMB-L) based on the outputted tumor mutation burden status of the cancer. At the outputting step there may be produced an output indicating the TMB status and the identifying step may identify the cancer as TMB-H or TMB-L based on said output.

In some embodiments, the TMB-H cancer has about 20 or more (such as 30 or more, 40 or more, 50 or more, 75 or more, or 100 or more) mutations per megabase in the cancer genome. In some embodiments, the TMB-L cancer has fewer than about 20 (such as 15 or fewer, 10 or fewer, 5 or fewer, 2 or fewer, or 1 or fewer) mutations per megabase in the cancer genome.

In some embodiments, the cancer identified as having a high tumor mutation burden is a hypermutated cancer. In some embodiments, the cancer identified as having a high tumor mutation burden has a mutation in polymerase delta (POLD). In some embodiments, the cancer identified as having a high tumor mutation burden has a mutation in polymerase epsilon (POLE).

The aspects and embodiments of the invention concerning HR/HRD status may be applied equally to the task of identifying microsatellite (in)stability or tumor mutation burden in cancers and thus are to be read as forming part of the present invention as it concerns microsatellite (in)stability or tumor mutation burden mutatis mutandis.

Also described herein or forming an aspect of the present invention is a system, comprising: one or more processors; and a non-transitory, computer readable storage medium comprising one or more programs executable by the one or more processors for performing any of the methods described above.

In some embodiments or an aspect of the present invention, a method of treating a homologous recombination deficient cancer in a patient comprises identifying the cancer as homologous recombination deficient using any method or system described herein (e.g. above or below) or according to the present invention; and administering to the patient a therapeutically effective amount of an anti-cancer agent effective against a homologous recombination deficient cancer.

In some embodiments or an aspect of the present invention, a method of treating a MSI cancer, a MSI-H cancer, or a TMB-H cancer in a patient, comprises: identifying the cancer as a MSI cancer, a MSI-H cancer, or a TMB-H cancer using any method or system described herein (e.g. above or below) or according to the present invention; and administering to the patient a therapeutically effective amount of an anti-cancer agent effective against the MSI cancer, the MSI-H cancer, or the TMB-H cancer.

In some embodiments of treating a cancer described above, the anti-cancer agent is a DNA-damaging or repair-inhibiting agent. In some embodiments, the anti-cancer agent is a PARP inhibitor, a platin, a topoisomerase inhibitor, or an inhibitor of a DNA checkpoint protein.

In some embodiments, the anti-cancer agent is a PARP inhibitor. In some embodiments, the PARP inhibitor is a small molecule, a nucleic acid, a polypeptide (e.g., an antibody), a carbohydrate, a lipid, a metal, or a toxin. In some embodiments, the PARP inhibitor is 2X 121, ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NMS-P293, NOV-140101, NU 1025, NU 1064, NU 1076, NU1085, olaparib (AZD2281), ONO2231, pamiparib, PD 128763, R 503, R554, rucaparib (RUBRACA) (AG-014699, PF-01367338), SBP 101, SC 101914, simmiparib, talazoparib (BMN-673), veliparib (ABT-888), WW 46, 2-(4-(trifluoromethyl)phenyl)-7,8-dihydro-5H-thiopyrano[4,3-d]pyrimidin-4-ol, or salts or derivatives thereof.

In some embodiments, the PARP inhibitor is niraparib or a salt or derivative thereof. In some embodiments, niraparib is administered at a dose equivalent to about 100 mg to about 300 mg of niraparib free base. In some embodiments, niraparib is administered at a dose equivalent to about 100 mg of niraparib free base. In some embodiments, niraparib is administered at a dose equivalent to about 200 mg of niraparib free base. In some embodiments, niraparib is administered at a dose equivalent to about 300 mg of niraparib free base.

In some embodiments of treating a cancer described above, the method further comprises administering an additional therapeutic agent or treatment. In some embodiments, the additional therapeutic agent or treatment comprises administering one or more of surgery, a radiotherapy, a chemotherapy, an immunotherapy, an anti-angiogenic agent, or an anti-inflammatory agent.

In some embodiments, the therapeutic agent is an immune checkpoint inhibitor. In some embodiments, the immune checkpoint inhibitor is an inhibitor of programmed death-1 protein (PD-1) signaling, T cell immunoglobulin and mucin protein 3 (TIM-3), Lymphocyte Activation Gene-3 (LAG-3), cytotoxic T-lymphocyte-associated protein 4 (CTLA-4), T cell immunoglobulin and ITIM domain (TIGIT), CEACAM, VISTA, BTLA, LAIR1, CD160, 2B4, CD80, CD86, B7-H3 (CD276), B7-H4 (VTCN1), HVEM, KIR, A2aR, MHC class I, MHC class II, GALS, adenosine, TGFR, B7-H1, B7-H4 (VTCN1), OX-40, CD137, CD40, indoleamine 2,3-dioxygenase (IDO), or colony-stimulating factor 1 receptor (CSF1R).

In some embodiments, the immune checkpoint inhibitor is an agent that inhibits PD-1 signaling. In some embodiments, the agent that inhibits PD-1 signaling is a small molecule, a nucleic acid, a polypeptide, a carbohydrate, a lipid, a metal, a toxin, or a PD-1 binding agent. In some embodiments, the agent that inhibits PD-1 signaling is a PD-1 binding agent. In some embodiments, the PD-1 binding agent is an antibody, an antibody conjugate, or an antigen-binding fragment thereof. In some embodiments, the PD-1 binding agent is selected from the group consisting of: BGB-A317, BI 754091, IBI308, INCSHR-1210, JNJ-63723283, JS-001, MEDI-0680, MGA-012, nivolumab, PDR001, pembrolizumab, PF-06801591, REGN-2810, dostarlimab, and derivatives thereof. In some embodiments, the PD-1 binding agent is dostarlimab or a derivative thereof. In some embodiments, the PD-1 binding agent is administered to the patient periodically at a first dose of about 500 mg once every 3 weeks for 3, 4, or 5 cycles followed by a second dose of about 1000 mg once every 6 weeks or more. In some embodiments, the PD-1 binding agent is administered to the subject at a first dose of about 500 mg once every 3 weeks for 4 cycles followed by a second dose of about 1000 mg once every 6 weeks or more.

In some embodiments, the agent that inhibits PD-1 signaling is a PD-L1/L2 binding agent. In some embodiments, the PD-L1/L2 binding agent is an antibody, an antibody conjugate, or an antigen-binding fragment thereof. In some embodiments, the PD-L1/L2 binding agent is atezolizumab, avelumab, CX-072, durvalumab, FAZ053, LY3300054, PD-L1 millamolecule, or derivatives thereof.

In some embodiments, the immune checkpoint inhibitor is an agent that inhibits TIM-3. In some embodiments, the agent that inhibits TIM-3 is a small molecule, a nucleic acid, a polypeptide, a carbohydrate, a lipid, a metal, a toxin or a TIM-3 binding agent. In some embodiments, the agent that inhibits TIM-3 is a TIM-3 binding agent. In some embodiments, the TIM-3 binding agent is an antibody, an antibody conjugate, or an antigen-binding fragment thereof. In some embodiments, the TIM-3 binding agent is MBG453, LY3321367, Sym023, TSR-022 or a derivative thereof. In some embodiments, the TIM-3 binding agent is TSR-022 or a derivative thereof. In some embodiments, the agent that inhibits TIM-3 is administered to the patient at a flat dose of about 100 mg, about 300 mg, about 500 mg, about 900 mg, or about 1200 mg or a weight-based dose of about 1 mg/kg, about 3 mg/kg, or about 10 mg/kg. In some embodiments, the agent that inhibits TIM-3 is administered to the patient at a flat dose of about 900 mg. In some embodiments, the agent that inhibits TIM-3 is administered to the patient once every three weeks.

In some embodiments, the immune checkpoint inhibitor is an agent that inhibits LAG-3. In some embodiments, the agent that inhibits LAG-3 is a small molecule, a nucleic acid, a polypeptide, a carbohydrate, a lipid, a metal, a toxin or a LAG-3 binding agent. In some embodiments, the agent that inhibits LAG-3 is a LAG-3 binding agent. In some embodiments, the LAG-3 binding agent is an antibody, an antibody conjugate, or an antigen-binding fragment thereof. In some embodiments, the LAG-3 binding agent is TSR-033, IMP321, relatlimab (BMS-986016), BI 754111, GSK2831781 (IMP-731), Novartis LAG525 (IMP701), REGN3767, MK-4280, MGD-013, GSK-2831781, FS-118, XmAb22841, INCAGN-2385, FS-18, ENUM-006, AVA-017, AM-0003, Avacta PD-L1/LAG-3 bispecific affamer, iOnctura anti-LAG-3 antibody, Arcus anti-LAG-3 antibody, Sym022 or a derivative thereof. In some embodiments, the LAG-3 binding agent is TSR-033 or a derivative thereof.

In some embodiments, the immune checkpoint inhibitor is administered intravenously.

In some embodiments, the method comprises administering one, two, or three immune checkpoint inhibitors.

In some embodiments, the cancer is adenocarcinoma, endometrial cancer, breast cancer, ovarian cancer, cervical cancer, fallopian tube cancer, testicular cancer, primary peritoneal cancer, colon cancer, colorectal cancer, gastric cancer, stomach cancer, small intestine cancer, squamous cell carcinoma of the anus, squamous cell carcinoma of the penis, squamous cell carcinoma of the cervix, squamous cell carcinoma of the vagina, squamous cell carcinoma of the vulva, soft tissue sarcoma, melanoma, renal cell carcinoma, lung cancer, non-small cell lung cancer, adenocarcinoma of the lung, squamous cell carcinoma of the lung, bladder cancer, gall bladder cancer, liver cancer, thyroid cancer, laryngeal cancer, salivary gland cancer, esophageal cancer, head and neck cancer, squamous cell carcinoma of the head and neck, prostate cancer, pancreatic cancer, mesothelioma, Merkel cell carcinoma, sarcoma, glioblastoma, a hematological cancer, multiple myeloma, B-cell lymphoma, T-cell lymphoma, Hodgkin's lymphoma/primary mediastinal B-cell lymphoma, chronic myelogenous leukemia, acute myeloid leukemia, acute lymphoblastic leukemia, non-Hodgkin's lymphoma, neuroblastoma, a CNS tumor, diffuse intrinsic pontine glioma (DIPG), Ewing's sarcoma, embryonal rhabdomyosarcoma, osteosarcoma, or Wilms tumor.

In some embodiments, the patient has previously been treated with one or more cancer treatment modalities. In some embodiments, the patient has previously been treated with one or more of surgery, radiotherapy, chemotherapy, or immunotherapy.

In some embodiments, the patient has previously received immunotherapy. In some embodiments, the patient has previously received an anti-PD-1 therapy. In some embodiments, the patient is relapsed or refractory.

In some embodiments, the patient has not previously received immunotherapy.

The present invention also provides a method performed by a data processing system for identifying a cancer as homologous recombination deficient or homologous recombination proficient, comprising: inputting image data corresponding to the cancer into the data processing system; accessing a computer program that includes a learning model with a function that associates the inputted image data with a homologous recombination deficiency status; executing the computer program with the function to process the inputted image data to identify image data features; based on the identified image data features determining a homologous recombination deficiency status for the inputted image data; and storing, in memory, a data structure with fields representing the inputted image data and its homologous recombination deficiency status. The image data features may comprise any one or more of pixels, pixel patterns, pixel-level data features and pixel-level data feature patterns. This method may be implemented on a local device or system or on a data communications network (i.e. the data processing system may be on a remote server, such a cloud server).

In embodiments, there is a user access device; and a server device configured for communication with the user access device over a network, the server device including the one or more data processors and the one or more memory stores (e.g. machine readable hardware storage devices). The memory stores store instructions that are executable by the one or more processors to perform the operations for identifying or determining the HR/HRD status of the cancer from its image. The instructions may be for the learning model (including any function) and any image-processor or other control software or computer program. The instructions may also produce the output. The server device could be comprised in a server farm or other distributed set of server devices, and the server device may be (wholly or in part) in a different country from where a user access the server (e.g. inputs an image), e.g. through the user access device (which may include a (graphical) user interface).

The present invention further provides computer program products and computer-readable storage media as set forth in the appended claims. These may be non-transitory. In other embodiments, there is provided other computer program products and computer-readable storage media with instructions which, when executed by a computer or one or more data processors, implement any other steps of the methods disclosed herein, including without limitation steps for the identification of labels for unlabeled images, including any or all elements of consensus labelling disclosed herein (including as disclosed in the Examples, e.g. Example 2).

In embodiments of the present invention, for its various aspects, there is included a user interface, for instance a graphical user interface, to enable a user to input image/image data and/or to receive the output of the method/system etc. The user interface may be implemented as an application on a personal computer device, including desktops, laptops, tablets, smartphones and the like or into a system or device into which the invention is incorporated or implemented, for instance a imaging system/apparatus for capturing the cancer image, such as a slide scanner. The user interface may also be accessed over a data communications network, such as the internet and/or a cellular mobile data network. The user interface may be in the form of a website page, which may be a public or private website page.

The present invention also provides any and all combinations of (i) different aspects, (ii) any aspect (or combination of aspects) with any one or more embodiments of any aspect(s), (iii) one or more embodiments of any aspect with one or more embodiments of any other aspect or aspects, and (iv) embodiments of any given aspect, and (v) any combination of (i)-(iv) above. In particular, it will be appreciated that various aspects and embodiments concern the same general inventive concept, albeit expressed from a different perspective and/or with different terminology for the same features. The combining of such aspects and embodiments, with suitable rationalization, is hereby expressly and clearly contemplated.

DETAILED DESCRIPTION OF THE INVENTION

Described herein are methods of characterizing a cancer status or type, such as homologous recombination deficiency status of a cancer (e.g., identifying the cancer as homologous recombination deficient or homologous recombination proficient), as well as systems and devices for performing such methods. Also provided are methods of treating a homologous recombination deficient cancer in a patient, wherein the cancer has been identified using a described characterization method.

It has been found that cancer images (for example, cancer tissue samples stained using hematoxylin and eosin stain and imaged) can used to reliably characterize the cancer as being homologous recombination deficient or homologous recombination proficient. Cancer images are often obtained for histopathological analysis of a cancer, and the described methods can provide a deeper analysis of such images to more effectively treat the cancer, for example by treating the cancer with drugs that are effective against homologous recombination deficient cancer.

The characterization and/or identification method uses a (trained) learning model (which may be a deep learning model, such as a convolution neural network) to associate image data associated with the cancer (of a subject, in particular a living human) to a homologous recombination deficiency (HRD) status of the cancer. The outputted HRD status may be or may be indicative of a likelihood that the cancer is homologous recombination deficient or homologous recombination proficient, or may be a binary determination that identifies the cancer as homologous recombination deficient or homologous recombination proficient. Therefore, based on the output of the learning model, the cancer can be characterized and/or identified as HRD or HRP.

The learning model is trained based on training image data, which includes a first set of cancer image data labeled as homologous recombination deficient, and a second set of cancer image data labeled as homologous recombination proficient. A homologous recombination classifier comprising weighted features can be used to determine an HRD likelihood of the cancers associated with the training data, and a likelihood threshold cutoff can be used to label the training cancer as homologous recombination deficient or homologous recombination proficient. The HRD classifier includes weighted features associated with homologous recombination deficiency, such as a mutational signature score and/or a large-scale state transition (LST) score.

A cancer that is identified as homologous recombination deficient can be treated using an anti-cancer agent effective against an HRD cancer, such as a PARP inhibitor. Therefore, using the methods disclosed herein, the cancer can be effectively treated using an effective anti-cancer agent without delay that might otherwise occur.

Figure 8:
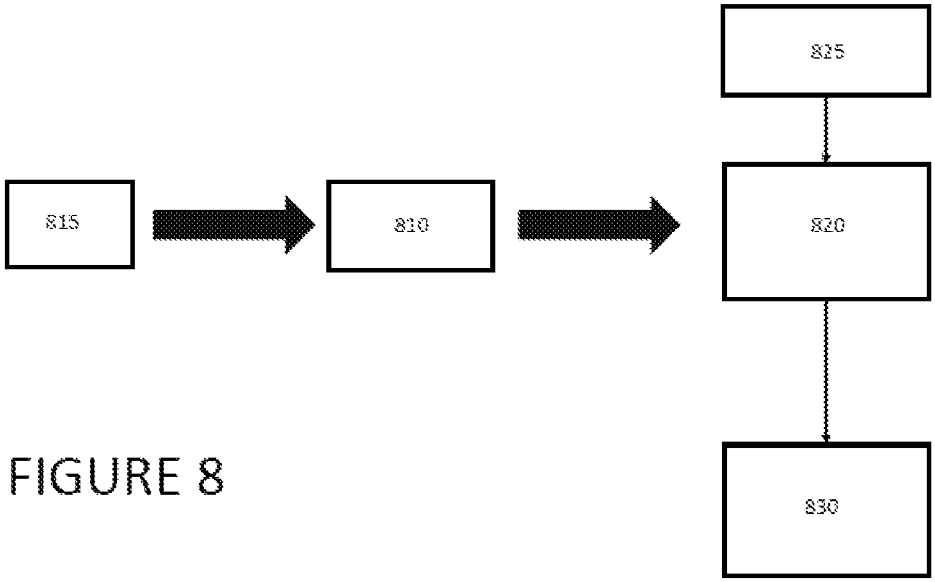
FIG. 8 is a schematic flow diagram of building and deploying a machine learning model for use with a certain form of data (task data) through use of supervised learning.

FIG. 8 shows the basic approach for training a machine learning model, as may be used in the present invention and as used in some of the Examples hereinbelow. It involves selecting a suitable machine learning (ML) model 810 for the task, such as those outlined herein for use with the invention, and training that model by inputting to it training data 815. The training data 815 comprises an initial training set which is used to train the model 810 and a hold-out set used to fine-tune the trained model and/or to test the trained model. The final, accurately-trained model 820 resulting from the training is then deployed to receive new data 825 and provide as output 830 a prediction based on the new data (e.g. which of a set of classes the new data 830 belongs to, based on the model being trained with training data representative of the new data and each training data element labelled with the appropriate class it belongs to).

Figure 9:
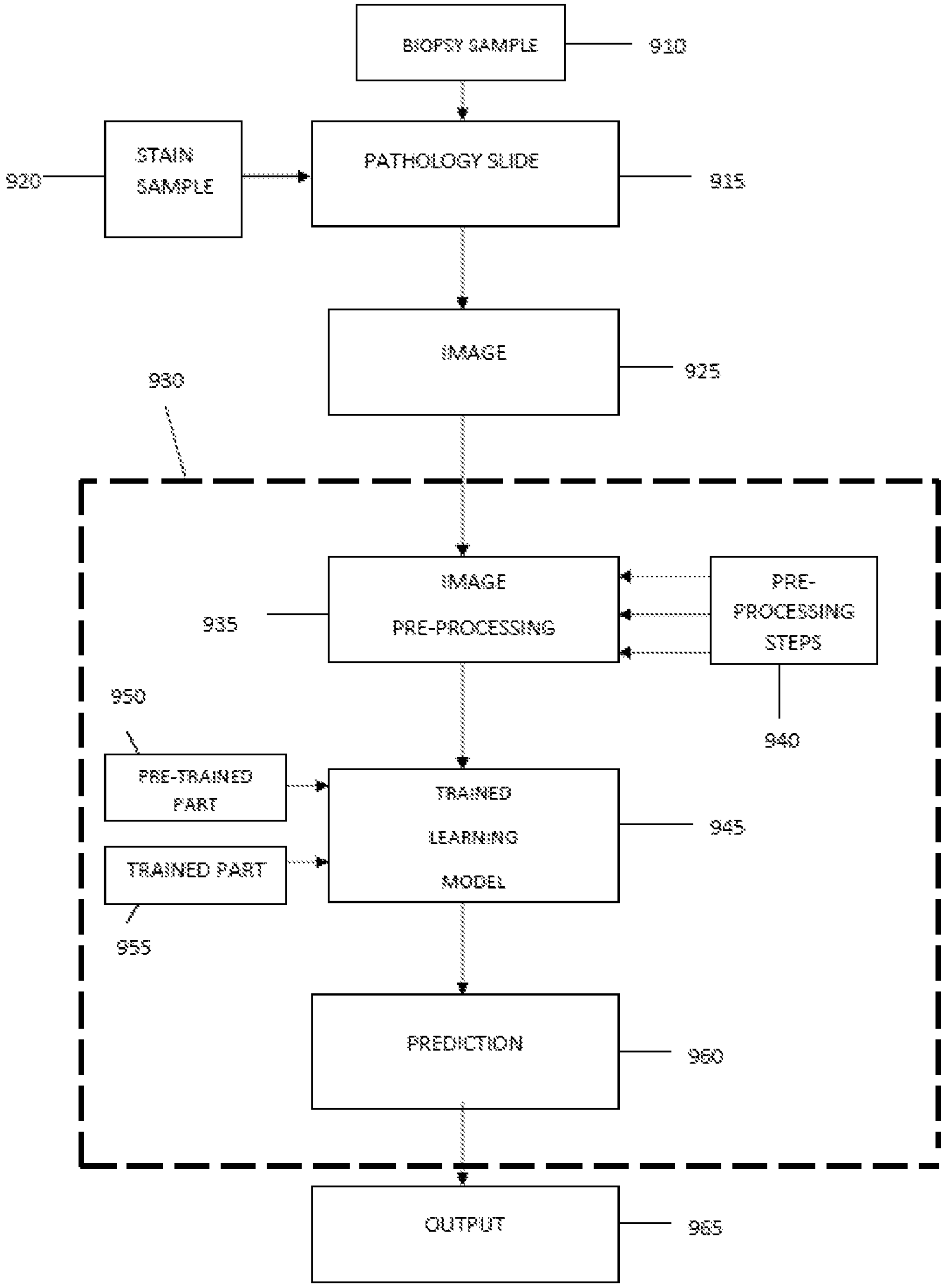
FIG. 9 illustrates a method and system for predicting or diagnosing the HR (e.g. HRD) status of a cancer from an image of the cancer in accordance with certain aspects and embodiments of the present invention.

FIG. 9 illustrates a method and system in accordance with an embodiment of the invention for predicting or diagnosing the HR (e.g. HRD) status (or microsatellite (in)stability or tumor mutation burden) of a cancer from an image of the cancer. This embodiment also includes other aspects, embodiments and features of the invention.

As shown, a biopsy of a cancer is taken at step 910 and then sectioned and mounted to a microscope slide (step 915) in a manner known in the art, and as may be described elsewhere herein. This forms a histology or histopathology slide. The cancer sample on the slide is stained (step 920), preferably (but not necessarily) with hematoxylin and eosin (H&E), again following standard clinical practice. An image (typically digital) of the slide (e.g. a whole slide image (WSI)) is then taken at step 925, such as with a slide scanner or other imaging system as described elsewhere herein. The image (or more accurately, data representing the image ('image data')) 925 is input to an image analyzer (or image analysis system) 930 in accordance with at least one aspect or at least one embodiment of the present invention.

The image analyzer 930 comprises an image pre-processor 935 to carry out certain pre-processing steps 940 on the image data 925, such as disclosed elsewhere herein. The image data resulting from the pre-processing step is input to a trained machine learning (ML) model 945. The trained ML model 945 may result from being trained with training data as described herein (such as by consensus labelling, e.g. in accordance with Example 2) or as otherwise known in the art. As also described elsewhere herein, the ML model 945 is trained by transfer learning using a pre-trained ML model (such as pre-trained on the ImageNet image dataset), so the trained ML model 945 comprises a pre-trained 950 and (re-)trained part 955, again as is known in the art. Alternatively, the trained ML model 945 is trained from scratch (all of the model weights—not just those in the final layer(s)/head) are randomized and learnt from the training data).

The trained ML model 945 at step 960 produces a prediction or diagnosis of the HR (e.g. HRD) status (or microsatellite (in)stability or tumor mutation burden) of the cancer from the image data. At step 965 an output is produced based on the prediction or diagnosis. This may be in the form of a document (e.g. report or email) or data in a form which represents such a document.

The image analyzer 930 may be standalone device or be hosted in a communication network (at a node of communication network and/or hosted on a cloud platform) or form part of (be embedded, incorporated or integrated in) a system or apparatus/equipment which comprises an imaging system for producing the image, for instance a slide scanner. The image analyzer 930 may be used for telepathology or telemedicine.

As will be understood, the image analyzer 930 is computer-controlled or computer-implemented and comprises one or more data memories for storing the image data (including as pre-processed), trained ML model and image pre-processor and one or data processors for processing the image data with the image pre-processor and trained ML model and providing the output. It will further be understood the image data and output can have the form of a data structure as described elsewhere herein. It will also be understood the image 925 can be processed as image portions (e.g. tiles), as also described herein. The analysis of the input image 925 by the image analyzer is automatic; i.e. the output 956 is provided automatically.

The image analyzer 930 can be modified to include other features or methodologies (as additions or alternatives) as disclosed herein.

Definitions

As used herein, the singular forms "a," "an," and "the" include the plural references unless the context clearly dictates otherwise.

Reference to "about" a value or parameter herein includes (and describes) variations that are directed to that value or parameter per se. For example, description referring to "about X" includes description of "X".

As used herein, the term "administration" typically refers to the administration of a composition to a subject or system. Those of ordinary skill in the art will be aware of a variety of routes that may, in appropriate circumstances, be utilized for administration to a subject, for example a human subject. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Those skilled in the art are well familiar with antibody structure and sequence elements, recognize "variable" and "constant" regions in provided sequences, and understand that there may be some flexibility in definition of a "boundary" between such domains such that different presentations of the same antibody chain sequence may, for example, indicate such a boundary at a location that is shifted one or a few residues relative to a different presentation of the same antibody chain sequence. Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc., as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]

As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc., as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.], or other pendant group [e.g., poly-ethylene glycol, etc.]. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

As used herein, the term "combination therapy" refers to a clinical intervention in which a subject is simultaneously exposed to two or more therapeutic regimens (e.g., two or more therapeutic agents). In some embodiments, the two or more therapeutic regimens may be administered simultaneously. In some embodiments, the two or more therapeutic regimens may be administered sequentially (e.g., a first regimen administered prior to administration of any doses of a second regimen). In some embodiments, the two or more therapeutic regimens are administered in overlapping dosing regimens. In some embodiments, administration of combination therapy may involve administration of one or more therapeutic agents or modalities to a subject receiving the other agent(s) or modality. In some embodiments, combination therapy does not necessarily require that individual agents be administered together in a single composition (or even necessarily at the same time). In some embodiments, two or more therapeutic agents or modalities of a combination therapy are administered to a subject separately, e.g., in separate compositions, via separate administration routes (e.g., one agent orally and another agent intravenously), and/or at different time points. In some embodiments, two or more therapeutic agents may be administered together in a combination composition, or even in a combination compound (e.g., as part of a single chemical complex or covalent entity), via the same administration route, and/or at the same time.

As used herein, the terms "chemotherapeutic agent" and "anti-cancer agent" refer to a chemical agent that inhibits the proliferation, growth, life-span and/or metastatic activity of cancer cells. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines (e.g., altretamine, triethylenemelamine, trietylenephosphoramide, triethiylenethiophosphoramide and trimethylolomelamine); acetogenins; delta-9-tetrahydrocannabinol (e.g., dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; xeloda; ibandronate; topoisomerase inhibitor RFS 2000; difluoromethylornithine (DMFO); retinoids such as retinoic acid; capecitabine; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin. Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above. Also included in this definition are "antimetabolite chemotherapeutic agents" that are structurally similar to a metabolite, but cannot be used by the body in a productive manner. Many antimetabolite chemotherapeutic agents interfere with the production of the nucleic acids, RNA and DNA. Examples of antimetabolite chemotherapeutic agents include gemcitabine (GEMZAR®), 5-fluorouracil (5-FU), capecitabine (XELODA™), 6-mercaptopurine, methotrexate, 6-thioguanine, pemetrexed, raltitrexed, arabinosylcytosine ARA-C cytarabine (CYTOSAR-U®), dacarbazine (DTIC-DOMED), azocytosine, deoxycytosine, pyridmidene, fludarabine (FLUDARA®), cladrabine, 2-deoxy-D-glucose etc. In some embodiments, an antimetabolite chemotherapeutic agent is gemcitabine. Gemcitabine HCl is sold by Eli Lilly under the trademark GEMZAR®. Also included in this definition are "platinum-based chemotherapeutic agents" that comprises an organic compound which contains platinum as an integral part of the molecule. In some embodiments, a chemotherapeutic agent is a platinum agent. In some such embodiments, the platinum agent is selected from cisplatin, carboplatin, oxaliplatin, nedaplatin, triplatin tetranitrate, phenanthriplatin, picoplatin, or satraplatin.

As used herein, the terms "dosage form" or "unit dosage form" refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a regimen that has been determined to correlate with a desired or beneficial outcome when administered to a relevant population (e.g., with a therapeutic regimen). Those of ordinary skill in the art appreciate that the total amount of a therapeutic composition or agent administered to a particular subject is determined by one or more attending physicians and may involve administration of multiple dosage forms.

The term "effective amount" used herein refers to an amount of a compound or composition sufficient to treat a specified disorder, condition, or disease, such as ameliorate, palliate, lessen, and/or delay one or more of its symptoms. In reference to a disease such as a cancer, an effective amount comprises an amount sufficient to cause a tumor to shrink and/or to decrease the growth rate of the tumor (such as to suppress tumor growth) or to prevent or delay other unwanted cell proliferation in the cancer. In some embodiments, the effective amount is an amount sufficient to delay development of a cancer. In some embodiments, the effective amount is an amount sufficient to prevent or delay recurrence. An effective amount can be administered in one or more administrations. In the case of a cancer, the effective amount of the drug or composition may: (i) reduce the number of epithelioid cells; (ii) reduce tumor size; (iii) inhibit, retard, slow to some extent and optionally stop the cancer cells infiltration into peripheral organs; (iv) inhibit (e.g., slow to some extent and optionally stop) tumor metastasis; (v) inhibit tumor growth; (vi) prevent or delay occurrence and/or recurrence of tumor; and/or (vii) relieve to some extent one or more of the symptoms associated with the cancer.

As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution. As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Representative algorithms and computer programs useful in determining the percent homology between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent homology between two nucleotide sequences can, alternatively, be determined for example using the GAP program in the GCG software package using an NWSgapdna.CMP matrix.

The terms "individual," "patient," and "subject" are used synonymously, and refer to a mammal.

As used herein, the term "pharmaceutically acceptable salt" refers to those compounds (including salts) which are, within the scope of sound medical judgment, suitable for use in contact with the tissues of humans being and lower animals without undue or excessive toxicity, irritation, allergic response, or other problem or complication, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^{+}(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant likelihood of achieving a predetermined therapeutic effect when administered to a relevant population. In some embodiments, a pharmaceutical composition may be specially formulated for administration in solid or liquid form, including those adapted for oral administration, for example, drenches (aqueous or non-aqueous solutions or suspensions), tablets, e.g., those targeted for buccal, sublingual, and systemic absorption, boluses, powders, granules, and pastes for application to the tongue. A pharmaceutical composition can also refer to a medicament.

As used herein, the term "regimen" refers to a set of unit doses (typically more than one) that are administered individually to a subject, typically separated by one or more periods of time. In some embodiments, a given therapeutic agent is administered according to a regimen, which may involve one or more doses. In some embodiments, a regimen comprises a plurality of doses each of which is separated in time from other doses. In some embodiments, individual doses are separated from one another by a time period of the same length; in some embodiments, a regimen comprises a plurality of doses, wherein the doses are separated by time periods of different length. In some embodiments, a regimen comprises doses of the same amount. In some embodiments, a regimen comprises doses of different amounts. In some embodiments, a regimen comprises at least one dose, wherein the dose comprises one unit dose of the therapeutic agent. In some embodiments, a regimen comprises at least one dose, wherein the dose comprises two or more unit doses of the therapeutic agent.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from a disease, diminishing the extent of a disease, stabilizing a disease (e.g., preventing or delaying the worsening of the disease), preventing or delaying the spread (e.g., metastasis) of a disease, preventing or delaying the recurrence of a disease, delaying or slowing the progression of a disease, ameliorating a disease state, providing remission (partial or total) of a disease, decreasing the dose of one or more other medications required to treat a disease, delaying the progression of a disease, increasing the quality of life, and/or prolonging survival. Also encompassed by "treatment" is a reduction of a pathological consequence of a disease (such as cancer). The methods of the invention contemplate any one or more of these aspects of treatment.

It is understood that aspects and variations of the invention described herein include "consisting" and/or "consisting essentially of" aspects and variations.

When a range of values is provided, it is to be understood that each intervening value between the upper and lower limit of that range, and any other stated or intervening value in that states range, is encompassed within the scope of the present disclosure. Where the stated range includes upper or lower limits, ranges excluding either of those included limits are also included in the present disclosure.

The section headings used herein are for organization purposes only and are not to be construed as limiting the subject matter described. The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

The disclosures of all publications, patents, and patent applications referred to herein are each hereby incorporated by reference in their entireties. To the extent that any reference incorporated by reference conflicts with the instant disclosure, the instant disclosure shall control.

Cancer Tissue Samples and Images

Using the methods described herein, a cancer can be characterized to determine a homologous recombination deficiency status of the cancer (such as identifying the cancer as homologous recombination deficient or homologous recombination proficient, or a likelihood that the cancer is homologous recombination deficient or homologous recombination proficient) using image data associated with the cancer. In some embodiments, the cancer is a solid cancer, such as a breast cancer or ovarian cancer. In some embodiments, the cancer is a liquid cancer (e.g., a leukemia).

Images can be obtained from a tissue sample (human biological sample), such as a sectional sample (for example, obtained through a surgical excision) or a needle biopsy sample. In some embodiments, for example when the cancer is a liquid cancer, the tissue sample is obtained through a blood drawn. The tissue sample is taken from a cancer or suspected cancer. In some embodiments, the cancer tissue sample is taken from an excisional biopsy or a core biopsy. The individual from which the tissue sample is tissue sample is taken is a mammal, and optionally a human Nevertheless, the individual may be any type of mammal, such as but not limited to, human, bovine, horse, feline, canine, rodent, or primate animals. In some embodiments, the individual is a human. In some embodiments, the human is male. In some embodiments, the human is female.

In some embodiments, the tissue sample is processed before imaging, such as by staining the sample and/or preserving the sample. The cancer tissue sample may be preserved, for example, by one or more of dehydrating the sample, fixing the sample, freezing the sample, and/or embedding the sample, among others methods. The cancer tissue may be stained, for example, using hematoxylin and eosin (H&E) staining or other histopathology sample stains (e.g., toluidine blue, Masson's trichrome stain, Mallory's trichrome stain, Weigert's elastic stain, Heidenhain's AZAN trichrome stain, silver stain, Wright's stain, Orcein stain, or periodic acid-Schiff stain). Methods of fixing the cancer tissue sample can include the use of formaldehyde, glutaraldehyde, or other suitable chemical fixing agent. In some embodiments, the sample is frozen, for example using a cryostat or other suitable equipment. In some embodiments, processing of the cancer tissue sample can include embedding, for example through the use of a resin (such as an epoxy or acrylic resin), a wax (such as paraffin wax), agar, gelatin, or other suitable material. In some embodiments, the cancer tissue samples are formalin-fixed, paraffin-embedded (FFPE) tissue samples. In some embodiments, the cancer tissue samples are thinly sliced before being imaged. In some embodiments, the cancer tissue samples have a thickness of about 20 μm or less (such as about 15 μm or less, about 10 μm or less, about 8 μm or less, about 6 μm or less, about 5 μm or less, about 4 μm or less, about 3 μm or less, or about 2 μm or less. In some embodiments, the cancer tissue samples have a thickness of about 1 μm or more, such as about 2 μm or more, about 3 μm or more, about 4 μm or more, about 5 μm or more, about 6 μm or more, about 8 μm or more, or about 10 μm or more.

Images of the cancer tissue samples can be captured using a camera, such as a digital camera or optical camera. However, optical images are generally digitized to allow for analysis and characterization of the cancer. A microscope may be used to enhance the image of the cancer, which may provide an optical zoom greater than 1× (e.g., about 1× to about 1000×, such as about 1.5× to about 800×, about 2× to about 600, about 3× to about 500×, about 4× to about 400, about 5× to about 300×, about 10× to about 250×, about 15× to about 200×, about 20× to about 150×, or about 50× to about 100×, or any number therebetween). The microscope may be configured for serial magnification, for example a 10× magnification component (e.g., as may be found on a microscope eyepiece) in combination with a 20× magnification component for a combined 200× magnification.

In addition to or instead of the optical magnification, the image may be digitally magnified. In some embodiments, the image is digitally magnified by a factor of more than 1×, such as about 1.5× or more, about 2× or more, about 3× or more, about 4× or more, about 5× or more, about 6× or more, about 8× or more, about 10× or more, about 15× or more, about 20× or more, or about 30× or more. In some embodiments, the image is digitally magnified by a factor of less than about 50×, less than about 30×, less than about 20×, less than about 15×, less than about 10×, less than about 8×, less than about 6×, less than about 5×, less than about 4×, less than about 3×, less than about 2×, or less than about 1.5×.

In some embodiments, an image is divided into a plurality of tiles. In some embodiments, the tiles are about 128×128 pixel tiles, about 256×256 pixel tiles, about 512×512 pixel tiles, about 1028×1028 pixel tiles, about 2048×2048 pixel tiles, or 4096×4096 pixel tiles. The number of tiles corresponding to a given image may depend on the size of the image. In some embodiments, the image is divided into about 50 or more (e.g., about 100 or more, about 150 or more, about 200 or more, about 250 or more, about 300 or more, about 400 or more, about 500 or more, about 600 or more, about 700 or more, about 800 or more, about 900 or more, or about 1000 or more tiles). In some embodiments, the image is divided into about 50 to about 2000 tiles (such as one or more of about 50 to about 100 tiles, about 100 to about 150 tiles, about 150 to about 200 tiles, about 200 to about 250 tiles, about 250 to about 300 tiles, about 300 to about 400 tiles, about 400 to about 500 tiles, about 500 to about 600 tiles, about 600 to about 700 tiles, about 700 to about 800 tiles, about 800 to about 900 tiles, about 900 to about 1000 tiles, about 1000 to about 1500 tiles, or about 1500 to about 2000 tiles). In some embodiments the image data comprises non-overlapping tiles. In some embodiments, the image data comprises overlapping tiles, or a mixture of overlapping tiles and non-overlapping tiles. In some embodiments, the tiles are uniformly sized (i.e., the same number of pixels per tile). In some embodiments, the tiles may contain over 100,000 pixels per tile (e.g., over 200,000 pixels per tile, over 500,000 pixels per tile, over 1,000,000 pixels per tile, over 5,000,000 pixels per tile, over 10,000,000 pixels per tile, or over 15,000,000 pixels per tile). In some embodiments, the images have between 100,000 pixels per tile and 1,000,000 pixels per tile. The tiles need not be square, and can be of any shape (e.g., triangular, quadrangle (e.g., rectangular, rhomboid, etc.), pentagonal, hexagonal, heptagonal, octagonal, etc.).

Optionally, the image data is filtered to remove tiles with background noise above a predetermined threshold. The tiles may be filtered, for example, if more than about 30%, more than about 40%, more than about 50%, more than about 60%, or more than about 70% of the pixels in a given tile are attributable to background signal.

The image data derived corresponding to an image of a cancer may be used as test image data (i.e., image data inputted in a trained learning model for the purpose of characterizing the cancer associated with the inputted image data), or as training and/or validation image data.

Non-limiting examples of cancers to be characterized or treated by the methods of the present disclosure can include melanoma (e.g., metastatic malignant melanoma), renal cancer (e.g., clear cell carcinoma), prostate cancer (e.g., hormone refractory prostate adenocarcinoma), pancreatic adenocarcinoma, breast cancer (e.g., HER2+ breast cancer, HER2− breast cancer, luminal A breast cancer, luminal B breast cancer, triple-negative breast cancer, or other breast cancer subtypes), colon cancer, lung cancer (e.g., non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies, hematological cancer, multiple myeloma, B-cell lymphoma, T-cell lymphoma, Hodgkin's lymphoma/primary mediastinal B-cell lymphoma, chronic myelogenous leukemia, acute myeloid leukemia, acute lymphoblastic leukemia, non-Hodgkin's lymphoma, neuroblastoma. Additionally, the invention includes refractory or recurrent malignancies whose growth may be inhibited using the methods of the invention. In some embodiments, a cancer to be treated by the methods of the present disclosure include, for example, carcinoma, squamous carcinoma (for example, cervical canal, eyelid, tunica conjunctiva, vagina, lung, oral cavity, skin, urinary bladder, tongue, larynx, and gullet), and adenocarcinoma (for example, prostate, small intestine, endometrium, cervical canal, large intestine, lung, pancreas, gullet, intestinum rectum, uterus, stomach, mammary gland, and ovary). In some embodiments, a cancer to be treated by the methods of the present disclosure further include sarcomata (for example, myogenic sarcoma), leukosis, neuroma, melanoma, and lymphoma.

Classification and Training Methods

Various types of classification and learning models may be used to implement the techniques described herein. These various types of classification and learning models include machine learning models, deep learning models, neural networks and so forth. As described herein, these learning models receive data as input and output data representing a classification, label or other indication of assignment. This input data can be in the form of a data structure (e.g., a vector of inputs, with each input being one or more data items, for example data relating to image pixels), structured data (e.g., image data—data representing an image) and so forth. The output data may also be in the form of a data structure, structured data or a data item.

A trained learning model configured to characterize a homologous recombination deficiency status of a cancer receives, as input, image data corresponding to the cancer, and associates the image data to a recombination deficiency status using a function (e.g., a classification function). This may also be thought of as the function identifying whether the image data represents a particular HRD status or which HRD status it represents, for instance if the image data represents a cancer that is HRD or HRP. In some embodiments, the trained learning model identifies the cancer as homologous recombination deficient or homologous recombination proficient. In some embodiments, the trained learning model determines a likelihood that the cancer is homologous recombination deficient or homologous recombination proficient.

In some embodiments, a homologous recombination deficient status of the cancer associated with a likelihood that the cancer is homologous recombination deficient or homologous recombination proficient is used to identify the cancer as homologous recombination deficient or homologous recombination proficient. In some embodiments, a threshold cutoff of the likelihood is used to classify the cancer in a binary manner. For example, in some embodiments if the cancer is about 50% or more, about 60% or more, about 70% or more, about 75% or more, about 80% or more, about 85% or more, about 87.5% or more, about 90% or more, about 92.5% or more, about 95% or more, or about 97.5% or more likely to be homologous recombination deficient, then the cancer is identified as homologous recombination deficient. In some embodiments if the cancer is about 50% or more, about 60% or more, about 70% or more, about 75% or more, about 80% or more, about 85% or more, about 87.5% or more, about 90% or more, about 92.5% or more, about 95% or more, or about 97.5% or more likely to be homologous recombination proficient, then the cancer is identified as homologous recombination proficient. In some embodiments, if the cancer is about 50% or less, about 40% or less, about 30% or less, about 25% or less, about 20% or less, about 15% or less, about 12.5% or less, about 10% or less, about 7.5% or less, about 5% or less, or about 2.5% or less likely to be homologous recombination deficient, then the cancer is identified as homologous recombination proficient. In some embodiments, if the cancer is about 50% or less, about 40% or less, about 30% or less, about 25% or less, about 20% or less, about 15% or less, about 12.5% or less, about 10% or less, about 7.5% or less, about 5% or less, or about 2.5% or less likely to be homologous recombination proficient, then the cancer is identified as homologous recombination deficient.

The homologous recombination deficiency status of a cancer may be based on the image data as a whole, or on an average (or, optionally, a weighted average) of tiles within the image data. The average may be a mean or a median. For example, in some embodiments, the trained machine learning model outputs a homologous recombination deficiency status (either a likelihood or a binary status determination) for each analyzed tile in the image data, and the recombination deficiency status of the cancer associated with the image is an average of the homologous recombination deficiency status of the tiles. In some embodiments, the average homologous recombination deficiency status is weighted to bias certain tiles within the image data using a weighting parameter. The weighting parameter may be based one, for example, the amount of noise present in any given tile.

In some embodiments, the learning model is a deep learning model, such as a convoluted neural network (CNN) or other suitable image classification model. An exemplary deep learning model that may be used is the Inception (e.g., Inception v3) image classification model. See Szegedy et al., Going Deeper with Convolutions, in The IEEE Conference of Computer Vision and Pattern Recognition, pp. 1-9 (Boston, 2015). In some embodiments, the learning model is pre-trained before being trained with the training image data. The learning model can be pre-trained, for example, using pre-training image data comprising image data not associated with cancer images (for example, images available from ImageNet) and/or pre-training image data comprising image data associated with cancer images, although not necessarily labeled as homologous recombination deficient or homologous recombination proficient. For example, the pre-training image data may include image data corresponding to cancer images of different cancer types (e.g., breast, cervical, lung, etc.) and labeled accordingly. In some embodiments, the learning model may be pre-trained using multiple rounds, for example a first pre-training round using pre-training image data comprising image data not associated with cancer images and a second pre-training round using pre-training image data comprising image data associated with cancer images. In some embodiments, the first pre-training round using pre-training image data comprising image data not associated with cancer images precedes the second pre-training round using pre-training image data comprising image data associated with cancer images.

The trained learning model is trained based on training image data labeled with a homologous recombination status. For example, the training image data can include a first set of training image data labeled as homologous recombination proficient and a second set of training image data labeled as homologous recombination deficient. The training image data within each labeled set includes a plurality of images, and the images are optionally divided into tiles, as described above. In some embodiments the images of the training image data are labeled in a binary manner (i.e., each labeled as homologous recombination deficient or homologous recombination proficient). In some embodiments, the images of the training image data are labeled with a likelihood (e.g. probability) that the image is homologous recombination deficient or a likelihood that the image is homologous recombination proficient. In some embodiments, the images of the training image data are divided into tiles, and all tiles within an image are uniformly labeled as homologous recombination proficient or homologous recombination deficient. In some embodiments, the images of the training image data are divided into tiles, and the tiles are independently labeled with a homologous recombination deficiency status (either binary (HRD or HRP) or a likelihood).

The training image data (either the images as a whole or individual tiles within the image) can be labeled for homologous recombination deficiency status (e.g., as homologous recombination deficient or homologous recombination proficient, or a likelihood of being homologous recombination deficient or homologous recombination proficient) using one or more features associated with homologous recombination deficiency. Such features may include, for example, one or more of a mutational signature score associated with the cancer, a telomeric allelic imbalance score, a large-scale state transition (LST) score associated with the cancer, a loss of heterozygosity (LOH) score, a fraction of the genome having lost heterogeneity (fLOH), or a homologous recombination deficiency score (the sum of one or more of the telomeric allelic imbalance (NtAI) score, the large-scale state transition (LST) score, fraction of genome having lost heterogeneity (fLOH), and/or the loss of heterozygosity (LOH) score). In some embodiments, the homologous recombination deficiency (HRD) score is a sum of NtAI, LST, and LOH. In some embodiments, for example, the one or more features include a mutational signature score (e.g., a signature 3 score) and a large-scale state transition score.

Nucleic acids from a cancer sample can be sequenced to characterize a mutational signature for the cancer. The mutational signature may be determined from a whole-genome sequencing of the cancer genome or a portion of (and optionally an untargeted portion of) the whole genome (for example, a whole exome sequencing). The mutational signature from the cancer can be scored for likeness to a predetermined mutational signature. Signature 3 is a mutational signature associated with homologous recombination deficiency. Signature 3, and other mutational signatures, are further described in Alexandrov et al., *Signatures of mutational process in human cancer*, Nature, vol. 500, no. 7463, pp. 415-425 (2013); Davies et al., *HRDetect is a predictor of BRCA1 and BRCA2 deficiency based on mutational signatures*, Nature Medicine, vol. 23, pp. 512-525 (2017); and Polak et al., *A mutational signature reveals alterations underlying deficient homologous recombination repair in breast cancer*, Nature Genetics, vol. 49, pp. 1476-1486 (2017).

The Signature 3 scores used herein may be determined as known in the art, such as in the literature referenced herein. Alternatively, a new (composite) Signature 3 score may be used, which is determined as described hereinbelow in Example 1.

Certain genomic scars are associated with homologous recombination deficiency, such as a number of telomeric allelic imbalances (NtAI), largest-scale state transitions (LST), and loss of heterozygosity (HRD-LOH). See, for example, Marquard et al., *Pan-cancer analysis of genomic scar signatures associated with homologous recombination deficiency suggests novel indications for existing cancer drugs*, Biomarker Research, vol. 3, no. 9 (2015). The number of telomeric allelic imbalances (NtAI) score relates the number of subtelomeric regions with allelic imbalance that start from beyond the centromere and extend to the telomere. The largest-scale state transitions (LST) score relates to the number of large chromosomal breaks between adjacent regions, generally of at least about 10 megabases (Mb), although the specific threshold size may be increased or decreased. The loss of heterozygosity score (HRD-LOH) relates to the number of regions with a loss of heterozygosity, generally larger than 15 Mb (although the specific threshold size may be increased or decreased), but shorter than the whole chromosome. In some embodiments, the features may include one or more of NtAI, LST, LOH, or an HRD score (the sum of one or more of NtAI, LST and LOH). In some embodiments, the one or more features comprise LST. In some embodiments, the one or more features do not include NtAI. In some embodiments, the one or more features do not include LOH. In some embodiments, the one or more features do not include NtAI and LOH. In some embodiments, HRD score, NtAI score, LST score, and/or LOH score is determined by a microarray or by sequencing (for example, whole exome sequencing or whole genome sequencing) nucleic acids derived from the cancer. Fraction of the genome with a loss of heterogeneity (fLOH) is another genomic scar associated with homologous recombination deficiency that may be used as a feature. FLOH is described in Wang et al., *Profiles of Genomic Instability in High-Grade Serous Ovarian Cancer Predict Treatment Outcome*, Clinical Cancer Research, vol. 18, no. 20, pp. 5806-5815 (2012) and Swisher et al., *Pucaparib in relapsed, platinum-sensitive high-grade ovarian carcinoma* (*ARIEL Part* 1): *an international, multicentre, open-label, phase* 2 *trial*, Lancet, vol. 18 no. 1, pp. 75-81 (2016).

In some embodiments, to establish a ground truth for the training data, cancer samples with bi-allelic inactivation of one or more genes associated with homologous recombination deficiency (such as BRCA1, BRCA2, ATM, ATR, BAP1, BARD1, BLM, BRIP1, MRE11A, NBN, PALB2, RAD51, RAD51B, RAD51C, RAD51D, RAD52, RAD54L, or XRCC2) can be labeled as homologous recombination deficient. The bi-allelic inactivation may be observed, for example, through a silencing mutation, a deletion or partial deletion of the gene, or a silencing methylation pattern of the gene.

In some embodiments, training data ground truth for homologous recombination proficient (or 'not-HRD') can be based on one or more of having a BRCA1 and BRCA2 wild-type gene, a mutational signature score associated with the cancer, a telomeric allelic imbalance score, a large-scale state transition (LST) score associated with the cancer, a loss of heterozygosity score, a homologous recombination deficiency score (the sum of one or more of the telomeric allelic imbalance score, the large-scale state transition (LST) score and/or the loss of heterozygosity score), and/or a number of detected homologous recombination deficiency events. For example, in some embodiments, the ground truth for homologous recombination deficient training image data is based on the associated cancer having a mutational signature score (e.g., signature 3) at or below a threshold and/or a number of homologous recombination deficiency events (or a number of telomeric allelic imbalance, large-scale state transitions, and/or number of loss of heterozygosity score) at or below threshold. In some embodiments, the threshold is a predetermined threshold. See, for example, the description of the "MyChoice" diagnostic test of Myriad Genetics, Inc. earlier herein where the threshold is a test score (HRD score) of 42 for characterizing (or classifying) a cancer as HRD or HRP (not-HRD). In some embodiments, the threshold is determined using consensus labeling (as further discussed below).

In some embodiments, ground truth training data samples (that is, training data associated with a cancer defined as homologous recombination deficient and/or a cancer defined as homologous recombination proficient using a ground truth determination) can be used to associate the features associated with homologous recombination deficiency with a homologous recombination deficiency status using an association function. A vector may represent the features, with each data item in the vector representing a particular feature. For example, the features may be associated with homologous recombination deficiency status using a training data classification model, which may be for example a regression algorithm (such as a logistic regression algorithm, for example least absolute shrinkage and selection operator (LASSO) regression algorithm). The model (which may receive as input the afore-mentioned vector) can determine how to weight the features used to determine the homologous recombination deficiency status of the ground truth data to train the training data classification model. The trained training data classification model can then be used to characterize training data homologous recombination deficiency status for cancers with determined features. Thus, the training data classification model can be used to label cancers (with a label indicative of the cancer being HRD or HRP/not-HRD), and thus training image data associated with the cancer (i.e. data representing an image taken of the cancer to be labelled, such as described elsewhere herein), based on the homologous recombination deficiency status of the cancer. The labelled cancer images may then be used as a training set (in turn divided into training and test (optionally validation) sub-sets) of image data for training a learning model to produce the (trained) learning model used in various aspects of the present invention.

In some embodiments, the training data classification model is trained using ground truth data. In some embodiments, the ground truth data comprises labeled feature data. Homologous recombination deficient ground truth feature data can be labeled, for example, as homologous recombination deficient as described above (for example, a bi-allelic silencing of one or more genes associated with homologous recombination deficiency, e.g. BRCA1 and BRCA2). In some embodiments, the homologous recombination proficient ground truth feature data is labeled based on a predetermined threshold for one or more features or by consensus labeling. For example, in some embodiments, a lower feature score (such as Signature 3 score and/or LST score) indicates the cancer is more likely homologous recombination proficient. Thus, in some embodiments, a cancer (or associated data) is labeled as homologous recombination proficient if the feature(s) of the cancer are below the feature threshold. Exemplary feature thresholds may be one or more of a signature 3 score of about 30 or less, about 20 or less, or about 10 or less; an LST score of about 20 or less, about 15 or less, about 10 or less, or about 5 or less, and/or HRD score of about 30 or less, about 25 or less, about 20 or less, or about 15 or less.

In some embodiments, the training data classification model provides an output representing a likelihood that a given cancer is homologous recombination deficient or homologous recombination proficient. The determined likelihood can be used to label the training image data (or tiles within the training image data) with a homologous recombination deficiency status. For example, in some embodiments if the cancer is about 50% or more, about 60% or more, about 70% or more, about 75% or more, about 80% or more, about 85% or more, about 87.5% or more, about 90% or more, about 92.5% or more, about 95% or more, or about 97.5% or more likely to be homologous recombination deficient, then the cancer is identified as homologous recombination deficient. In some embodiments if the cancer is about 50% or more, about 60% or more, about 70% or more, about 75% or more, about 80% or more, about 85% or more, about 87.5% or more, about 90% or more, about 92.5% or more, about 95% or more, or about 97.5% or more likely to be homologous recombination proficient, then the cancer is identified as homologous recombination proficient. In some embodiments, if the cancer is about 50% or less, about 40% or less, about 30% or less, about 25% or less, about 20% or less, about 15% or less, about 12.5% or less, about 10% or less, about 7.5% or less, about 5% or less, or about 2.5% or less likely to be homologous recombination deficient, then the cancer is identified as homologous recombination proficient. In some embodiments, if the cancer is about 50% or less, about 40% or less, about 30% or less, about 25% or less, about 20% or less, about 15% or less, about 12.5% or less, about 10% or less, about 7.5% or less, about 5% or less, or about 2.5% or less likely to be homologous recombination proficient, then the cancer is identified as homologous recombination deficient.

In some embodiments, the label for a cancer (or associated data) as homologous recombination proficient or homologous recombination deficient is determined using consensus labeling. In consensus labeling, ground truth data for a given cancer type (e.g., homologous recombination proficient cancers) can be preliminarily labeled at a plurality of different feature thresholds. When cancer types are binary (e.g., homologous recombination proficient or homologous recombination deficient), it is expected that the cancer will be consistently labeled by the model either as homologous recombination proficient or homologous recombination deficient across the plurality of different thresholds. Thus, the cancer (or associated data) can be labeled as homologous recombination proficient (and/or deficient) when the cancer is preliminarily labeled as homologous recombination proficient (and/or deficient) at or above, above, at or below, or below a selected frequency across the different thresholds (or the preliminary labeling occurs at a frequency that is within a range set for one of the given HR classes or categories). The frequency may be a determined frequency or a frequency selected based on a bimodal distribution of the of the sample statuses. In some embodiments, the cancer (or associated data) is labeled as homologous recombination proficient if the cancer (or associated data) is preliminarily labeled as homologous recombination proficient across the plurality of feature thresholds at a frequency of more than 50% of the time (such as about 60% or more, about 70% or more, about 75% or more, about 80% or more, about 85% or more, about 87.5% or more, about 90% or more, about 92.5% or more, about 95% or more, or about 97.5% or more). In some embodiments, the cancer (or associated data) is labeled as homologous recombination deficient if the cancer (or associated data) is preliminarily labeled as homologous recombination deficient across the plurality of feature thresholds at a frequency of more than 50% of the time (such as about 60% or more, about 70% or more, about 75% or more, about 80% or more, about 85% or more, about 87.5% or more, about 90% or more, about 92.5% or more, about 95% or more, or about 97.5% or more).

In another embodiment, a cancer used for training the learning model is labeled with a homologous recombination deficiency status based on a response of the cancer to an anti-cancer agent effective against a homologous recombination deficient cancer, such as a PARP inhibitor. For example, in some embodiments, a cancer tissue sample is taken from a patient and imaged before the patient is treated with an anti-cancer agent effective against a homologous recombination deficient cancer. If the anti-cancer agent is effective against the cancer, the cancer (and the image data associated with the cancer) is labeled as homologous recombination deficient. If the anti-cancer agent is not effective against the cancer, the cancer (and the image data associated with the cancer) is labeled as homologous recombination proficient. In some embodiments, the effectiveness of the anti-cancer agent in treating the cancer is measured in vitro and in some embodiments, the effectiveness is measured in vivo.

Training image data associated with a cancer labeled with a homologous recombination deficiency status is labeled according to the homologous recombination deficiency status of the cancer, and can be used to train the learning model (e.g., a deep learning model, such as a CNN or other neural network or image classifier) configured to characterize a homologous recombination deficiency status of an input (i.e., test) cancer.

Figure 1:
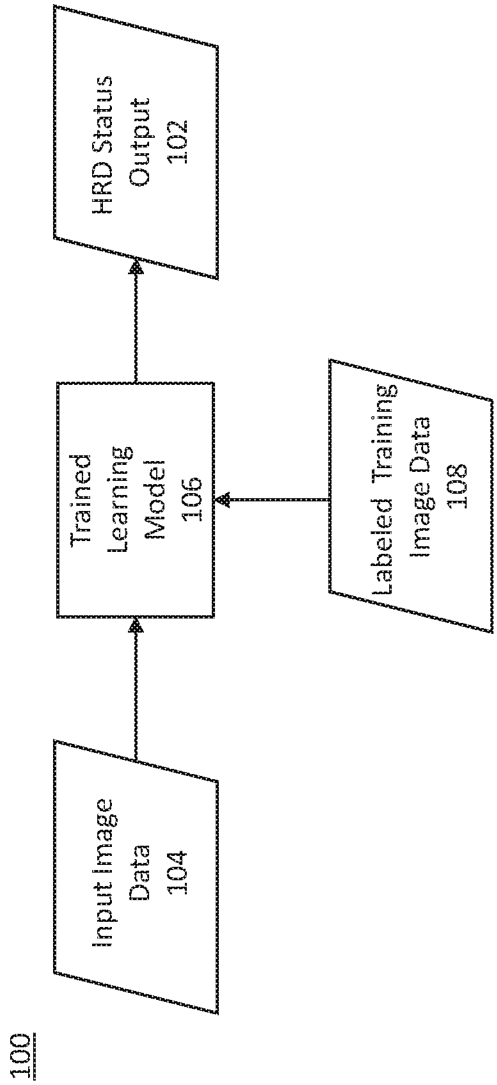
FIG. 1 illustrates an exemplary process for characterizing a cancer for homologous recombination deficiency status associated with image data using a (trained) learning model, in accordance with some embodiments.

FIG. 1 illustrates an exemplary process 100 for characterizing a cancer for homologous recombination deficiency status associated with image data using a trained learning model, in accordance with some embodiments. With reference to FIG. 1, a trained learning model 106 has been trained based on labeled training image data 108. The trained learning model 106 can include one or more neural networks (such as a CNN), one or more support vector machines, or any suitable algorithms or models or combinations thereof. Having been trained by the labeled training image data 108, the trained learning model 106 is configured to receive input image data 104, identify or characterize a homologous recombination deficiency status from the input image data 104, and provide a homologous recombination deficiency status output 102.

Figure 5:
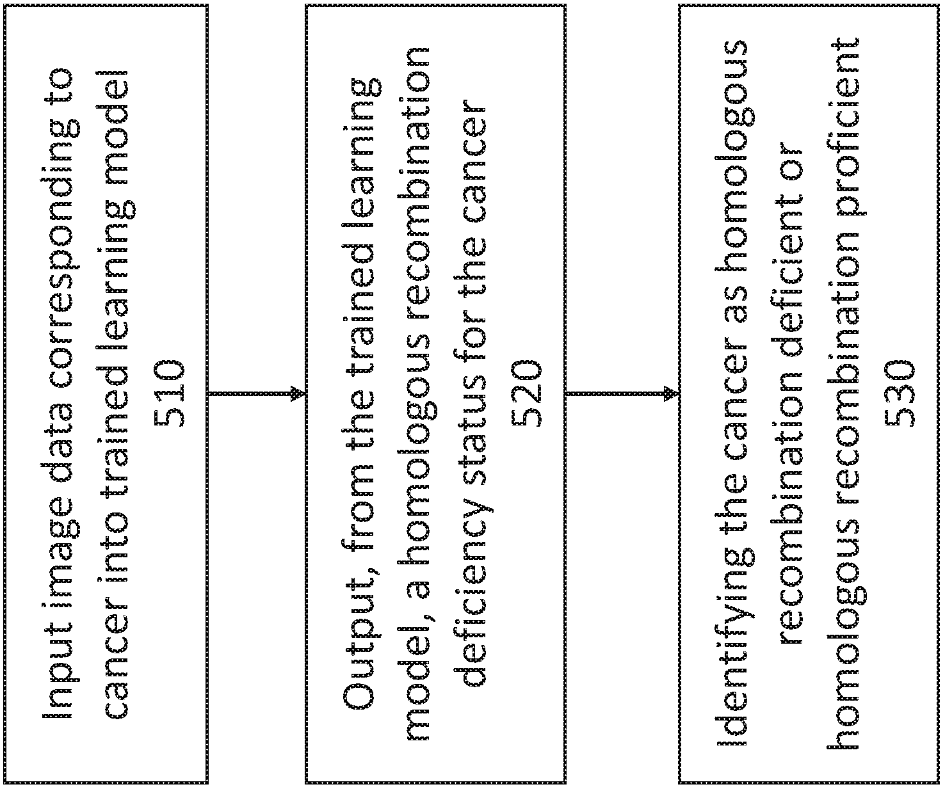
FIG. 5 shows an exemplary flow chart for identifying a cancer as homologous recombination deficient or homologous recombination proficient.

FIG. 5 shows an exemplary flow chart for identifying a cancer as homologous recombination deficient or homologous recombination proficient. Referring to FIG. 5, at step 510, image data corresponding to a cancer is inputted into a trained learning model. The trained learning model has been trained based on training image data comprising a first set of cancer image data labeled as homologous recombination deficient and a second set of cancer image data labeled as homologous recombination proficient. The trained learning model comprises a function that associates the inputted image data with a homologous recombination deficiency status. At step 520, the trained learning model outputs a homologous recombination deficiency status of the cancer. At step 530, the cancer is identified as homologous recombination deficient or homologous recombination proficient based on the outputted homologous recombination deficiency status of the cancer.

Figure 2:
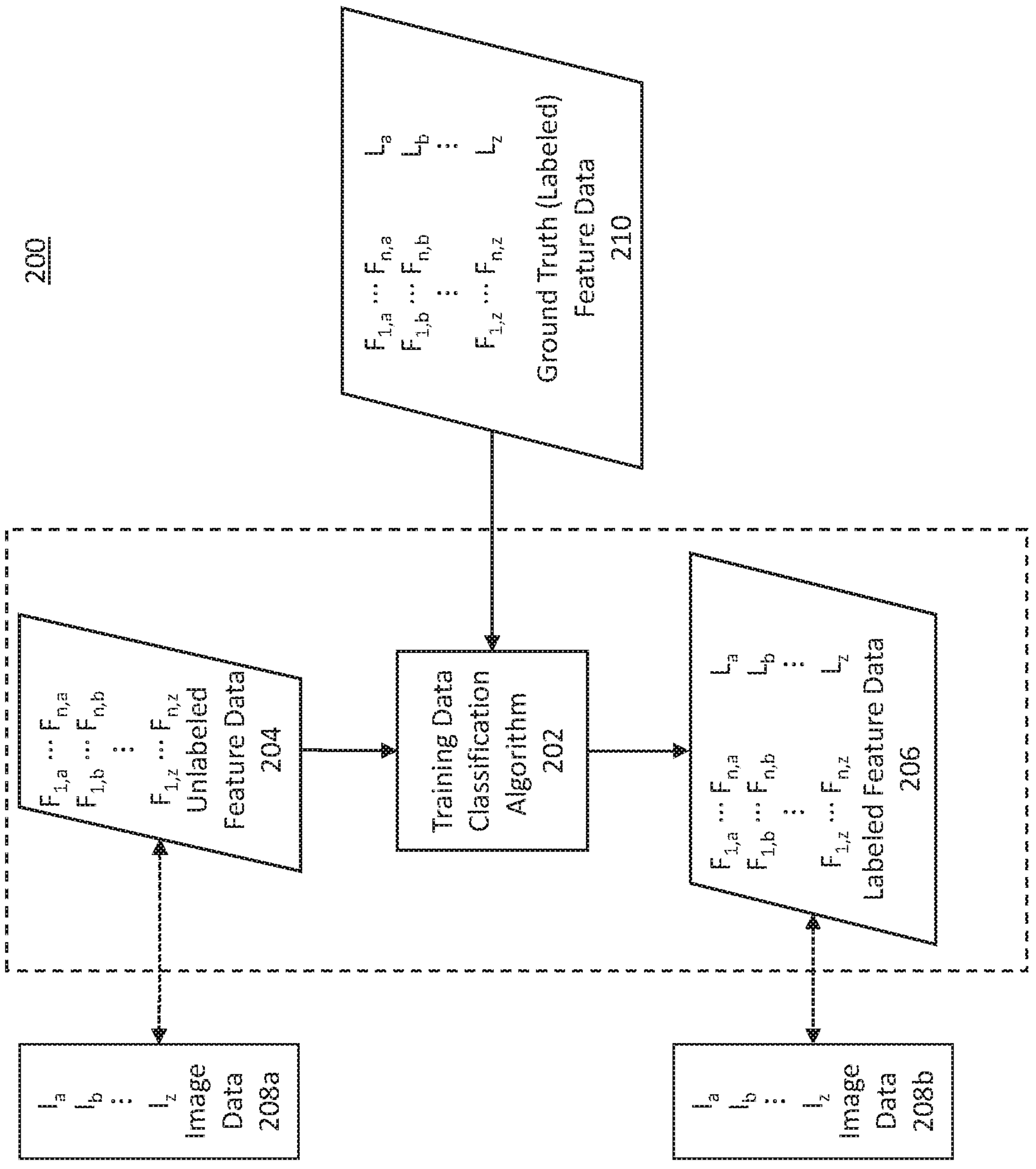
FIG. 2 illustrates an exemplary process for generating training data suitable for use in training a learning model to characterize a recombination deficiency status of a cancer from input image data associated with the cancer.

The volume of training image data available with accurately labeled homologous deficiency status is limited. To better train the learning model configured to characterize the homologous deficiency status of a test cancer, it is useful to generate additional labeled training image data accurately labeled with homologous deficiency status. FIG. 2 illustrates an exemplary process 200 for generating training data suitable for use in training a learning model to characterize a recombination deficiency status of a cancer from input image data associated with the cancer. With reference to FIG. 2, a training data classification model 202 is trained using ground truth feature data 210 from a plurality of cancer samples, which include one or more features ($F_1 \ldots F_n$) associated with homologous recombination deficiency that characterize a labeled cancer, along with the homologous recombination deficiency status label ($L_1 \ldots L_z$) of the labeled cancer. The ground truth for the cancer can be determined, for example, based on the one or more features of the cancer, a bi-allelic inactivation of one or more genes associated with homologous recombination deficiency, and/or the responsiveness of the cancer to an anti-cancer agent effective for treating a homologous recombination deficient cancer. To label training image data (see 108 of FIG. 1), unlabled feature data 204 (which are also associated with image data 208*a* associated with the cancer (($I_a \ldots I_z$)) are inputted into the trained training data classification model 202. Having been trained by the ground truth feature data 210, the trained training data classification model 202 is configured to receive the input unlabeled feature data 204, associate the input unlabled feature data 204 with labels ($L_a \ldots L_z$), and provide labeled feature data 206 as output. Because the feature data 206, now labeled, is associated with the image data 208*b*, the image data 208*b* can be labeled to generate the training image data of the learning model (106 of FIG. 1).

Figure 3:
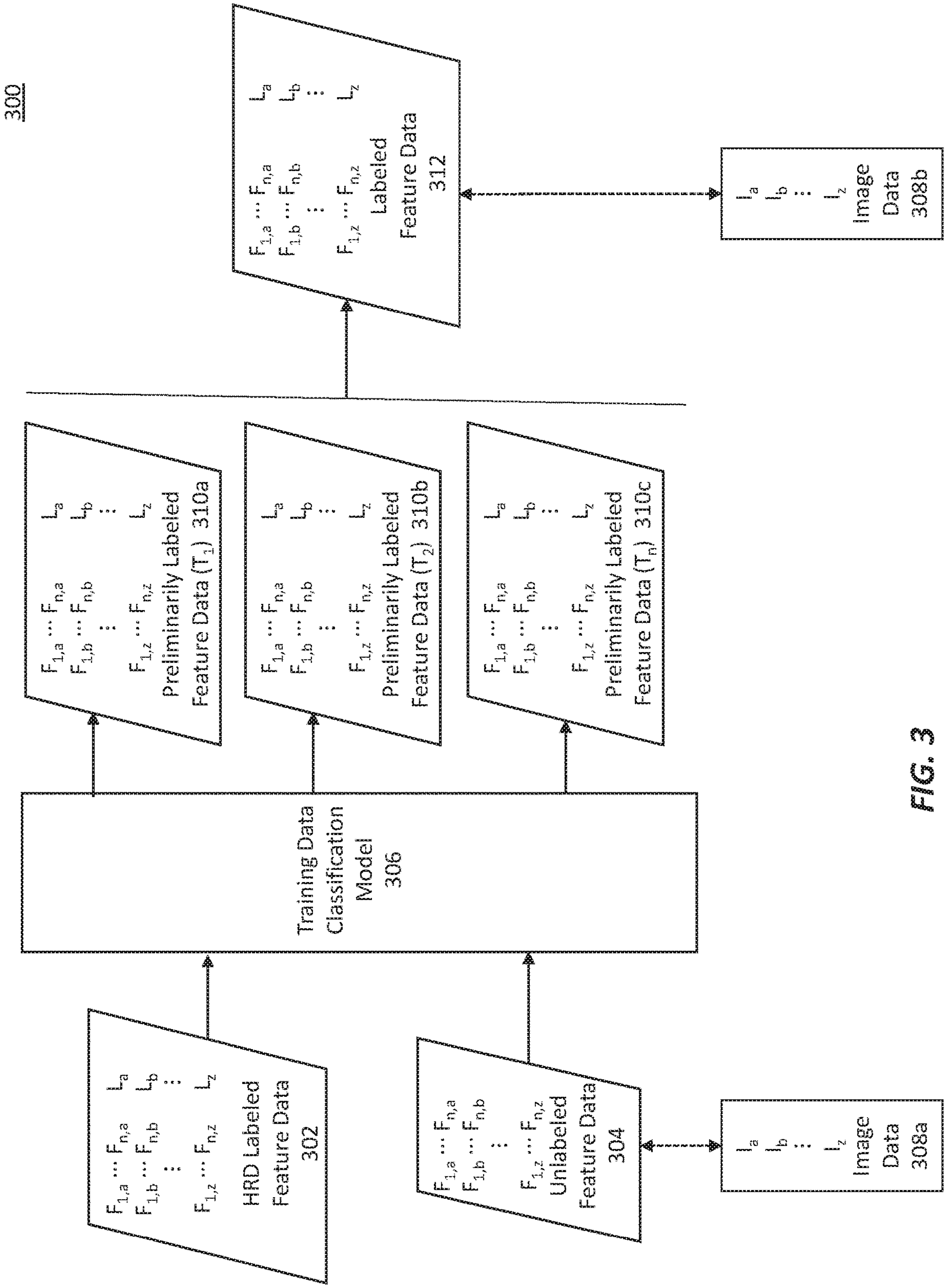
FIG. 3 illustrates an exemplary process for generating training data suitable for use in training a learning model to characterize a recombination deficiency status of a cancer from input image data associated with the cancer using consensus labeling.

FIG. 3 illustrates an alternative exemplary process 300 for generating training data suitable for use in training a learning model to characterize a recombination deficiency status of a cancer from input image data associated with the cancer, using consensus labeling. With reference to FIG. 3, a training data classification model 306 receives using labeled feature data 302 from a plurality of cancer samples, which include one or more features ($F_1 \ldots F_n$) associated with homologous recombination deficiency that characterize a labeled cancer, along with the homologous recombination deficiency status label ($L_1 \ldots L_z$) of the labeled cancer. In some embodiments, the labeled feature data is labeled as associated with a homologous recombination deficient data. For example, the ground truth for the cancer of the labeled feature data 302 can be determined based on a bi-allelic silencing of one or more genes associated with homologous recombination deficiency or the responsiveness of the cancer to an anti-cancer agent effective for treating a homologous recombination deficient cancer. Unlabeled feature data 304 is also inputted into the training classification algorithm 306. The training data classification model 306 can preliminarily label the unlabeled feature data 304 as homologous recombination proficient (and/or, in some embodiments, as homologous recombination deficient) using the plurality of different thresholds for the one or more features to define the homologous recombination proficient cancer ground truth. The training data classification model 306 can generate preliminarily labeled feature data 310*a*, 310*b*, and 310*c*, and the preliminary labels can depend on the threshold ($T_1$, $T_2 \ldots T_n$) for each output set. Selected labeled feature data 312 can be selected from the output labeled feature data sets 310*a*, 310*b*, and 310*c*, for example based on how consistent the samples were classified as homologous recombination deficient or homologous recombination proficient (for example, using a frequency threshold). At least a portion of the unlabeled feature data 304 and the labeled feature data 302 inputted into the training data classification model 306 is associated with a cancer, to which image data 308*a* can also be associated (either to the unlabeled feature data 304, or both the labeled feature data 302 and the unlabeled feature data 304, or any subset thereof). Because the selected labeled feature data 312 is associated with the image data 308*b*, the image data 308*b* can be labeled to generate the training image data of the learning model (106 of FIG. 1).

The above-descriptions of the embodiments of FIGS. 2 and 3 may also be read in conjunction with (and modified based on) Examples 2 and 3 et al which describe methods for determining labels for cancers (using molecular information (features) about the cancer and classification (e.g. regression) models) which can then be assigned to the respective image data. In Example 3, a set of features is determined for each cancer in a cancer dataset. Using a variety of different thresholds for some of those features, a classification model is trained numerous times with different ground truth samples of the dataset. These classification models are each used on the full dataset so that for each sample at each different threshold there is a prediction or determination of its status (here, HRD status or HRD probability). This consensus result can then be used to identify a new sub-set of the dataset to use for a final training of the classification model (i.e. to identify samples which consistently, over all or substantially all thresholds, meet certain thresholds (here, a HRD probability less than a value)). This final classification model is then applied to the full dataset again to determine or predict the status for each data sample again. Those samples in the full set with a status (here, HRD probability)—determined by the final classification model—meeting certain threshold requirements can (along with their respective images) then be labelled into the appropriate class (here, HRD and HRP) and those labelled images then used as the ground truth training data for an image classification model.

The operations described above, including those described with reference to FIGS. 1-3 and 5, are optionally implemented by components depicted in FIG. 4. It would be clear to a person of ordinary skill in the art how other processes, for example, combinations or sub-combinations of all or part of the operations described above, may be implemented based on the components depicted in FIG. 4. It would also be clear to a person having ordinary skill in the art how the methods, techniques, systems, and devices described herein may be combined with one another, in whole or in part, whether or not those methods, techniques, systems, and/or devices are implemented by and/or provided by the components depicted in FIG. 4.

Figure 4:
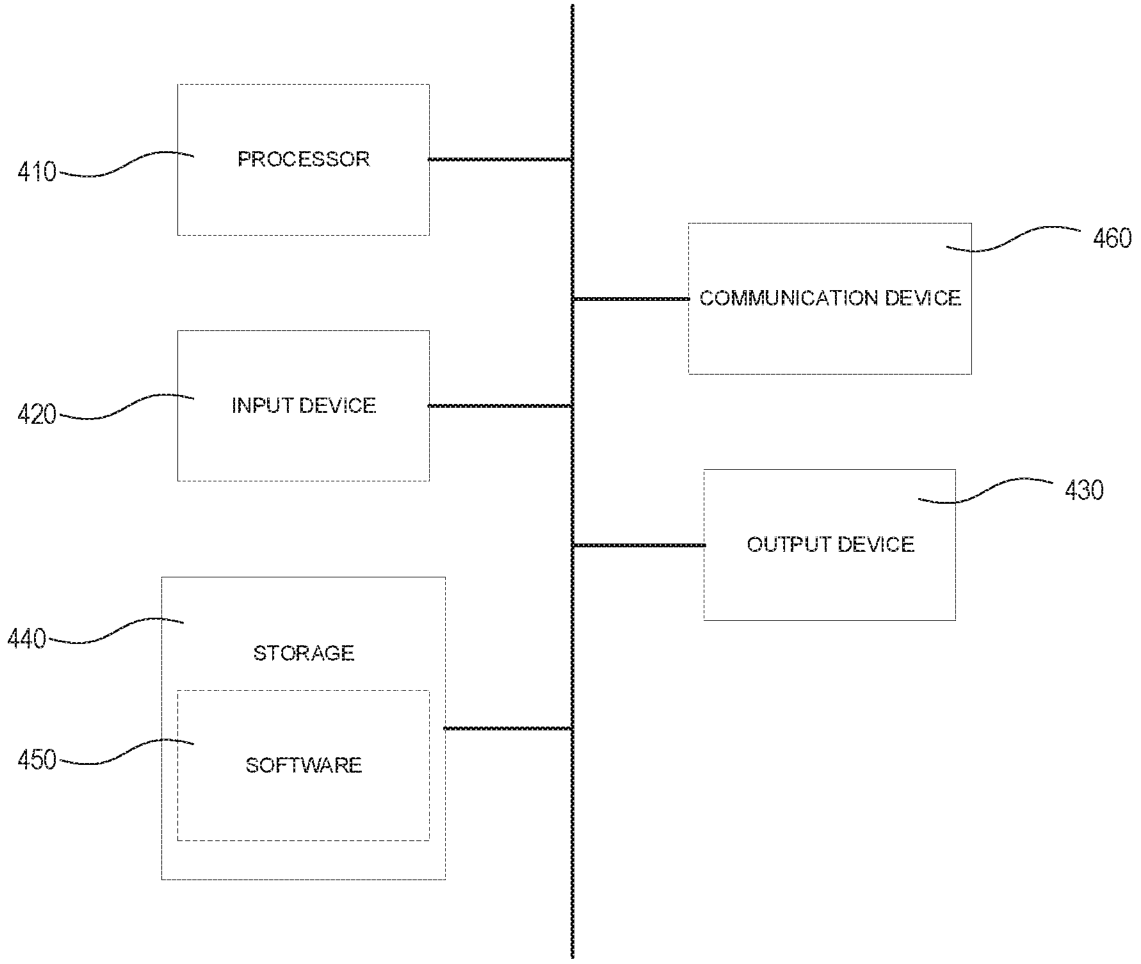
FIG. 4 depicts an exemplary electronic device, in accordance with some embodiments.

FIG. 4 illustrates an example of a computing device in accordance with one embodiment. Device 400 can be a host computer connected to a network. Device 400 can be a client computer or a server. As shown in FIG. 4, device 400 can be any suitable type of microprocessor-based device, such as a personal computer, workstation, server, or handheld computing device (portable electronic device) such as a phone or tablet. The device can include, for example, one or more of processor 410, input device 420, output device 430, storage 440, and communication device 460. Input device 420 and output device 430 can generally correspond to those described above, and can either be connectable or integrated with the computer.

Input device 420 can be any suitable device that provides input, such as a touch screen, keyboard or keypad, mouse, or voice-recognition device. Output device 430 can be any suitable device that provides output, such as a touch screen, haptics device, or speaker.

Storage 440 can be any suitable device that provides storage, such as an electrical, magnetic or optical memory including a RAM, cache, hard drive, or removable storage disk. Communication device 460 can include any suitable device capable of transmitting and receiving signals over a network, such as a network interface chip or device. The components of the computer can be connected in any suitable manner, such as via a physical bus or wirelessly.

Software 450, which can be stored in storage 440 and executed by processor 410, can include, for example, the programming that embodies the functionality of the present disclosure (e.g., as embodied in the devices as described above).

Software 450 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 440, that can contain or store programming for use by or in connection with an instruction execution system, apparatus, or device.

Software 450 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 400 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 400 can implement any operating system suitable for operating on the network. Software 450 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

Cancer Treatment

All references in this specification to a "salt" or the "salts" of an entity (e.g. anti-cancer agent, such as, by way of example only, a PARP inhibitor) means its "pharmaceutically acceptable salt(s)" and such references are to be read accordingly.

A cancer characterized (or identified) as homologous recombination deficient (or above a predetermined likelihood of being homologous recombination deficient) can be treated by administering to the patient an anti-cancer agent effective against a homologous recombination deficient cancer. In some embodiments, the anti-cancer agent is a PARP inhibitor. In some embodiments, the PARP inhibitor is a PARP-1 inhibitor. In some embodiments, the PARP-1 inhibitor is a PARP-2 inhibitor. In some embodiments, the anti-cancer agent effective against a homologous recombination deficient cancer is administered to the patient in combination with one or more additional anti-cancer therapies. Additional methods for treating a homologous recombination deficient cancer are described in US 2019/0060285 A1; WO 2017/151554 A1; WO 2018/213732 A1; WO 2019/071123 A1; International Patent Application No. PCT/US2018/067653; and International Patent Application No. PCT/US2019/016648.

In some embodiments, a patient or population of patients to be treated with a combination therapy of the present disclosure have a solid tumor. In some embodiments, a solid tumor is a melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma.

In embodiments, a PARP inhibitor inhibits PARP-1 and/or PARP-2. In some embodiments, the agent is a small molecule, a nucleic acid, a polypeptide (e.g., an antibody), a carbohydrate, a lipid, a metal, or a toxin. In related embodiments, the agent is ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ONO2231, PD 128763, R 503, R554, rucaparib (RUBRACA) (AG-014699, PF-01367338), SBP 101, SC 101914, simmiparib, talazoparib (BMN-673), veliparib (ABT-888), WW 46, 2-(4-(trifluoromethyl)phenyl)-7,8-dihydro-5H-thiopyrano[4,3-d]pyrimidin-4-ol, and salts or derivatives thereof. In some related embodiments, the agent is niraparib, olaparib, rucaparib, talazoparib, veliparib, pamiparib, or salts or derivatives thereof. In certain embodiments, the agent is niraparib or a salt or derivative thereof. In certain embodiments, the agent is olaparib or a salt or derivative thereof. In certain embodiments, the agent is rucaparib or a salt or derivative thereof. In certain embodiments, the agent is talazoparib or a salt or derivative thereof. In certain embodiments, the agent is veliparib or a salt or derivative thereof.

In some embodiments, the anti-cancer agent is 2X 121, fluzoparib, IMP-4297, niraparib, NMS-P293, NOV-140101, olaparib, pamiparib, rucaparib, talazoparib, or veliparib.

In embodiments, a PARP inhibitor (e.g., niraparib) is administered to a patient or population of subjects who has exhibited response to prior therapy. In embodiments, the patient or population of subjects has exhibited response to prior therapy with a chemotherapeutic agent. In embodiments, the chemotherapeutic agent is a platinum agent.

In embodiments, a PARP inhibitor (e.g., niraparib) is administered as a maintenance therapy following complete or partial response to at least one platinum based therapy or at least two platinum-based therapies. In embodiments, a platinum-based therapy comprises administering to a patient in need thereof a platinum-based agent selected from cisplatin, carboplatin, oxaliplatin, nedaplatin, triplatin tetranitrate, phenanthriplatin, picoplatin, or satraplatin. In embodiments, response to the most recent platinum-based chemotherapy regimen is a complete response. In embodiments, response to the most recent platinum-based chemotherapy regimen is a partial response. In embodiments, response to the penultimate platinum-based chemotherapy regimen is a complete response. In some embodiments, response to the penultimate platinum-based chemotherapy regimen is a partial response.

In embodiments, a PARP inhibitor is niraparib. In embodiments, a patient is administered a dose equivalent to about 100 mg, about 200 mg, about 300 mg, about 400 mg, or about 500 mg of niraparib, or a salt or derivative thereof (e.g., a dose equivalent to about 100 mg, about 200 mg, or about 300 mg of niraparib free base). In embodiments, administered niraparib comprises niraparib tosylate monohydrate. In embodiments, administered niraparib is administered as niraparib tosylate monohydrate.

In embodiments, niraparib is administered at a dose equivalent to about 100 mg of niraparib free base (e.g., a pharmaceutically acceptable salt of niraparib such as niraparib tosylate monohydrate is administered at a dose equivalent to about 100 mg of niraparib free base). In embodiments, niraparib is administered at a dose equivalent to about 200 mg of niraparib free base (e.g., a pharmaceutically acceptable salt of niraparib such as niraparib tosylate monohydrate is administered at a dose equivalent to about 200 mg of niraparib free base. In embodiments, niraparib is administered at a dose equivalent to about 300 mg of niraparib free base (e.g., a pharmaceutically acceptable salt of niraparib such as niraparib tosylate monohydrate is administered at a dose equivalent to about 300 mg of niraparib free base).

In embodiments, an administered amount of niraparib is about 300 mg of niraparib (e.g., an amount of a pharmaceutically acceptable salt of niraparib such as niraparib tosylate monohydrate equivalent to about 300 mg of niraparib free base). In some embodiments, the regimen comprises administration of 300 mg of niraparib once daily (e.g., an amount of a pharmaceutically acceptable salt of niraparib such as niraparib tosylate monohydrate equivalent to about 300 mg of niraparib free base once daily).

In some embodiments, an administered amount of niraparib is about 200 mg of niraparib (e.g., an amount of a pharmaceutically acceptable salt of niraparib such as niraparib tosylate monohydrate equivalent to about 200 mg of niraparib free base). In some embodiments, the regimen comprises administration of 200 mg of niraparib once daily (e.g., an amount of a pharmaceutically acceptable salt of niraparib such as niraparib tosylate monohydrate equivalent to about 200 mg of niraparib free base once daily).

In some embodiments, an administered amount of niraparib is about 100 mg of niraparib (e.g., an amount of a pharmaceutically acceptable salt of niraparib such as niraparib tosylate monohydrate equivalent to about 100 mg of niraparib free base). In some embodiments, the regimen comprises administration of 100 mg of niraparib once daily (e.g., an amount of a pharmaceutically acceptable salt of niraparib such as niraparib tosylate monohydrate equivalent to about 100 mg of niraparib free base once daily).

In some embodiments, the regimen comprises at least one 21-day cycle. In some embodiments, the regimen comprises a plurality of 21-day cycles. In some embodiments, the regimen comprises one 21-day cycle. In some embodiments, the regimen comprises two 21-day cycles. In some embodiments, the regimen comprises three 21-day cycles. In some embodiments, the regimen comprises continuous 21 day cycles. In some embodiments, the regimen comprises administration of an effective dose of a PARP inhibitor such as niraparib daily until disease progression or unacceptable toxicity occurs. In some embodiments, the regimen comprises a daily dose of at least about 100, 200, or 300 mg niraparib per day dosed until disease progression or unacceptable toxicity occurs (e.g., a dose of a pharmaceutically acceptable salt of niraparib such as niraparib toslyate monohydrate in an amount equivalent to at least about 100, 200, or 300 mg niraparib free base or a dose of a pharmaceutically acceptable salt of niraparib such as niraparib toslyate monohydrate in an amount equivalent to about 100, 200, or 300 mg niraparib free base).

In some embodiments, the regimen comprises at least one 28-day cycle. In some embodiments, the regimen comprises a plurality of 28-day cycles. In some embodiments, the regimen comprises one 28-day cycle. In some embodiments, the regimen comprises two 28-day cycles. In some embodiments, the regimen comprises three 28-day cycles. In some embodiments, the regimen comprises continuous 28-day cycles. In some embodiments, the regimen comprises administration of an effective dose of a PARP inhibitor such as niraparib daily until disease progression or unacceptable toxicity occurs. In some embodiments, the regimen comprises a daily dose of at least 100, 200, or 300 mg niraparib per day dosed until disease progression or unacceptable toxicity occurs (e.g., a dose of a pharmaceutically acceptable salt of niraparib such as niraparib tosylate monohydrate in an amount equivalent to at least about 100, 200, or 300 mg niraparib free base or a dose of a pharmaceutically acceptable salt of niraparib such as niraparib tosylate monohydrate in an amount equivalent to about 100, 200, or 300 mg niraparib free base).

In some embodiments, a PARP inhibitor (e.g., niraparib) is administered in a regimen determined to achieve i) prolonged progression free survival as compared to control, ii) a reduced hazard ratio for disease progression or death as compared to control, iii) prolonged overall survival as compared to control, or iv) an overall response rate of at least 30%. In embodiments, a regimen comprises a daily dose (e.g., a daily oral dose) of niraparib (e.g., a daily oral dose of a pharmaceutically acceptable salt of niraparib such as niraparib tosylate monohydrate in an amount equivalent to about 200 mg or about 300 mg niraparib free base).

In some embodiments, the methods prolong progression free survival as compared to control. In some embodiments, the methods reduce the hazard ratio for disease progression or death as compared to control. In some embodiments, the methods prolong overall survival as compared to control. In some embodiments, the methods achieve an overall response rate of at least 30%. In some embodiments, the methods achieve improved progression free survival 2 as compared to control. In some embodiments, the methods achieve improved chemotherapy free interval as compared to control. In some embodiments, the methods achieve improved time to first subsequent therapy as compared to control. In some embodiments, the methods achieve improved time to second subsequent therapy as compared to control. In some embodiments, the methods have been determined to not have a detrimental effect on Quality of Life as determined by FOSI and/or EQ-5D-5L. In some embodiments, the methods have been determined to not impact the effectiveness of a subsequent treatment with a chemotherapeutic agent (e.g., a platinum agent, including but not limited to, cisplatin, carboplatin, oxaliplatin, nedaplatin, triplatin tetranitrate, phenanthriplatin, picoplatin, or satraplatin.

DNA-Damaging or Repair-Inhibiting Agents

In some embodiments, the anti-cancer agent is a DNA-damaging agent or a repair-inhibiting agent. See, for example, US 2019/0060285 A1. A DNA-damaging or repair-inhibiting agent refers to an agent that causes DNA damages. It is targeted at some of the key regulatory proteins involved in the DNA repair process. The DNA repair process in mammalian cells is a multi-pathway mechanism that protects cells from the plethora of DNA damaging agents that are known to attack nuclear DNA. The majority of current anticancer therapies rely on this ability to create DNA lesions, leading to apoptosis/cell death. A cells natural ability to repair such DNA damage is a major cause of resistance to these existing antitumour agents. It seems logical, therefore, that by modulating these repair mechanisms, greater killing effect to anticancer agents would occur.

A DNA-damaging or repair-inhibiting agent includes, but not limited to, a PARP inhibitor, a platin, a topoisomerase I and/or II inhibitor, and an inhibitor of DNA checkpoint proteins including WEE1, CHK1, CHK2, CDK1, CDK2, ATM, and ATR.

In some embodiments, the DNA-damaging or repair-inhibiting agent is a PARP inhibitor, such as niraparib, iniparib, talazoparib, olaparib, rucaparib, veliparib, or CEP-9722.

In some embodiments, the DNA-damaging or repair-inhibiting agent is a platin. A platin refers to a platinum-based antineoplastic drug, which is a chemotherapeutic agent to treat cancer. A platin is a coordination complex of platinum. Platinum-based antineoplastic drugs cause cross-linking of DNA as monoadduct, interstrand crosslinks, intrastrand crosslinks or DNA protein crosslinks. Mostly they act on the adjacent N-7 position of guanine, forming 1, 2 intrastrand crosslink. The resultant crosslinking inhibit DNA repair and/or DNA synthesis in cancer cells. Examples of platins include cisplatin, carboplatin, oxaliplatin, satraplatin, picoplatin, nedaplatin, triplatin, and lipoplatin.

In some embodiments, the DNA-damaging or repair-inhibiting agent is a topoisomerase inhibitor. Topoisomerase inhibitors are agents designed to interfere with the action of topoisomerase enzymes, which include topoisomerase I and II. Topoisomerase are enzymes that control the changes in DNA structure by catalyzing the breaking and rejoining of the phosphodiester backbone of DNA strands during the normal cell cycle. The topoisomerase I inhibitor can be used in the present invention includes, but not limited to, irinotecan, topotecan, camptothecin, or lamellarin D. The topoisomerase II inhibitor can be used in the present invention includes, but not limited to, etoposide (VP-16), teniposide, doxorubicin, daunorubicin, mitoxantrone, amsacrine, ellipticine, aurintricarboxylic acid, HU-331, ICRF-187, ICRF-193, and mitindomide.

Oral Dosage Regimens

In some embodiments, the regimen comprises at least one oral dose of a PARP inhibitor such as niraparib. In some embodiments, the regimen comprises a plurality of oral doses. In some embodiments, the regimen comprises once daily (QD) dosing. In embodiments, a regimen comprises a once daily dose of a pharmaceutically acceptable salt of niraparib such as niraparib tosylate monohydrate in an amount equivalent to about 200 mg or about 300 mg niraparib free base.

In some embodiments, the oral dose is an amount of a PARP inhibitor (e.g., niraparib) within a range of about 10 mg to about 500 mg. In some embodiments, the dose is within a range of about 25 mg to about 400 mg. In some embodiments, the dose is within a range of about 50 mg to about 300 mg. In some embodiments, the dose is within a range of about 150 mg to about 350 mg. In some embodiments, the dose is within a range of about 50 mg to about 250 mg. In some embodiments, the dose is within a range of about 50 mg to about 200 mg. In some embodiments, the dose is within a range of about 50 mg to about 100 mg. In some embodiments, the dose is within a range of about 100 mg to about 300 mg. In embodiments, a PARP inhibitor is niraparib.

In some embodiments, the oral dose is an amount of a PARP inhibitor (e.g., niraparib) within a range of about 10 mg to about 500 mg. In some embodiments, the dose is within a range of about 25 mg to about 400 mg. In some embodiments, the dose is within a range of about 50 mg to about 300 mg. In some embodiments, the dose is within a range of about 150 mg to about 350 mg. In some embodiments, the dose is within a range of about 50 mg to about 250 mg. In some embodiments, the dose is within a range of about 50 mg to about 200 mg. In some embodiments, the dose is within a range of about 50 mg to about 100 mg. In some embodiments, the dose is within a range of about 100 mg to about 300 mg. In embodiments, a PARP inhibitor is niraparib.

In some embodiments, the oral dose is an amount of niraparib within a range of about 5 to about 400 mg (an amount equivalent to about 5 to about 400 mg of niraparib free base). In some embodiments, the amount of niraparib is about 5, about 10, about 25, about 50, about 100, about 150, about 200, about 250, about 300, about 350, or about 400 mg (e.g., an amount equivalent to about 5, about 10, about 25, about 50, about 100, about 150, about 200, about 250, about 300, about 350, or about 400 mg of niraparib free base). In embodiments, an oral dose comprises niraparib tosylate monohydrate.

In embodiments, an oral dose comprises niraparib (e.g., a pharmaceutically acceptable salt of niraparib such as niraparib tosylate monohydrate) in an amount equivalent to about 5 to about 400 mg of niraparib free base. In embodiments, an oral dose comprises niraparib (e.g., a pharmaceutically acceptable salt of niraparib such as niraparib tosylate monohydrate) in an amount equivalent to about 5 to about 400 mg of niraparib free base. In embodiments, an oral dose comprises an amount of niraparib (e.g., a pharmaceutically acceptable salt of niraparib such as niraparib tosylate monohydrate) that is equivalent to about 5, about 10, about 25, about 50, about 100, about 150, about 200, about 250, about 300, about 350, or about 400 mg of niraparib free base.

In some embodiments, an oral dose comprises niraparib (e.g., a pharmaceutically acceptable salt of niraparib such as niraparib tosylate monohydrate) in an amount equivalent to about 300 mg of niraparib free base. In some embodiments, the regimen comprises oral administration of niraparib (e.g., a pharmaceutically acceptable salt of niraparib such as niraparib tosylate monohydrate) in an amount equivalent to about 300 mg of niraparib free base once daily.

In some embodiments, an oral dose comprises niraparib (e.g., a pharmaceutically acceptable salt of niraparib such as niraparib tosylate monohydrate) in an amount equivalent to about 200 mg of niraparib free base. In some embodiments, the regimen comprises oral administration of niraparib (e.g., a pharmaceutically acceptable salt of niraparib such as niraparib tosylate monohydrate) in an amount equivalent to about 200 mg of niraparib free base once daily.

In some embodiments, an oral dose comprises niraparib (e.g., a pharmaceutically acceptable salt of niraparib such as niraparib tosylate monohydrate) in an amount equivalent to about 100 mg of niraparib free base. In some embodiments, the regimen comprises oral administration of niraparib (e.g., a pharmaceutically acceptable salt of niraparib such as niraparib tosylate monohydrate) in an amount equivalent to about 100 mg of niraparib free base once daily.

In some embodiments, the oral dose is administered in one or more unit dosage forms. In some embodiments, the one or more unit dosage forms are capsules. In some embodiments, the one or more unit dosage forms are tablets.

In embodiments, each unit dosage form comprises about 5, about 10, about 25, about 50, or about 100 mg of niraparib. In embodiments, each unit dosage form comprises an amount equivalent to about 5, about 10, about 25, about 50, or about 100 mg of niraparib free base (e.g., each unit dosage form comprises a pharmaceutically acceptable salt of niraparib such as niraparib tosylate monohydrate in an amount equivalent to about 5, about 10, about 25, about 50, or about 100 mg of niraparib free base).

In embodiments, a 100 mg unit dosage form comprises niraparib (e.g., a pharmaceutically acceptable salt of niraparib such as niraparib tosylate monohydrate) in an amount equivalent to about 100 mg of niraparib free base. In embodiments, a unit dosage form is a tablet. In embodiments, a unit dosage form is a capsule.

It is understood that any combination of unit dosage forms can be combined to form a once daily (QD) dose. For example, three 100 mg unit dosage forms (e.g., each unit dosage form comprising an amount of niraparib—such as a pharmaceutically acceptable salt of niraparib that is niraparib tosylate monohydrate—that is equivalent to about 100 mg of niraparib free base) can be taken once daily such that about 300 mg of niraparib (e.g., about 300 mg of niraparib free base) is administered once daily, or two 100 mg unit dosage forms (e.g., each unit dosage form comprising an amount of niraparib—such as a pharmaceutically acceptable salt of niraparib that is niraparib tosylate monohydrate—that is equivalent to about 100 mg of niraparib free base) can be taken once daily such that about 200 mg of niraparib (e.g., about 200 mg of niraparib free base) is administered once daily.

In some embodiments, niraparib is administered as a single 100 mg unit dosage form (e.g., a single unit dosage form comprising niraparib (e.g., a pharmaceutically acceptable salt of niraparib such as niraparib tosylate monohydrate) in an amount equivalent to about 100 mg niraparib free base). In some embodiments, niraparib is administered 100 mg QD; for example, an amount of niraparib (e.g., a pharmaceutically acceptable salt of niraparib such as niraparib tosylate monohydrate) that is equivalent to about 100 mg niraparib free base.

In some embodiments, niraparib is administered as a single 200 mg unit dosage form (e.g., a single unit dosage form comprising niraparib (e.g., a pharmaceutically acceptable salt of niraparib such as niraparib tosylate monohydrate) in an amount equivalent to about 200 mg niraparib free base). In some embodiments, niraparib is administered 200 mg QD; for example, an amount of niraparib (e.g., a pharmaceutically acceptable salt of niraparib such as niraparib tosylate monohydrate) that is equivalent to about 200 mg niraparib free base. In some embodiments, niraparib is administered as 2×100 mg QD (i.e., niraparib is administered as two 100 mg unit dosage forms); for example, niraparib is administered as two unit dosage forms, each unit dosage form comprising niraparib (e.g., a pharmaceutically acceptable salt of niraparib such as niraparib tosylate monohydrate) in an amount equivalent to about 100 mg niraparib free base.

In some embodiments, niraparib is administered as a single 300 mg unit dosage form (e.g., a single unit dosage form comprising niraparib (e.g., a pharmaceutically acceptable salt of niraparib that is niraparib tosylate monohydrate) in an amount equivalent to about 300 mg niraparib free base). In some embodiments, niraparib is administered about 300 mg QD (e.g., an amount of a pharmaceutically acceptable salt of niraparib that is niraparib tosylate monohydrate that is equivalent to about 300 mg niraparib free base). In some embodiments, niraparib is administered as 3×100 mg QD (i.e., niraparib is administered as three unit dosage forms of about 100 mg); for example, niraparib is administered as three unit dosage forms, each unit dosage form comprising a pharmaceutically acceptable salt of niraparib (e.g., niraparib tosylate monohydrate) in an amount equivalent to about 100 mg niraparib free base. In some embodiments, niraparib is administered as 2×150 mg QD (i.e., niraparib is administered as two unit dosage forms of about 150 mg); for example, niraparib is administered as two unit dosage forms, each unit dosage form comprising a pharmaceutically acceptable salt of niraparib (e.g., niraparib tosylate monohydrate) in an amount equivalent to about 150 mg niraparib free base.

In some embodiments, the regimen comprises administration of an effective dose of a PARP inhibitor (e.g., niraparib) daily until disease progression or unacceptable toxicity occurs. In some embodiments, the regimen comprises a daily dose of 100 mg, 200 mg, 300 mg or more of a PARP inhibitor (e.g., niraparib) per day dosed until disease progression or unacceptable toxicity occurs. In some embodiments, the regimen comprises a daily dose of 300 mg of niraparib (e.g., a pharmaceutically acceptable salt of niraparib such as niraparib tosylate monohydrate) per day dosed until disease progression or unacceptable toxicity occurs. In some embodiments, the regimen comprises a daily dose of 200 mg of niraparib (e.g., a pharmaceutically acceptable salt of niraparib such as niraparib tosylate monohydrate) per day dosed until disease progression or unacceptable toxicity occurs. In some embodiments, the regimen comprises a daily dose of 100 mg of niraparib (e.g., a pharmaceutically acceptable salt of niraparib such as niraparib tosylate monohydrate) per day dosed until disease progression or unacceptable toxicity occurs.

In some embodiments, the range of an oral dose is bounded by a lower limit and an upper limit, the upper limit being larger than the lower limit.

In some embodiments, the lower limit may be about 10 mg, about 25 mg, about 50 mg, or about 100 mg of a PARP inhibitor (e.g., niraparib). In embodiments, the lower limit may be an amount of niraparib (e.g., a pharmaceutically acceptable salt of niraparib such as niraparib tosylate monohydrate) that is equivalent to about 10 mg, about 25 mg, about 50 mg, or about 100 mg of niraparib free base.

In some embodiments, the upper limit may be about 150 mg, about 200 mg, about 250 mg, about 300 mg, about 350 mg, about 400 mg or about 500 mg of a PARP inhibitor (e.g., niraparib). In embodiments, the upper limit may be an amount of niraparib (e.g., a pharmaceutically acceptable salt of niraparib such as niraparib tosylate monohydrate) that is equivalent to about 150 mg, about 200 mg, about 250 mg, about 300 mg, about 350 mg, about 400 mg or about 500 mg of niraparib free base.

Combination Therapy

PARP inhibitors (e.g., niraparib) can be administered alone as a monotherapy or in combination with other therapies. Combination therapies that enhance or synergize with cytotoxic agents without significantly increasing toxicity would provide substantial benefit to ovarian as well other types of cancer patients.

In embodiments, a PARP inhibitor (e.g., niraparib) is administered in combination with at least one additional therapeutic agent or therapy. In embodiments, a PARP inhibitor such as niraparib is administered simultaneously or sequentially with an additional therapeutic agent, such as, for example, a chemotherapeutic agent. In some embodiments, a PARP inhibitor (e.g., niraparib) is administered before, during, or after administration of an additional therapeutic agent (e.g., a chemotherapeutic agent). In embodiments, administering of a PARP inhibitor (e.g., niraparib) and an at least one additional therapeutic agent is according to a regimen that achieves any one of or combination of: prolonged progression free survival; reduced hazard ratio for disease progression or death; and/or prolonged overall survival or a positive overall response rate. In embodiments, administering of a PARP inhibitor (e.g., niraparib) is according to any of the regimens described herein.

When administered as part of a combination therapy, a PARP inhibitor (e.g., niraparib) can be administered according to any of the regimens and formulations described herein. For example, the PARP inhibitor (e.g., niraparib) can be administered according to any of the oral dosing regimens described herein.

Administration of the PARP inhibitor (e.g., niraparib) can occur simultaneously or sequentially with an additional therapeutic agent (e.g., a chemotherapeutic agent). In embodiments, niraparib can be administered prior to (e.g., 5-minutes, 15-minutes, 30-minutes, 45-minutes, 1-hour, 2-hours, 4-hours, 6-hours, 12-hours, 24-hours, 48-hours, 72-hours, 96-hours, 1-week, 2-weeks, 3-weeks, 4-weeks, 5-weeks, 6-weeks, 8-weeks, or 12-weeks) before, concurrently with, or subsequent to (e.g., 5-minutes, 15-minutes, 30-minutes, 45-minutes, 1-hour, 2-hours, 4-hours, 6-hours, 12-hours, 24-hours, 48-hours, 72-hours, 96-hours, 1-week, 2-weeks, 3-weeks, 4-weeks, 5-weeks, 6-weeks, 8-weeks, or 12-weeks) after the administration of the chemotherapeutic agent to a subject in need thereof. In some embodiments the PARP inhibitor (e.g., niraparib) and the chemotherapeutic agent are administered 1-minute apart, 10-minutes apart, 30-minutes apart, less than 1-hour apart, 1-hour to 2-hours apart, 2-hours to 3-hours apart, 3-hours to 4-hours apart, 4-hours to 5-hours apart, 5-hours to 6-hours apart, 6-hours to 7-hours apart, 7-hours to 8-hours apart, 8-hours to 9-hours apart, 9-hours to 10-hours apart, 10-hours to 11-hours apart, 11-hours to 12-hours apart, no more than 24-hours apart, or no more than 48-hours apart.

Chemotherapeutic Agents

In embodiments, a PARP inhibitor (e.g., niraparib) is administered in combination (e.g., simultaneously or sequentially) with at least one additional chemotherapeutic (i.e., a chemical agent that inhibits the proliferation, growth, life-span and/or metastatic activity of cancer cells).

Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines (e.g., altretamine, triethylenemelamine, trietylenephosphoramide, triethiylenethiophosphoramide and trimethylolomelamine); acetogenins; delta-9-tetrahydrocannabinol (e.g., dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (e.g., cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate;

hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; xeloda; ibandronate; topoisomerase inhibitor RFS 2000; difluoromethylornithine (DMFO); retinoids such as retinoic acid; capecitabine; pharmaceutically acceptable salts, acids or derivatives of any of the above; as well as combinations of two or more of the above such as CHOP, an abbreviation for a combined therapy of cyclophosphamide, doxorubicin, vincristine, and prednisone, and FOLFOX, an abbreviation for a treatment regimen with oxaliplatin (ELOXATIN™) combined with 5-FU and leucovovin.

Chemotherapeutic agents also include anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGACE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

In embodiments, a PARP inhibitor (e.g., niraparib) is administered in combination with at least one additional therapeutic agent that is cisplatin, carboplatin, an alkylating (e.g., methylating) agent, or a topoisomerase I inhibitor. In embodiments, a PARP inhibitor (e.g., niraparib) is administered in combination with radiation therapy.

In embodiments, a PARP inhibitor such as niraparib is administered to a patient simultaneously or sequentially with a chemotherapeutic agent. In some embodiments, a PARP inhibitor (e.g., niraparib) is administered before, during, or after administration of a chemotherapeutic agent. In embodiments, a chemotherapeutic agent is a platinum chemotherapeutic agent (e.g., cisplatin, carboplatin, oxaliplatin, nedaplatin, triplatin tetranitrate, phenanthriplatin, picoplatin, or satraplatin). In embodiments, a patient has a gynecological cancer (e.g., any gynecological cancer as described herein).

Immune Checkpoint Inhibitors

In embodiments, a PARP inhibitor (e.g., niraparib) is administered in combination (e.g., simultaneously or sequentially) with at an immune checkpoint inhibitor. In embodiments, a cancer patient is suffering or is at risk of non-small cell lung cancer (NSCLC).

In embodiments, an immune checkpoint inhibitor is an agent that inhibits programmed death-1 protein (PD-1) signaling, T-cell immunoglobulin domain and mucin domain 3 (TIM-3), cytotoxic T-lymphocyte-associated protein 4 (CTLA-4), lymphocyte activation gene-3 (LAG-3), or T cell immunoglobulin and ITIM domain (TIGIT).

In embodiments, an immune checkpoint inhibitor (e.g., an inhibitor of PD-1 signaling, TIM-3, CTLA-4, LAG-3, or TIGIT) is a protein, antibody, antisense molecule or small molecule. In embodiments, an immune checkpoint inhibitor is an antibody.

Inhibitors of PD-1 Signaling

In embodiments, a PARP inhibitor such as niraparib is administered to a patient in combination with (e.g., simultaneously or sequentially) with a PD-1 signaling inhibitor.

Inhibitors of PD-1 signaling for use in combination therapies of the present disclosure include those that bind to and block PD-1 receptors on T cells without triggering inhibitory signal transduction, agents that bind to PD-1 ligands to prevent their binding to PD-1, agents that do both, and agents that prevent expression of genes that encode either PD-1 or natural ligands of PD-1. Compounds that bind to natural ligands of PD-1 include PD-1 itself, as well as active fragments of PD-1, and in the case of the B7-H1 ligand, B7.1 proteins and fragments. Such antagonists include proteins, antibodies, anti-sense molecules and small organics.

In some embodiments, a PD-1 signaling inhibitor binds to PD-1. In some embodiments a PD-1 signaling inhibitor binds to PD-L1 or PD-L2 (e.g., human PD-L1 or human PD-L2).

In some embodiments, a PD-1 signaling inhibitor for use in combination therapies of the present disclosure is an antibody agent. In some embodiments, a PD-1 antibody agent binds an epitope of PD-1 which blocks the binding of PD-1 to any one or more of its putative ligands. In some embodiments, a PD-1 antibody agent binds an epitope of PD-1 which blocks the binding of PD-1 to two or more of its putative ligands. In an embodiment, a PD-1 antibody agent binds an epitope of a PD-1 protein which blocks the binding of PD-1 to PD-L1 and/or PD-L2. PD-1 antibody agents of the present disclosure may comprise a heavy chain constant region (Fc) of any suitable class. In some embodiments, a PD-1 antibody agent comprises a heavy chain constant region that is based upon wild-type IgG1, IgG2, or IgG4 antibodies, or variants thereof.

In some embodiments, a PD-1 signaling inhibitor is a monoclonal antibody, or a fragment thereof. In some embodiments, an antibody agent that inhibits PD-1 signaling is a PD-1 antibody or fragment thereof. Monoclonal antibodies that target PD-1 that have been tested in clinical studies and/or received marketing approval. Examples of antibody agents that target PD-1 signaling include, for example, any of the antibody agents listed in the following Table 1.

TABLE 1

| Antibody agents that target PD-1 | |
|---|---|
| Antibody Agent Target (Format) | Developer |
| Opdivo Nivolumab PD-1 (Human IgG4) | Bristol-Myers Squibb ONO |
| Keytruda Pembrolizumab PD-1 (Humanized IgG4) | Merck |
| Tecentriq Atezolizumab PD-L1 (Human IgG1) | Roche |
| Imfinzi Durvalumab PD-L1 (Human IgG1) | Astra Zeneca |
| Bavencio Avelumab PD-L1 (Human IgG1) | Merck KGaA/Pfizer |
| PDR001 PD-1 (Humanized IgG4) | Novartis |
| REGN2810 (SAR-439684) PD-1 (fully human IgG4) | Sanofi, Regeneron |
| BGB-A317 PD-1 (Humanized IgG4) engineered to not bind FcγRI | BeiGene |
| LY3300054 PD-L1 | Eli Lilly |
| BI 754091 (anti-PD-1) | Boehringer Ingelheim |
| IBI308 (anti-PD-1) | Innovent Biologics (Eli Lilly) |
| INCSHR-1210 (anti-PD-1) | Incyte |
| JNJ-63723283 (anti-PD-1) | Janssen Research & Development, LLC |
| JS-001 (anti-PD-1) | Shanghai Junshi Bioscience Co., Ltd. |
| MEDI0680 (AMP-514) anti-PD-1 (Humanized IgG4) | MedImmune Inc |
| MGA-012 (anti-PD-1) | MacroGenics |
| PF-06801591 (anti-PD-1) | Pfizer |
| REGN-2810 (anti-PD-1) | Regeneron |
| TSR-042 dostarlimab anti-PD-1 (Humanized IgG4) | TESARO |
| CX-072 anti-PD-L1 | CytomX Therapeutics |
| FAZ053 anti-PD-L1 | Novartis |
| PF-L1 millamolecule | Bristol-Myers Squibb |

PD-1 signaling inhibitors include those that bind to and block PD-1 receptors on T cells without triggering inhibitory signal transduction, agents that bind to PD-1 ligands to prevent their binding to PD-1, agents that do both and agents that prevent expression of genes that encode either PD-1 or natural ligands of PD-1. In some embodiments, an agent that inhibits PD-1 signaling is an antibody agent. Anti-PD-1 antibody agents can include any polypeptide or polypeptide complex that includes immunoglobulin structural elements sufficient to confer specific binding. Exemplary antibody agents include, but are not limited to, monoclonal antibodies, polyclonal antibodies, antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody agent that inhibits PD-1 signaling is a monoclonal antibody or a derivative thereof. In some embodiments, an antibody agent that inhibits PD-1 signaling is a PD-1 antibody, a PD-L1 antibody, or a derivative thereof. PD-1 and PD-L1 antibodies include, for example, atezolizumab, avelumab, BGB-A317, BI 754091, CX-072, durvalumab, FAZ053, IBI308, INCSHR-1210, JNJ-63723283, JS-001, LY3300054, MEDI-0680, MGA-012, nivolumab, PD-L1 millamolecule, PDR001, pembrolizumab, PF-06801591, REGN-2810, TSR-042 (dostarlimab), any of the antibodies disclosed in WO2014/179664, and any derivatives thereof. In embodiments, an agent includes combinations of agents that inhibit PD-1 signaling.

In embodiments, administration of a particular dose or cycle of a PARP inhibitor is separated in time from a particular dose or cycle of an agent that inhibits PD-1 signaling by a time period having a length that may be, for example, 1-minute, 5-minutes, 30-minutes, 1-hour, 2-hours, 5-hours, 10-hours, 12-hours, 24-hours, 48-hours, 72-hours, 96-hours, 1-week, 2-weeks, or more weeks. In some embodiments, the range may be bounded by a lower limit and an upper limit, the upper limit being larger than the lower limit. In some embodiments, the lower limit may be about 1-minute, about 5-minutes, about 15-minutes, about 30-minutes, about 45-minutes, about 1-hour, about 2-hours, about 4-hours, about 6-hours, about 12-hours, about 24-hours, about 48-hours, about 72-hours, about 96-hours, or about 1-week. In some embodiments, the upper limit may be about 2-weeks, about 3-weeks, about 4-weeks, about 5-weeks, about 6-weeks, about 8-weeks, or about 12-weeks. In some embodiments, the administration of a particular dose of a PARP inhibitor is separated in time from a particular dose of an agent that inhibits PD-1 signaling by a time period within the range of about 1-minute to about 12-weeks. In some embodiments, the range may be about 1-minute to about 8-weeks. In some embodiments, the range may be about 1-minute to about 6-weeks. In some embodiments, the range may be about 1-minute to about 4-weeks. In some embodiments, the range may be about 1-minute to about 2-weeks. In some embodiments, the range may be about 1-minute to about 1-week. In some embodiments, the range may be about 1-minute to about 96-hours. In some embodiments, the range may be about 1-minute to about 72-hours. In some embodiments, the range may be about 1-minute to about 48-hours. In some embodiments, the range may be about 1-minute to about 24-hours. In some embodiments, the range may be about 1-minute to about 12-hours. In some embodiments, the range may be about 1-minute to about 8-hours. In some embodiments, the range may be about 1-minute to about 4-hours. In some embodiments, the range may be about 1-minute to about 2-hours. In some embodiments, the range may be about 1-minute to about 1-hour. In some embodiments, the range may be about 1-minute to about 11 minutes.

In some embodiments, combination therapy with a PARP inhibitor and a PD-1 signaling inhibitor is administered to a patient or population of subjects who has exhibited response to prior therapy. In some embodiments, the patient or population of subjects has exhibited response to prior therapy with a chemotherapeutic agent. In some such embodiments, the chemotherapeutic agent is a platinum agent. In some embodiments, a platinum-based agent is selected from cisplatin, carboplatin, oxaliplatin, nedaplatin, triplatin tetranitrate, phenanthriplatin, picoplatin, or satraplatin.

In some embodiments, the regimen comprises at least one oral dose of a PARP inhibitor. In some embodiments, the regimen comprises a plurality of oral doses. In some embodiments, the regimen comprises once daily (QD) dosing. In some embodiments, a PARP inhibitor is administered on the first day of a 21-day cycle upon completion of infusion with a PD-1 signaling inhibitor. In some embodiments, a PARP inhibitor is administered daily throughout the regimen cycle at the same time every day. In some embodiments the same time every day is in the morning.

In some embodiments, the regimen comprises of one infusion of a PD-1 signaling inhibitor per regimen cycle. In some embodiments, the regimen comprises of one, 30-minute infusion of a PD-1 signaling inhibitor per regimen cycle. In some embodiments, the regimen comprises of one, 30-minute infusion of a PD-1 signaling inhibitor on the first day of each regimen cycle.

In some embodiments, the regimen comprises at least one 2-week to 8-week cycle. In some embodiments, the regimen comprises a plurality of 2-week to 8-week cycles. In some embodiments, the regimen comprises one 2-week to 8-week cycle. In some embodiments, the regimen comprises two 2-week to 8-week cycles. In some embodiments, the regimen comprises three or more 2-week to 8-week cycles. In some embodiments, the regimen comprises continuous 2-week to 8-week cycles.

In some embodiments, the regimen comprises at least one 28-day cycle. In some embodiments, the regimen comprises a plurality of 28-day cycles. In some embodiments, the regimen comprises one 28-day cycle. In some embodiments, the regimen comprises two 28-day cycles. In some embodiments, the regimen comprises three or more 28-day cycles. In some embodiments, the regimen comprises continuous 28-day cycles.

In some embodiments, the regimen comprises at least one 21-day cycle. In some embodiments, the regimen comprises a plurality of 21-day cycles. In some embodiments, the regimen comprises one 21-day cycle. In some embodiments, the regimen comprises two 21-day cycles. In some embodiments, the regimen comprises three or more 21-day cycles. In some embodiments, the regimen comprises continuous 21-day cycles.

In some embodiments, the regimen comprises a single infusion of at least 200 mg of a PD-1 signaling inhibitor. In some embodiments, the regimen comprises a single infusion of a PD-1 signaling inhibitor over a time period of at least 25-minutes, 30-minutes, 35-minutes, 40-minutes, or more. In some embodiments, the range may be bounded by a lower limit and an upper limit, the upper limit being larger than the lower limit. In some embodiments, the lower limit may be about 25-minutes, or about 30-minutes. In some embodiments, the upper limit may be about 35-minutes or about 40-minutes. In some embodiments, the range may be about 25-minutes to about 40-minutes. In some embodiments, the range may be about 25-minutes to about 35-minutes. In some embodiments, the range may be about 25-minutes to about 30-minutes. In some embodiments a PD-1 signaling inhibitor (e.g., pembrolizumab) is administered through intravenous (IV) infusion. In some embodiments an intravenous dose of a PD-1 signaling inhibitor (e.g., pembrolizumab) is administered in one or more unit dosage forms. In embodiments, a PD-1 signaling inhibitor is administered periodically to a subject at a dose of about 500 mg or about 1000 mg. In embodiments, a PD-1 signaling inhibitor is administered periodically to a subject at a dose of about 500 mg (e.g., once every three weeks (Q3W) and/or for 2, 3, 4, 5, 6, or more cycles). In embodiments, a PD-1 signaling inhibitor is administered periodically to a subject at a dose of about 1000 mg (e.g., once every three weeks (Q3W) and/or for 2, 3, 4, 5, 6, or more cycles). In embodiments, a PD-1 signaling inhibitor agent is administered to a subject at a dose of about 500 mg according once every three weeks (Q3W) for 3 cycles. In embodiments, a PD-1 signaling inhibitor is administered to a subject at a dose of about 500 mg according once every three weeks (Q3W) for 4 cycles. In embodiments, a PD-1 signaling inhibitor is administered to a subject at a dose of about 500 mg according once every three weeks (Q3W) for 5 cycles. In embodiments, a PD-1 signaling inhibitor is administered to a subject at a dose of about 1000 mg according once every six weeks or more (Q3W). In embodiments, a PD-1 signaling inhibitor is administered to a subject at a dose of about 1000 mg according once every six weeks (Q3W). In embodiments, a PD-1 signaling inhibitor is administered at a first dose of about 500 mg once every 3 weeks for 3 cycles followed by a second dose of about 1000 mg once every 6 weeks or more (e.g., until treatment is discontinued). In embodiments, a PD-1 signaling inhibitor is administered at a first dose of about 500 mg once every 3 weeks for 4 cycles followed by a second dose of about 1000 mg once every 6 weeks (e.g., until treatment is discontinued). In embodiments, a PD-1 signaling inhibitor is administered at a first dose of about 500 mg once every 3 weeks for 5 cycles followed by a second dose of about 1000 mg once every 6 weeks or more (e.g., until treatment is discontinued). In embodiments, a second dose is of about 1000 mg once every six weeks (e.g., until treatment is discontinued). In embodiments, a PD-1 signaling inhibitor is any anti-PD-1 antibody described herein. In various embodiments, the PD-1 signaling inhibitor is dostarlimab.

Niraparib

Niraparib, (3S)-3-[4-{7-(aminocarbonyl)-2H-indazol-2-yl}phenyl]piperidine, is an orally available, potent, poly (adenosine diphosphate [ADP]-ribose) polymerase (PARP)-1 and -2 inhibitor. See WO 2008/084261 (published on Jul. 17, 2008), WO 2009/087381 (published Jul. 16, 2009), and PCT/US17/40039 (filed Jun. 29, 2017), the entirety of each of which is hereby incorporated by reference. Niraparib can be prepared according to Scheme 1 of WO 2008/084261.

In some embodiments, niraparib can be prepared as a pharmaceutically acceptable salt. One of skill in the art will appreciate that such salt forms can exist as solvated or hydrated polymorphic forms. In some embodiments, niraparib is prepared in the form of a hydrate.

In certain embodiments, niraparib is prepared in the form of a tosylate salt. In some embodiments, niraparib is prepared in the form of a tosylate monohydrate. The chemical name of niraparib tosylate monohydrate is 2-{4-[(3S)-piperidin-3-yl]phenyl}-2Hindazole 7-carboxamide 4-methylbenzenesulfonate monohydrate. The molecular structure of the tosylate monohydrate salt of niraparib is shown below:

(1)

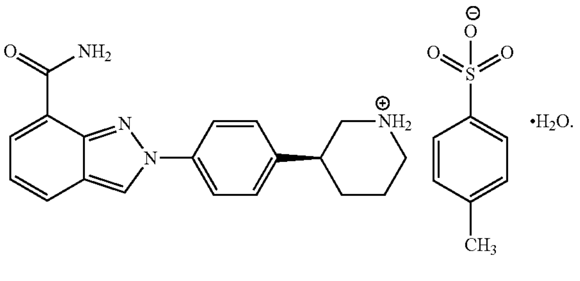

Niraparib is a potent and selective PARP-1 and PARP-2 inhibitor with inhibitory concentration at 50% of control ($IC_{50}$)=3.8 and 2.1 nM, respectively, and is at least 100-fold selective over other PARP-family members. Niraparib inhibits PARP activity, stimulated as a result of DNA damage caused by addition of hydrogen peroxide, in various cell lines with an $IC_{50}$ and an inhibitory concentration at 90% of control ($IC_{90}$) of about 4 and 50 nM, respectively.

Niraparib demonstrates selective anti-proliferative activity for cancer cell lines that have been silenced for BRCA-1 or BRCA-2, or carry BRCA-1 or BRCA-2 mutations compared to their wild type counterparts. The antiproliferative activity of niraparib on BRCA-defective cells is a consequence of a cell cycle arrest in G2/M followed by apoptosis. Niraparib can also be selectively cytotoxic for selected Ewing's sarcoma, acute lymphocytic leukemia (ALL), non-small cell lung cancer (NSCLC), and small cell lung cancer (SCLC) cell lines, as well as for tumor cell lines carrying homozygous inactivation of the ATM gene. Niraparib demonstrates weak activity on normal human cells. In vivo studies demonstrated strong antitumor activity with BRCA-1 mutant breast cancer (MDA-MB-436), BRCA-2 mutant pancreatic cancer (CAPAN-1), ATM-mutant mantle cell lymphoma (GRANTA-519), serous ovarian cancer (OVCAR3), colorectal cancer (HT29 and DLD-1), patient derived Ewing's sarcoma, and TNBC xenograft models in mice.

Olaparib

Olaparib acts as an inhibitor of the enzyme poly ADP ribose polymerase (PARP), and is termed a PARP inhibitor. The chemical name is 4-[(3-{[4-(cyclopropylcarbonyl)piperazin-1-yl]carbonyl}-4-fluorophenyl)methyl]phthalazin-1(2H)-one. Clinical trials of olaparib were initiated in breast, ovarian and colorectal cancer. Preliminary activity was seen in ovarian cancer, with 7 responses in 17 patients with BRCA1 or BRCA2 mutations and 11 responses in the 46 who did not have these mutations. However, an interim analysis of a phase II study that looked at using olaparib to maintain progression free survival or response after success with platinum-based chemotherapy indicated that a reported progression-free survival benefit was unlikely to translate into an overall survival benefit for the intent to treat populations. However, planned analysis of the subset of patients who had BRCA mutations found a clear advantage with olaparib (Ledermann et al., "Olaparib Maintenance Therapy in Platinum-Sensitive Relapsed Ovarian Cancer", *New England Journal of Medicine,* 366:1382-92 (2012); Ledermann et al., "Olaparib maintenance therapy in patients with platinum-sensitive relapsed serous ovarian cancer: a preplanned retrospective analysis of outcomes by BRCA status in a randomised phase 2 trial", *Lancet Oncol.* 15(8): 852-61 (2014)). Olaparib is approved as monotherapy, at a recommended dose of 400 mg taken twice per day, in germline BRCA mutated (gBRCAmut) advanced ovarian cancer that has received three or more prior lines of chemotherapy. BRCA1/2 mutations may be genetically predisposed to development of some forms of cancer, and may be resistant to other forms of cancer treatment. However, these cancers sometimes have a unique vulnerability, as the cancer cells have increased reliance on PARP to repair their DNA and enable them to continue dividing. This means that drugs which selectively inhibit PARP may be of benefit if the cancers are susceptible to this treatment. Thus, the olaparib clinical data demonstrated that PARP inhibitors would not be beneficial to prolong progression free survival in the treatment of cancer characterized by the absence of mutations in BRCA1 or BRCA2.

Rucaparib

Similarly, rucaparib acts as an inhibitor of the enzyme poly ADP ribose polymerase (PARP), and is also termed a PARP inhibitor. The chemical name of the commercial salt—rucaparib camsylate (per the "Rubraca" label)—is 8-fluoro-2-{4-[(methylamino)methyl]phenyl}-1,3,4,5-tetrahydro-6H-azepino[5,4,3-cd]indol-6-one ((1S,4R)-7,7-dimethyl-2-oxobicyclo[2.2.1]hept-1-yl)methanesulfonic acid salt. It is also approved as indicated as monotherapy for the treatment of patients with deleterious BRCA mutation (germline and/or somatic) associated advanced ovarian cancer who have been treated with two or more chemotherapies. The efficacy of rucaparib was investigated in 106 patients in two multicenter, single-arm, open-label clinical trials, Study 1 and Study 2, in patients with advanced BRCA-mutant ovarian cancer who had progressed after 2 or more prior chemotherapies. All 106 patients received rucaparib 600 mg orally twice daily as monotherapy until disease progression or unacceptable toxicity. Response assessment by independent radiology review was 42% (95% CI [32, 52]), with a median DOR of 6.7 months (95% CI [5.5, 11.1]). Investigator-assessed ORR was 66% (52/79; 95% CI [54, 76]) in platinum-sensitive patients, 25% (5/20; 95% CI [9, 49]) in platinum-resistant patients, and 0% (0/7; 95% CI [0, 41]) in platinum-refractory patients. ORR was similar for patients with a BRCA1 gene mutation or BRCA2 gene mutation. Thus, the rucaparib clinical data demonstrated that PARP inhibitors would not be beneficial to prolong progression free survival in the treatment of cancer characterized by the absence of mutations in BRCA1 or BRCA2.

Talazoparib

Similarly, talazoparib acts as an inhibitor of the enzyme poly ADP ribose polymerase (PARP), and is also termed a PARP inhibitor. The chemical name of talazoparib tosylate is (8S,9R)-5-Fluoro-8-(4-fluorophenyl)-9-(1-methyl-1H-1,2,4-triazol-5-yl)-2,7,8,9-tetrahydro-3H-pyrido[4,3,2-de]phthalazin-3-one 4-methylbenzenesulfonate (1:1). It is currently being evaluated in clinical studies for the treatment of patients with gBRCA mutated breast cancer (i.e., advanced breast cancer in patients whose BRCA genes contain germline mutations). The primary objective of the study is to compare PFS of patients treated with talazoparib as a monotherapy relative to those treated with protocol-specified physicians' choice.

Veliparib

Similarly, veliparib acts as an inhibitor of the enzyme poly ADP ribose polymerase (PARP), and is also termed a PARP inhibitor. The chemical name of veliparib is 2-[(R)-2-methylpyrrolidin-2-yl]-1H-benzimidazole-4-carboxamide.

Cancers

Non-limiting examples of cancers to be treated or characterized by the methods of the present disclosure can include melanoma (e.g., metastatic malignant melanoma), renal cancer (e.g. clear cell carcinoma), uterine cancers (e.g., uterine sarcoma or endometrial cancer), prostate cancer (e.g. hormone refractory prostate adenocarcinoma), gastrointestinal cancer, bladder cancer, pancreatic cancer, pancreatic adenocarcinoma, breast cancer, colon cancer, lung cancer (e.g. non-small cell lung cancer), esophageal cancer, squamous cell carcinoma, liver cancer, ovarian cancer, cervical cancer, thyroid cancer, head and neck cancer, glioblastoma, glioma, leukemia, lymphoma, mesothelioma, sarcoma and other neoplastic malignancies. Additionally, the invention includes refractory or recurrent malignancies whose growth may be inhibited using the methods of the invention. In some embodiments, a cancer to be treated by the methods of the present disclosure include, for example, carcinoma, squamous carcinoma (for example, cervical canal, eyelid, tunica conjunctiva, vagina, lung, oral cavity, skin, urinary bladder, head and neck, tongue, larynx, and gullet), and adenocarcinoma (for example, prostate, small intestine, endometrium, cervical canal, large intestine, lung, pancreas, gullet, intestinum rectum, uterus, stomach, mammary gland, and ovary). In some embodiments, a cancer to be treated by the methods of the present disclosure further include sarcomata (for example, myogenic sarcoma), leukosis, neuroma, melanoma, and lymphoma.

In embodiments, a cancer is a cancer such as adenocarcinoma, adenocarcinoma of the lung, pancreatic adenocarcinoma, adrenocortical carcinoma, anal cancer, appendiceal cancer, bladder cancer, brain cancer, breast cancer (e.g., triple negative breast cancer (TNBC)), cancer of the fallopian tube(s), cancer of the testes, cerebral cancer, cervical cancer, choriocarcinoma, colon adenocarcinoma, colon cancer, colorectal cancer, endometrial cancer, epithelial cancer, esophageal cancer, Ewing's sarcoma, follicular lymphoma ("FL"), gall bladder cancer, gastric cancer, gastrointestinal cancer, glioma, head and neck cancer, hepatocellular cancer, kidney cancer, kidney clear cell cancer, laryngeal cancer, leukemia, liver cancer, lung cancer, lymphoma, melanoma, Merkel cell carcinoma, mesothelioma, monocytic leukemia, multiple myeloma, myeloma, a neuroblastic-derived CNS tumor, non-small cell lung cancer (NSCLC), oral cancer, ovarian cancer, ovarian carcinoma, pancreatic cancer, peritoneal cancer, primary peritoneal cancer, prostate cancer, relapsed or refractory classic Hodgkin's Lymphoma (cHL), renal cell carcinoma, rectal cancer, salivary gland cancer (e.g., a salivary gland tumor), sarcoma, skin cancer, small cell lung cancer, small intestine cancer, squamous cell carcinoma of the anogenital region, squamous cell carcinoma of the esophagus, squamous cell carcinoma of the head and neck (SCHNC), squamous cell carcinoma of the lung, stomach cancer, thymic cancer, a thymoma, thyroid cancer, uveal melanoma, urothelial cell carcinoma, uterine cancer, uterine endometrial cancer, uterine sarcoma, vaginal cancer, or vulvar cancer.

In embodiments, a cancer is bladder cancer, breast cancer (e.g., triple negative breast cancer (TNBC)), cancer of the fallopian tube(s), cholagiocarcinoma, colon adenocarcinoma, endometrial cancer, esophageal cancer, Ewing's sarcoma, gastric cancer, kidney clear cell cancer, lung cancer (e.g., lung adenocarcinoma or lung squamous cell cancer), mesothelioma, ovarian cancer, pancreatic cancer, peritoneal cancer, prostate cancer, uterine endometrial cancer, or uveal melanoma. In embodiments, a cancer is ovarian cancer, cancer of the fallopian tube(s), or peritoneal cancer. In embodiments, a cancer is breast cancer (e.g., TNBC). In embodiments, a cancer is lung cancer (e.g., non-small cell lung cancer). In embodiments, a cancer is prostate cancer.

In embodiments, a cancer is a solid tumor such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms tumor, cervical cancer, uterine cancer, testicular cancer, non-small cell lung cancer (NSCLC), small cell lung carcinoma, bladder carcinoma, lung cancer, epithelial carcinoma, skin cancer, melanoma, neuroblastoma, or retinoblastoma In embodiments a cancer is a lymphoma such as Hodgkin's disease, non-Hodgkin's Lymphoma, multiple myeloma, Waldenstrom's macroglobulinemia, heavy chain disease, and polycythemia vera.

In embodiments, a cancer is a CNS or brain cancer such as glioma, pilocytic astrocytoma, astrocytoma, anaplastic astrocytoma, glioblastoma multiforme, medulloblastoma, craniopharyngioma, ependymoma, pinealoma, hemangioblastoma, acoustic neuroma, oligodendroglioma, meningioma, vestibular schwannoma, adenoma, metastatic brain tumor, meningioma, spinal tumor, or medulloblastoma.

In some embodiments, such cancers are selected from gynecologic cancers (i.e., cancers of the female reproductive system such as ovarian cancer, fallopian tube cancer, cervical cancer, vaginal cancer, vulvar cancer, uterine cancer, or primary peritoneal cancer). In some embodiments, cancers of the female reproductive system include, but are not limited to, ovarian cancer, cancer of the fallopian tube(s), peritoneal cancer and breast cancer. In some embodiments, an ovarian cancer is an epithelial carcinoma. Epithelial carcinomas make up 85% to 90% of ovarian cancers. While historically considered to start on the surface of the ovary, new evidence suggests at least some ovarian cancer begins in special cells in a part of the fallopian tube. The fallopian tubes are small ducts that link a woman's ovaries to her uterus that are a part of a woman's reproductive system. In a normal female reproductive system, there are two fallopian tubes, one located on each side of the uterus. Cancer cells that begin in the fallopian tube may go to the surface of the ovary early on. The term "ovarian cancer" is often used to describe epithelial cancers that begin in the ovary, in the fallopian tube, and from the lining of the abdominal cavity, call the peritoneum. In some embodiments, the cancer is or comprises a germ cell tumor. Germ cell tumors are a type of ovarian cancer develops in the egg-producing cells of the ovaries. In some embodiments, a cancer is or comprises a stromal tumor. Stromal tumors develop in the connective tissue cells that hold the ovaries together, which sometimes is the tissue that makes female hormones called estrogen. In some embodiments, a cancer is or comprises a granulosa cell tumor. Granulosa cell tumors may secrete estrogen resulting in unusual vaginal bleeding at the time of diagnosis. In some embodiments, a gynecologic cancer is associated with homologous recombination repair deficiency/homologous repair deficiency ("HRD") and/or BRCA1/2 mutation(s). In some embodiments, a gynecologic cancer is platinum-sensitive. In some embodiments, a gynecologic cancer has responded to a platinum-based therapy. In some embodiments, a gynecologic cancer has developed resistance to a platinum-based therapy. In some embodiments, a gynecologic cancer has at one time shown a partial or complete response to platinum-based therapy (e.g., a partial or complete response to the last platinum-based therapy or to the penultimate platinum-based therapy). In some embodiments, a gynecologic cancer is now resistant to platinum-based therapy.

In embodiments, a cancer is metastatic. In some embodiments, a gynecological cancer (e.g., ovarian cancer) is metastatic. In some embodiments, a gynecological cancer (e.g., ovarian cancer) is an advanced gynecological cancer (e.g., ovarian cancer). In some embodiments, a cancer is a stage II, stage III or stage IV gynecological cancer (e.g., ovarian cancer).

In embodiments, a cancer is a recurrent cancer (e.g., a recurrent gynecological cancer such as recurrent epithelial ovarian cancer, recurrent fallopian tube cancer, or recurrent primary peritoneal cancer).

In embodiments, a cancer is an advanced cancer.

In embodiments, a cancer is characterized by a mutation in one or more genes. In some embodiments, the cancer is characterized by an ATM and/or BAP1 mutation.

In embodiments, a cancer is pancreatic cancer, melanoma, liver cancer, cervical cancer, gastric cancer, uterine cancer, or lung cancer. In some embodiments, a pancreatic cancer, melanoma, liver cancer, cervical cancer, gastric cancer, uterine cancer, or lung cancer is characterized by a bi-allelic mutation. In some embodiments, a pancreatic cancer, melanoma, liver cancer, cervical cancer, gastric cancer, uterine cancer, or lung cancer is characterized by a functional bi-allelic mutation.

In embodiments, a cancer is pancreatic cancer. In some embodiments, the pancreatic cancer is characterized by a BRCA2 mutation. In further embodiments, the BRCA2 mutation is bi-allelic.

In embodiments, a cancer is melanoma. In some embodiments, the melanoma is characterized by a BAP1 mutation. In further embodiments, the BAP1 mutation is bi-allelic.

In embodiments, a cancer is liver cancer. In some embodiments, the liver cancer is characterized by a BAP1 mutation. In further embodiments, the BAP1 mutation is bi-allelic.

In embodiments, a cancer is cervical cancer. In some embodiments, the cervical cancer is characterized by a BAP1 mutation. In further embodiments, the BAP1 mutation is bi-allelic.

In embodiments, a cancer is uterine cancer. In some embodiments, the uterine cancer is characterized by a BAP1 mutation. In further embodiments, the BAP1 mutation is bi-allelic. In some embodiments, the uterine cancer is characterized by a ATM mutation. In further embodiments, the ATM mutation is bi-allelic. In some embodiments, the uterine cancer is characterized by a BRCA1/2 mutation. In further embodiments, the BRCA1/2 mutation is bi-allelic.

In embodiments, a cancer is gastric cancer. In some embodiments, the gastric cancer is characterized by a BAP1 mutation. In further embodiments, the BAP1 mutation is bi-allelic.

In embodiments, the administration is according to a regimen that achieves any one of or combination of: prolonged progression free survival; reduced hazard ratio for disease progression or death; and/or prolonged overall survival or a positive overall response rate (e.g., a regimen as described herein).

EXAMPLES

The application may be better understood by reference to the following non-limiting examples, which are provided as exemplary embodiments of the invention disclosed in the present application. The following examples are presented in order to more fully illustrate embodiments and should in no way be construed, however, as limiting the broad scope of the application or the invention as described or claimed herein. While certain embodiments of the present application (or invention) have been shown and described herein, it will be obvious that such embodiments are provided by way of example only. Numerous variations, changes, and substitutions may occur to those skilled in the art without departing from the spirit and scope of the invention. It should be understood that various alternatives to the embodiments described herein may be employed in practicing the methods and/or other aspects or embodiments described herein.

Example 1—Classification of Cancer Samples Based on Homologous Recombination Deficiency Status Histopathology images (H&E stained) from 866 breast cancer samples with corresponding whole-exon sequencing (WES) data and Affymetrix Genome-Wide Human SNP Array 6.0data were obtained from The Cancer Genome Atlas (TCGA). The dataset can be downloaded from the GDC data portal (https://portal.gdc.cancer.gov/), selecting TCGA-BRCA. Signature 3 score, LST score, NtAI score, LOH score, fLOH score, and HRD score (sum of NtAI, LOH, and LST scores) for all of the samples were determined from the provided values in the TCGA dataset.

The Signature 3 score in these Examples was from a de-novo mutational signature analysis performed for the composite features of single base substitutions (SBS) and insertions and deletions (indels) in the TCGA-BRCA samples. The mutation count matrix of 96 base substitution types and 20 indel features stratified by the number of inserted or deleted bases up to 10 base-pairs were ingested into the Bayesian variant of non-negative matrix factorization algorithm (SignatureAnalyzer; https://software.broadinstitute.org/cancer/cga/msp) to define a composite version of Signature 3 characterized by a broad spectrum of base substitutions and enriched deletions ≥10 base-pairs. The Signature 3 score, defined as the number of mutations attributed to this composite version of Signature 3, was significantly enriched in the putative HRD samples with bi-allelic inactivation in BRCA1, BRCA2, PALB2, and RAD51C.

The use of the conventional (known) Signature 3 score method may also be used and is expected to produce acceptable results.

Ground truth homologous recombination deficient samples for a training set were selected by identifying 18 samples with BRCA1 germline bi-allelic deleterious mutations and 9 samples with BRCA2 germline bi-allelic deleterious mutations. 172 ground truth homologous recombination proficient samples for the training set were randomly selected from 344 samples identified with no or low homologous recombination deficient events (HRD score less than 20) and with the low Signature 3 score (Signature 3 score less than 20). Features for the training set were defined as (1) Signature 3 score, (2) LST score, (3) NtAI score, (4) LOH score, and (5) fLOH score. A LASSO logistic regression (GLMNET R package) was used to train a classification algorithm/model and weight the features using the training set. Signature 3 was weighted at about 3.67 and LST score at about 0.368. NtAI, LOH, and fLOH scores were weighted as 0, and were therefore ignored by the trained classification algorithm/model.

To evaluate the trained classification model, a validation set was formed from other samples in the TCGA sample set by labeling 9 samples with BRCA1 somatic bi-allelic inactivation and 7 samples with BRCA2 somatic bi-allelic inactivation as homologous recombination deficient, and the 172 remaining samples from the afore-mentioned pool of 344 samples identified with no or low homologous recombination deficient events and the low Signature 3 score were labeled as homologous recombination proficient. The validation set data was then inputted into the trained classification algorithm/model, and successfully predicted the 16 labeled homologous recombination deficient samples as homologous recombination deficient, and the 172 labeled homologous recombination proficient samples as homologous recombination proficient. So, the classification model trained with only germline bi-allelic inactivation samples labelled as HRD correctly identified the somatic bi-allelic inactivation mutants as HRD (HRD=LASSO probability >0.7 (=HRD probability >0.7)).

The training set and validation set were combined (40 of the 43 BRCA1 or BRCA2 bi-allelic germline or somatic deleterious mutation samples labeled homologous recombination deficient (with 3 samples having both germline and somatic mutations) and the 344 samples labeled as homologous recombination proficient and used to re-train the classification algorithm. This was to build a more robust classification model. Signature 3 was weighted at about 4.37 and LST score at about 0.201. NtAI, LOH, and LOH_frac_altered scores were weighted as 0, and were therefore ignored by the trained classification algorithm.

Figure 6:
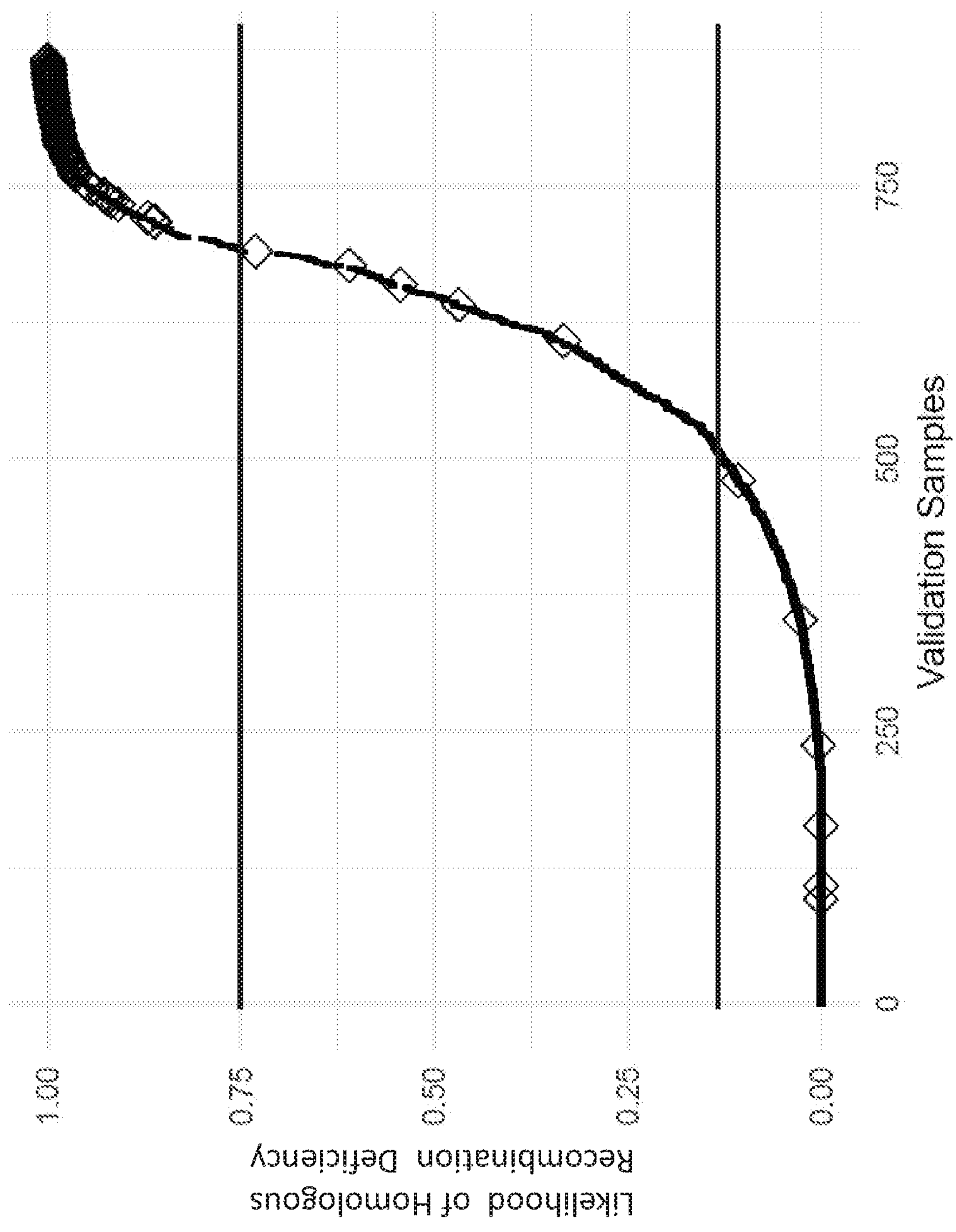
FIG. 6 shows the classification results of unlabeled cancers, wherein features (signature 3 score and HRD score) associated with the unlabeled cancers were inputted into a trained classification model.

The 866 samples from the TCGA were inputted as an unlabeled test set into the re-trained classification model, and the homologous recombination deficiency (HRD) likelihood for each cancer was determined (see FIG. 6). In more detail, FIG. 6 is a fitted logistic (S-shaped) curve that shows the calculated likelihood (Y-axis) of a sample being HRD (the likelihood being the HRD (LASSO) probability in a numeric range of 0-1; a higher value meaning a higher probability of a sample being HRD and a lower value meaning a higher probability of a sample being HRP). The samples in the test set are arranged along the X-axis in order of increasing HRD probability so the samples predicted to be HRD with a high probability are clustered (or classified) to the top right-hand corner of the plot (nearer Y=1.0=HRD) and the samples predicted to be HRD with a low probability (i.e. predicted to be HRP with a high probability (HRP probability=1−HRD probability)) are clustered (classified) to the bottom left-hand of the plot (nearer Y=0=HRP).

Samples with a homologous recombination deficiency likelihood greater than 0.75 were labeled (or classified) as homologous recombination deficient (n=172), and samples with a homologous recombination deficiency likelihood less than 0.125 (n=approximately 500) were labeled (or classified) as homologous recombination proficient. This is shown in FIG. 6.

This thresholding (or filtering) of the full 866 TCGA sample set (for HRD and HRP labelling/classification) results in a sample (sub-)set which more likely excludes false positives and false negatives; e.g. as may be the case for samples in the range between the threshold values (0.125-0.75).

The labels (or classification) for this sample sub-set can be used to label (as HRD or HRP or some other related classification; i.e. class 1 and class 0) the associated histopathology slide images for the TCGA samples in the sub-set, which labelled images can then be used as the training set for supervised training of a (machine) learning model (of any type, including those disclosed elsewhere herein) to predict or characterize or classify or diagnose the HRD status of a cancer from an associated image of the cancer, e.g. a histopathology image.

The use of HRD probability values above 0.75 and below 0.125 (or other selected thresholds) to define a training set of cancer images means the labelling in the training set is more accurate (a good ground truth, especially where a real ground truth is not known definitively) and thus meaning the trained learning model generated with that training image set should be more accurate than with poorly labelled training images.

It will be appreciated that other threshold values for HRD and HRP sampling could be selected to further minimize errors in the labelling, especially if there is a large dataset (in which case the threshold limit could be some other value higher than 0.75 for HRD, for instance in the range 0.8-1.0, 0.85-1.0, 0.9-1.0, 0.95-1.0, etc., and lower than 0.125 for HRP, for instance in the range 0-0.10, 0-0.075, 0-0.05, 0-0.025, etc.).

It will also be appreciated that this method of Example 1 enabled a larger set of samples in the TCGA sample set to be labelled as HRD than relying solely on the 40 BRCA1/2 mutation samples, which can be useful when creating a training data set for a (machine) learning model, such as disclosed elsewhere herein, since trained learning models can be expected to improve with increased amount of training data.

Example 2—Generation of a Training Image Data Using Consensus Labeling

Example 2 is based on the same TCGA dataset as used in Example 1. Consensus labeling is an extension of the LASSO regression described in Example 1. The 40 samples with BRCA1 and/or BRCA2 bi-allelic deleterious mutations were used to define the homologous recombination deficient group of (ground truth) samples in the full TCGA sample set. For the remaining set of samples of the TCGA sample set, a variety of different thresholds for the HRD score and Signature 3 features were used to define which of them would be the homologous recombination proficient (ground truth) samples (rather than a predetermined threshold of HRD score and Signature 3 score, as in Example 1 (where the thresholds were both set to be less than 20).

In more detail, for each selected pair of threshold values for HRD score and Signature 3 (herein a "threshold pair") only those samples in the remaining sample set satisfying the threshold pair are labelled as corresponding to HRP. Thus, for each different threshold pair, there are the same 40 ground truth samples for HRD as described above and a number of samples* labelled as HRP depending on the threshold pair values (* which understandably can differ between threshold pairs).

The HRD score for the threshold pairs was selected from the HRD threshold range of 10-50 (inclusive) and the Signature 3 score selected for the threshold pairs was selected from the Signature 3 threshold range of 10-50 (inclusive), using an increment of 4 for values selected from these threshold ranges (11 values in each range). These features were selected because HRD score and the Signature 3 score correlate well to HRD status.

In an alternative embodiment of this example, the HRD score for the threshold pairs is selected from the HRD threshold range of 10-42 and the Signature 3 score selected from the range 1-30, using an increment of 2. The HRD score range reflects that an HRD score of 42 is known as a cut-off between samples which are HRD or HRP (e.g. the "MyChoice" diagnostic test described herein).

LASSO regression was used to estimate β (feature weights) for all features (Signature 3 score, LST score, NtAI score, LOH score, HRD score, and fLOH) using different feature thresholds to define the homologous recombination proficient ground truth. In other words, for each different threshold pair, LASSO logistic regression (GLMNET R package) was used to train a classification algorithm/model and weight the features using the HRD and HRP ground truth training set of samples belonging to the threshold pair. So, a separate classification model was trained for each threshold pair using the associated ground truth samples. Signature 3 and LST were determined to be the two features contributing to predict homologous recombination deficiency status consistently across all thresholds tested (in this Example, 121 different threshold pairs were used, although other numbers may be used, including a higher number of different threshold pairs).

For every pair of thresholds for Signature 3 score and HRD score, estimated β for Signature 3 and LST were used to calculate likelihood of homologous recombination deficiency for each sample In other words, the trained classification model from each threshold pair was applied to all 866 samples in the TCGA data set to predict HRD probability for each of the 866 samples (a logistic curve of the type shown in FIG. 6).

A heatmap was used to show each sample's likelihood of HR deficiency at each pair of thresholds used to define the homologous recombination proficient group. Each column of the grid-like heatmap represented a pair of thresholds and each row represented one sample from the full (866) TCGA dataset. The HRD probability for each sample at each threshold pair is populated into the respective cell. Specifically, a color-code key is assigned to different ranges of HRD probability the HRD probability. The HRD probability for each sample at each threshold pair is then shown by the appropriate colour (for the range in which the HRD probability sit) in the relevant heatmap cell. The HRD probability ranges were for each 0.1 increment of the full HRD range 0-1 (i.e. first sub-range 0-0.1 being a first colour, second sub-range 0.1-0.2 being a second, different colour, . . . and the final sub-range 0.9-1.0 being a final, different colour). The heatmap provided a visible indication of which of the TCGA samples were consistently, for all threshold pairs, predicted to be HRD at with a high probability and were consistently HRP with a high probability (i.e. a low HRD probability).

Samples consistently predicted as HR proficient group were labeled (or classified) as HR proficiency and samples consistently predicted as HR deficient group was labeled (or classified) as HR deficiency. A final round of LASSO logistic regression was then performed with a training set comprised of the same 40 HRD samples used in the other training sets and the 427 HRP samples in the TCGA full (866) sample set which, for all threshold pairs, are below a threshold HRD probability (here, less than 0.25). This final round of LASSO logistic regression was to determine the most relevant features and corresponding weights for the final classification model. As a result, Signature 3 was weighted at about 6.08 and LST score at about 1.72, while four other features of HRD score and NtAI, LOH, and fLOH scores were weighted as 0, and were therefore ignored by the trained classification model. The model was sufficient to identify all BRCA1/2 bi-allelic mutations (HRD probability cut-off >0.5)

The trained classification model from this final round of training was then applied to the full (866) TCGA sample set. A characteristic logistic curve shows the HRD probabilities for each sample (similar to FIG. 6). A threshold for HRD probability can then be used to select TCGA cancer samples whose corresponding slides can be labelled as HRD or HRP (or some other assign) to create a training set of cancer images for training a machine learning model to determine the HRD status of a cancer from its image, such as in Example 3 infra.

With the HRD probability cut-off above 0.7 for HRD the model correctly identified two non-BRCA bi-allelic mutations (each in RAD51C and PALB2), all eight homozygous deletions, 14 of 19 RAD51C and 23 of 26 BRCA1 epigenetic silencing events. Also, the model correctly identified, as HRP, 4 of 6 mono-allelic mutants (1 in BRCA1 and 3 out of 4 in BRCA2). The model explained 97% of bi-allelic mutations, deletions, and epigenetic silencing with LOH (84 out of 87) and identified additional 97 putative HR-deficient samples with no clear events in four HR-related genes with a HRD probability exceeding 0.7.

The advantages of the method of Example 2 are the same as Example 1 (including increasing the number of accurately labeled or classified samples which can be used for a training set for a (machine) learning model, especially for HRD), with the additional advantage that consensus labelling (using various threshold pairs) provides greater confidence in the accuracy of the labelling or classification of samples as HRD and, especially of HRP.

The performance of the final classification model created by consensus labelling was independently tested with the data in the HRDetect paper (Davies et al., *HRDetect is a predictor of BRCA1 and BRCA2 deficiency based on mutational signatures, Nature Medicine*, vol. 23, pp. 512-525 (2017). The receiving operator characteristic (ROC) graph not shown—showed that the model had good performance, achieving 92% sensitivity at 98% specificity in this evaluation with a different dataset.

It will be understood that the technique of consensus labelling as described in this Example (and as otherwise more generally disclosed herein) can be used to identity (putative) ground truth examples in other datasets, including other cancer dataset with a characteristic, property or status (e.g. which can be classified into a set of two (binary) or more (multi-class) classes, which ground truths may then be used for a training set (e.g. of related images) for training a machine learning model (e.g. an image classification model), as for example shown by Example 6.

Example 3—Characterizing Homologous Recombination Deficiency Status

From the afore-mentioned full (866) TCGA data set, those TCGA samples calculated by the final LASSO regression classification model of Example 2 (consensus labelling) to have a HRD probability of above 0.75 were assigned the label 'HRD' and those less than 0.125 were assigned the label 'HRP' (as can be understood by reference to FIG. 6). The histology (or histopathology) images (H&E stained)—whole slide images—of these labelled cancer samples (where available in the TCGA dataset, which was not always the case) formed training data for training the Inception v3 image recognition model to recognize HRD status of a cancer from an image (histology slide image) of the cancer. As known in the art, the training data was randomly split 70:30 (in each label class) into a training set and a hold-out set.

112 breast cancer histology images labeled as homologous recombination deficient and 313 breast cancer histology images labeled as homologous recombination proficient were used to train an Inception v3 classification model (version 2016-03-0). This is the training set (after the split).

Inception v3 is a widely-used image recognition model of Google's that has been trained on the original ImageNet image dataset (http://image-net.org/index). The Inception v3 classification model is embodied in a deep learning artificial neural network of the convolutional type (called a "convolutional neural network" or "CNN"). Inception v3 is based on the original paper *Rethinking the Inception Architecture*

*for Computer Vision* (11 Dec. 2015) by Szegedy et al (https://arxiv.org/pdf/1512.00567.pdf).

Further details on Inception v3 are widely available on the internet, such as at:

https://cloud.google.comApu/docs/inception-v3-advanced (advanced guide), https://github.comAensorflow/tpu/tree/master/models/experimental/inception (working code), and https://cloud.google.comApu/docs/tutorials/inception (tutorial).

This Example implemented the "DeepPath" code base (including linked libraries and code (including Inception v3 and OpenSlide)) using TensorFlow 1.0 (however other implementations can be used). This can be found at https://github.com/ncoudray/DeepPATH and was developed by Coudary et al to apply the Inception v3 CNN to classification of non-small lung cancers using histopathology images. This Example 3 followed the approach described by Coudary et al in the companion publication Coudray N et al, *Classification and mutation prediction from non-small lung cancer histopathology image using deep learning, Nature Medicine,* 1559-1567 (2018), the contents of which are incorporated herein by reference.

The aforementioned labelled TCGA images were divided into 512×512 pixel tiles (non-overlapping) using a digital magnification power of 5× or 20×. This is because the TCGA training images are labelled at the whole slide level, but a typical whole slide image (WSI) has far too many pixels for available deep learning technology to process. Moreover, the size of the WSIs are too large for direct input to Inception v3.

The DeepPath code base includes the code for associating or aggregating the tiles of a parent WSI so the processing of the tiles can be related back to the parent WSI. Each tile of a slide image is assign the same training label as its parent slide and the HRD probability for a slide is determined by averaging the HRD probabilities of its tiles. See also Coudray. Other tiling (including known) approaches could be used.

The Inception v3 classification model used in this Example 3 was pre-trained using images not related to cancer images before training with the labeled training image data. These were the ImageNet images, as mentioned above. In other words, the Inception v3 model was partially (re-)trained with the labelled TCGA images (widely known as "transfer learning" in the machine/deep learning field), as often used in artificial (deep) neural networks for image analysis since the pre-trained model is able (in its upstream layers) to detect generically-applicable, low-level image features (such as edges and curves). Transfer learning results in the final layer(s) or head of the network being (re-)trained to identify the model weights which are more specific to the new training images (features or pixel patterns therein) and for classification rules based on those new training images. So, in the present Example 3, the Inception v3 model pre-trained with, and having model weights derived from, the ImageNet images was used for the base model architecture, and the head of the neural network architecture (customized classification layers) was removed for (re-)training. For (re-)training, the head was randomly initialized and a slow learning rate (0.0001) selected because the model weights of the base architecture were already in a good state to recognize basic features of images (see above).

As regards other hyperparameters and user settings for the Inception v3 architecture, these were as used or set in DeepPath; for example: batch size=64; batch normalization layers using momentum=0.9997; convolution 2D and dense layers initialized with: kernel_regularizer=tf.keras.regularizers.l2(0.00004); RMSprop optimizer with parameters: learning rate=0.0001, rho=0.9, momentum=0.9, epsilon=1.0; and exponential decay applied to learning rate with decay batch steps=1000 and decay rate=0.16.

So, to summarize, pre-trained Inception v3 model was (re-)trained using the TCGA training image set indicated above for a number of (e.g. 25 thousand (25 k)) training cycles.

To evaluate or test the trained Inception v3 HRD classification model resulting from the (re-)training the hold-out set of training data was input to the model (herein called the 'validation set', but can also be called the 'test set'). The validation set (with 49 breast cancer histology images previously identified as homologous recombination deficient and 135 breast cancer histology images previously identified as homologous recombination proficient) were characterized using the trained classification model.

Figure 7:
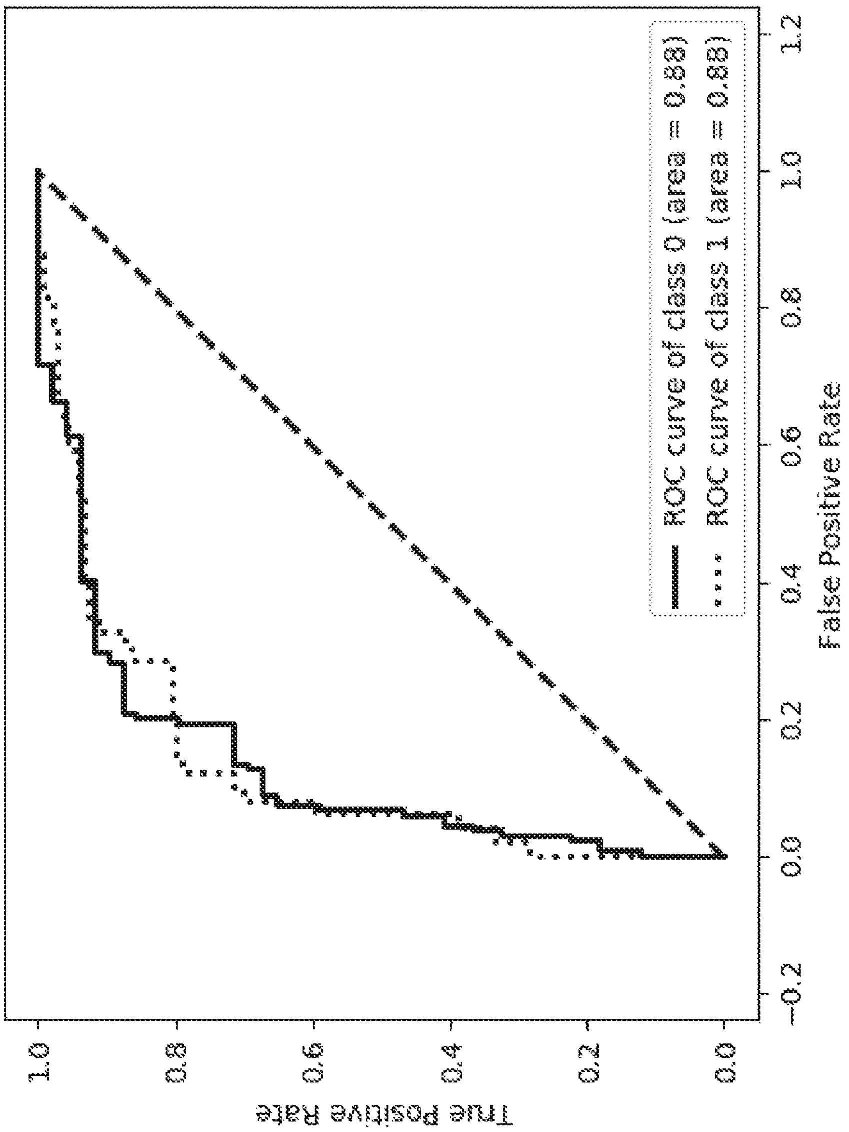
FIG. 7 shows an ROC curve for an image classifier configured to classify images of cancer into a homologous recombination deficient class or a homologous recombination proficient class.

A receiver operating characteristic (ROC) analysis for images in the validation set with a magnification power of 5× is shown in FIG. 7. The area of the ROC curve for HR deficient classification (class 0) and the area of the ROC curve for HR proficient classification (class 1) were both about 0.88. This shows the Inception v3 classification model trained to classify the HRD status of a cancer (in this case breast cancer) from an image of the cancer (in this case a histology image).

Example 4—TensorFlow 2 for Inception v3

This Example was a modification of Example 3, using the TensorFlow 2.0 neural network framework library (published by Google and freely downloadable) for implementing the image classification of the TCGA breast cancer whole slide images with the pre-trained (with ImageNet) Inception v3 model. The model settings were as set out in Example 3.

In this Example, the identification and labelling of the training data images (HRD or HRP) was also based on consensus labelling, albeit using the narrower ranges for the different threshold pairs (see Example 2) and selecting those TCGA samples run through the final LASSO classification model with HRD probability thresholds of above 0.95 (=HRD=186 samples) and below 0.05 (=HRP=558 samples). The training image data (cancer image slides) was randomly split 70%:15%:15% into respective training, validation (for hyperparameter tuning) and test splits.

In an embodiment of this Example, Vahadane stain normalization was used, training was for 15 thousand (15 k) cycles (as optimized with the validation set) and the test set was increased to include image samples having an HRD probability between the above-mentioned thresholds for HRD and HRP (i.e. in the range 0.05-0.95). Other thresholds for selecting the training image data, and thus the gap to select samples to increase the test set, may be used.

Performance of the trained Inception v3 model per this Example on the test sets was evaluated by ROC curves and was seen to be similar to Example 3 (similar to that shown in FIG. 7), with ROC-AUC in the range of 0.8-0.91 for the test sets.

Example 5—Other Deep Learning Architectures

Example 5A—VGG

A different trained deep learning model was developed by transfer learning using a VGG model (in this case VGG-16), as implemented on the PyTorch platform. The VGG-16 model is based on another widely-known convolutional neural network suitable for image classification tasks (developed by the Visual Geometry Group (VGG) at the University of Oxford). The VGG-16 models has initial model weights based on its training with the ImageNet images (the pre-trained model). The tiling of the slide images was done with DeepPath.

As in Examples 3 and 5, a sub-set of the TCGA breast cancer whole slide images are labelled as HRD or HRP by utilizing the consensus labelling described in Example 2, and used as the training image data to (re-)train the head of the VGG model to be able to classify a whole slide image of breast cancer as HRD or HRP. The training data is randomly split 70%:15%:15% into respective training, validation (for hyperparameter tuning) and test sets. The test set was also increased (to make a further test set) to include images of TCGA samples with an HRD probability (determined by the final LASSO classification model) between the thresholds used to select the HRD and HRP samples for the training image data Performance of the trained VGG-16 model per this Example on the test sets was evaluated by ROC curves and considered not as good as the models of Examples 3, 4 and 5A.

ResNet

A different trained deep learning model was developed by transfer learning using a ResNet model (deep Residual Network; in this case ResNet34). This model is embodied in another widely-known convolutional neural network suitable for image classification tasks. The ResNet34 model used had been pre-trained with the ImageNet images. The ResNet architecture and algorithmic methods therein are described for instance at http://openaccess.thecvf.com/content_cvpr_2016/papers/He_Deep_Residual_Learning_CVPR_2016_paper.pdf.

PyTorch and the Fast.AI library (www.fastai) were used for the image classification with the ResNet34 model. The tiling of the slide images was done with DeepPath.

The training data—and the random split into training, validation and test sets—for this Example was as described in Example 3 (consensus labelling following the approach of Example 2). A further test set was also prepared in the manner described in Examples 4 and 5A. Performance of the trained ResNet model on the test sets, as evaluated with ROC curves, was considered comparable to the performance of Inception v3 (similar to what is shown in FIG. 7), with ROC-AUC in the range of 0.79-0.87 for the test sets.

In terms of specific details, the ResNet implementation involved:

- Training the neural net by freezing all base architecture layers for 5 epochs with the learning rate identified using lr_find in Fast.AI (learning rate=0.01). The weight of the randomly initiated classification layers were tuned first.
- After training the classification layers, unfreeze the whole neural net, and train the neural net in the following fashion:
  - Using the discriminative learning rate identified by lr_find from Fast.AI. It starts with a learning rate range=(1e-6, 1e-4) for the first epoch. It means the first layer uses the lower learning rate, i.e. 1e-6 and the final layer uses the larger learning rate, i.e. 1e-4. Other layers in between are given a learning rate between these two numbers with a multiplicative interpolation.
  - The learning rate range decays after every 10 epochs, with a decay rate of 0.16. For example, after the first 10 epochs training with a learning rate range=(1e-6, 1e-4), the learning rate range will become: (1e-6*0.16, 1e-4*0.16).
  - Within each 10 epoch cycle, the one cycle learning rate schedule from Fast.AI was used with the decaying learning rate range.

Further implementation details are: batch size=128; dropout parameter PS=0.5; use of SGD (stochastic gradient descent) optimizer with weight decay=0.1; momentum for SGD to change in the range of (0.95, 0.85) along with a learning rate following the one cycle schedule by Fast.AI-.Training the classification layer by freezing the base architect using fit_one_cycle with discriminative learning rate=slice(0.01); using fit_one_cycle with discriminative learning rate range starts with: slice(1e-6, 1e-4) followed by a staircase decay for every 10 epochs with a decay rate 0.16 as described previously.

Example 6—Consensus Labelling for Ovarian Cancer

This Example follows the consensus labelling (with LASSO logistic regression) approach disclosed in Example 2, although in this case it was performed with the ovarian cancer dataset 'TCGA-OV' available from The Cancer Genome Atlas (TCGA) supra. Signature 3 score, LST score, NtAI (=TAI) score, LOH score, fLOH score, and HRD score (sum of NtAI, LOH, and LST scores) for 386 samples were determined from the provided values in the TCGA-OV dataset.

The samples in TCGA-OV with BRCA1 and/or BRCA2 germline bi-allelic deleterious mutations were used to define the HRD group of (ground truth) samples in the full TCGA-OV sample set. These are termed the 'ground truth HRD samples' in this Example.

As in Example 2, a plurality of different threshold pairs (in this case using the e threshold range of 30-50 (inclusive) and an increment of 2) for the HRD score and Signature 3 score were used to identify varying putative 'ground truth' HRP samples in the TCGA-OV dataset.

For each of the 121 threshold pairs, LASSO logistic regression was used to train a classification model by estimating the β (feature weights) for all features (Signature 3 score, LST score, NtAI score, LOH score, HRD score, and fLOH) based on the scores for those features in the ground truth HRD samples and the ground truth HRP samples for the threshold pair.

Each trained model was then used to determine the HRD probability for each sample in the full TCGA-OV ovarian cancer set. The results from each model were then aggregated on a heatmap (showing the HRD probability for each sample at each threshold pair). The samples in the full TCGA-OV dataset which were consistently, across all threshold pairs, below a selected HRD probability (e.g. 0.5) were then used as new putative ground truth HRP samples.

A final round of LASSO logistic regression was then performed with a training set comprised of the ground truth HRD samples and the new ground truth HRP samples. This final round of LASSO logistic regression determines the most relevant features and corresponding weights for the final classification model.

Figure 10:
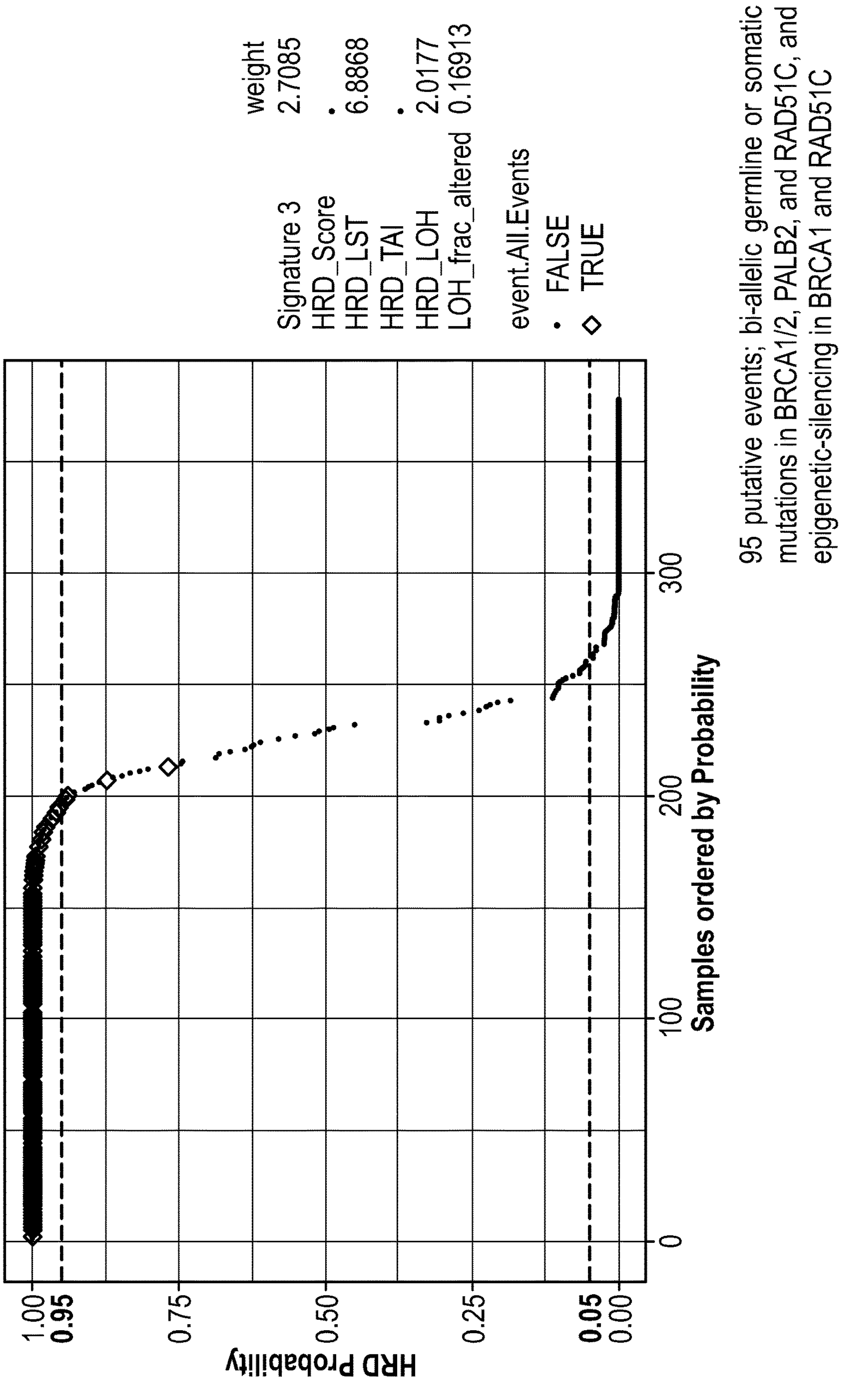
FIG. 10 shows the classification results from a trained machine learning model for classifying a set of unlabeled cancers.

The trained classification model from this final round of training was then applied to the full TCGA-OV dataset. FIG. 10 shows the resulting characteristic logistic curve, plotting the HRD probabilities for each sample in the TCGA-OV dataset. The weights for the features are also shown in FIG. 10. As can be seen, the final model accurately predicts true positives for HRD status above an HRD probability of 0.95 and accurately predicts true negatives for HRD status (i.e. HRP) below an HRD probability of 0.05. Moreover, the final model identifies many HRD and HRP samples meeting these respective thresholds.

These HRD probability thresholds for HRD and HRP can be used to select TCGA-OV cancer samples whose corresponding slides can be labelled as (the putative) ground truth HRD or HRP (or some other assign) to create a training set of cancer images for training a machine learning model to determine the HRD status of an ovarian cancer from its image, such as used in other Examples herein.

Examples—Miscellaneous

Image Augmentation:

In embodiments and Examples of the invention, image augmentation may be applied by flipping (horizontally or vertically) and/or rotating the image.

HRP Tile Label Correction in HRD Slides:

The labels of some tiles from HRD slides may be false labels. In embodiments and Examples of the invention, tiles that are predicted as HRD tiles with probability less than a cut-off may be relabeled as HRP or dropped to improve learning. The cut-off for relabeling tiles to HRP (or dropping) in HRD slides may be an HRD probability that is less than (or less than about one-half of) the average (e.g. median) of the HRD probability distribution for all training tiles of the HRP training images. This cut-off may be selected after sufficient training cycles to segregate the HRD probability distributions for the tiles of the HRD and HRP towards their respective HRD probability classes (e.g. the average of the probability distribution for HRD training tiles one moving closer towards an HRD probability of 1 and the average probability distribution for the HRP training tiles moving closer towards an HRD probability of 0).

Whole Slide HRD Status Prediction from Tiles:

As mentioned hereinabove, because a whole slide image is too big to feed into a neural network, each slide is partitioned into small tiles of size 512×512 pixels and the learning is done at tile level. The HRD status for a slide is derived from the HRD probabilities calculated for each of the tiles, such as by averaging (mean), as also mentioned hereinabove. In embodiments and Examples of the invention, another means to summarize the tile HRD prediction for the parent slide is to use a weighted mean approach to reduce the contribution of tiles that do not appear to represent the HRD signal and to increase the contribution of tiles that appear to represent the HRD signal. One approach is to first identify the HRD probability distribution of the HRP tiles p(x) and then average $1-p(x_t)$ of all tiles, where $x_t$ is the HRD probability of tile t.

Cancer Sub-Types:

In embodiments and Examples of the invention, if the cancer to be characterized has known sub-types, the training dataset split (into training, validation and/or test sets) may be done so as to ensure each cancer sub-type is proportionally represented in the respective sets/splits so the model learns from all sub-types.

Summary

It is believed that the Examples and disclosure herein showing that it is possible to characterize the HRD status in a breast cancer from an image thereof establishes the ability to generalize this HRD status determination approach to other cancers, and in particular cancers for which HRD is a biomarker (of which ovarian cancer is a known example) or against which PARP inhibitors or other anti-cancer agents are effective due to the cancer being HRD.

Example 7—Characterizing Microsatellite Instability Status Based on Cancer Images Cancer images labeled as having a microsatellite instability (MSI) or as being microsatellite stable (MSS) are used to train a classification model. The cancer images are labeled according to a labeled cancer associated with the image data. The cancer can be labeled using a dMMR IHC test or a PCR expression test. The dMMR IHC and PCR expression tests compare expression of mismatch repair (MMR) proteins MLH1, MSH2, MSH6, and PMS2. Unlabeled cancer images can inputted into the trained model to determine the microsatellite instability status (e.g., MSI or MSS, or probability thereof) of the cancer associated with the image.

This Example may be carried out using the methodology and systems (learning models etc.) as described herein for labelling and classification of cancer HRD status, especially Examples 1-6. It can be anticipated to generate an ROC curve that indicates the presence of a signal for the required classification.

Example 8—Characterizing Tumor Mutational Burden Status Based on Cancer Images

Cancer images labeled as having a high tumor mutation burden (TMB-H) or low tumor mutation burden (TMB-L) are used to train a classification model. The cancer images are labeled according to a labeled cancer associated with the image data. Whole or partial (either targeted or untargeted) genome sequencing is used to estimate the mutational burden of the cancer genome, and a threshold can be established to distinguish TMB-H and TMB-L cancers. An exemplary TMB threshold is 20 mutations per megabase (Mb), wherein a cancer genome having 20 or more mutations per megabase indicates a TMB-H cancer, and a cancer genome having fewer than 20 mutations per megabase indicates a TMB-L cancer.

This Example may be carried out using the methodology and systems (learning models etc.) as described herein for labelling and classification of cancer HRD status, especially Examples 1-6. It can be anticipated to generate an ROC curve that would indicate the presence of a signal for the required classification.

It will be understood and appreciated that each of the Examples of the present invention may be varied or modified, in particular as is described elsewhere in the present specification and/or to incorporate features or techniques which are common general knowledge.

What is claimed is:

1. A computer-implemented method of identifying a cancer as homologous recombination deficient or homologous recombination proficient, comprising:

inputting image data comprising tiles or pixels corresponding to a digitized image of the cancer into a trained machine learning model, trained on training image data comprising a plurality of digitized images associated with a homologous recombination status;

processing, using one or more processors, the inputted image data by the trained machine learning model that associates the inputted image data with a homologous recombination deficiency status, wherein the trained machine learning model comprises (i) a deep learning model (ii) a convolutional neural network (CNN) learning model, (iii) an ensemble model or (iv) an image classification model, and wherein the trained machine learning model comprises one or more weighted features including a first feature comprising a mutational signature score associated with the cancer and a second feature comprising a large-scale state transition (LST) score associated with the cancer;

outputting, from the trained machine learning model, an output indicating the homologous recombination deficiency status of the cancer; and identifying the cancer as homologous recombination deficient (HRD) or homologous recombination proficient (HRP) based on the output indicating the homologous recombination deficiency status of the cancer.

2. The computer-implemented method of claim 1, wherein the homologous recombination deficiency status comprises (i) a likelihood that the cancer is homologous recombination deficient or a likelihood that the cancer is homologous recombination proficient and/or (ii) a binary determination that the cancer is homologous recombination deficient or homologous recombination proficient.

3. The computer-implemented method of claim 1, wherein the image data is obtained from a stained image of cancer or an image of a specimen sample of cancer or a histology image of cancer or any combination of the foregoing.

4. The computer-implemented method of claim 1, wherein the trained machine learning (ML) model is an image classification model that is a binary image classification model configured to classify the cancer in the inputted cancer image according to classes which respectively represent HRD and HRP.

5. A computer-implemented method of diagnosing cancer as HRD in a human comprising the steps of applying the method of claim 1 to an image of the cancer.

6. The computer-implemented method of claim 1, wherein the cancer is selected from the group consisting of epithelial cancer, breast cancer, ovarian cancer, fallopian tube cancer, peritoneal cancer, colon cancer, colorectal cancer, rectal cancer, cholagiocarcinoma, gastric cancer, and endometrial cancer.

7. A computer-implemented method for identifying whether a cancer in a subject is homologous recombination deficient (HRD) comprising the steps of:

i. receiving an image of the subject's cancer, wherein the image comprises tiles or pixels corresponding to a digitized image of the cancer, and ii. processing said image, using one or more processors, with an image analysis system and using a trained image classification model to determine a homologous recombination deficiency status to identify therefrom if the cancer is HRD, wherein the trained image classification model comprises one or more weighted features including a first feature comprising a mutational signature score associated with the cancer and a second feature comprising a large-scale state transition (LST) score associated with the cancer, and iii. outputting a result including the HRD status from the image processing step.

8. The computer-implemented method of claim 7, wherein the image classifier is a binary image classifier for classes for HRD and not-HRD.

9. A system to identify a homologous recombination (HR) status of a cancer of a subject, preferably whether the cancer of the subject is HR deficient (HRD) or whether the cancer is HRD or other than HRD, the system comprising an image analysis system and one or more processors configured to:

i) receive as input an image of the cancer of the subject, wherein the image comprises tiles or pixels corresponding to a digitized image of the cancer, ii) process the cancer image with a trained machine learning (ML) model to determine the HR status of the cancer of the subject from the image of the cancer, wherein the trained ML model is (a) trained by supervised learning, (b) a deep learning (DL) model, (c) configured by at least one artificial neural network, (d) a convolutional neural network learning model, (e) an ensemble model, or (f) any combination of the foregoing options (a) to (e), wherein the trained machine learning model comprises an image classification model and one or more weighted features including a first feature comprising a mutational signature score associated with the cancer and a second feature comprising a large-scale state transition (LST) score associated with the cancer, and iii) provide an output to indicate the HR status for the cancer based on the processing of the image of said cancer by the trained ML model.

10. The system of claim 9, wherein the image analysis system has an image pre-processor to process the image of the cancer received as input prior to processing by the trained ML model.

11. The system of claim 9, wherein the image is of a specimen sample of the cancer or is of a stained cancer sample or is in the form of image data or is any combination of the foregoing.

12. The system of claim 9, wherein the trained ML model comprises a classifier to classify the cancer in the input cancer image with respect to a class set which is representative of a set of HR classes, preferably a class for HRD and a class for one or more other HR classes.

13. The system of claim 12, wherein the output is the classification of the cancer in the input cancer image with respect to the class set or the classifier is a binary classifier for classes representing HRD and HRP.

14. The system of claim 9, wherein the cancer is selected from the group consisting of epithelial cancer, breast cancer, ovarian cancer, fallopian tube cancer, peritoneal cancer, colon cancer, colorectal cancer, rectal cancer, cholagiocarcinoma, gastric cancer, and endometrial cancer.

15. The system of claim 9, wherein the system outputs a diagnosis of cancer as HRD in a human based on processing the image of the cancer.

16. A computer-implemented method performed by a data processing system comprising one or more processors for identifying a cancer as homologous recombination deficient (HRD) or homologous recombination proficient (HRP), comprising:

inputting image data comprising tiles or pixels corresponding to a digitized image of the cancer into the data processing system;

accessing a computer program that includes a trained machine learning model that associates the inputted image data with a homologous recombination deficiency status, wherein the trained machine learning model comprises one or more weighted features including a first feature comprising a mutational signature score associated with the cancer and a second feature comprising a large-scale state transition (LST) score associated with the cancer;

executing the computer program with the trained machine learning model to process the inputted image data to identify image data features;

determining, based on the identified image data features, the homologous recombination deficiency status for the inputted image data; and storing, in memory, a data structure with fields representing the inputted image data and its homologous recombination deficiency status.

17. A computer program product comprising a computer readable storage medium comprising instructions which, when the program is executed by a computer or data processor(s), cause the computer or data processor(s) to process a digitized image of a cancer to determine or predict a homologous recombination deficient (HRD) status of the cancer, wherein the instructions when executed implement (a) a trained machine learning model, wherein the trained machine learning model comprises an image classification model and one or more weighted features including a first feature comprising a mutational signature score associated with the cancer and a second feature comprising a large-scale state transition (LST) score associated with the cancer, and wherein the instructions when executed provide an output with an indication of the HRD status.

18. A computer-readable data carrier having stored thereon the computer program product of claim 17.

* * * * *